(12) United States Patent
Wei et al.

(10) Patent No.: US 6,649,385 B2
(45) Date of Patent: Nov. 18, 2003

(54) ISOLATED NUCLEIC ACID MOLECULES ENCODING HUMAN SQUALENE SYNTHASE PROTEINS, AND RELATED PRODUCTS AND PROCESSES

(75) Inventors: Ming-Hui Wei, Germantown, MD (US); Chunhua Yan, Boyds, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 90 days.

(21) Appl. No.: 09/820,004

(22) Filed: Mar. 29, 2001

(65) Prior Publication Data

US 2002/0142418 A1 Oct. 3, 2002

(51) Int. Cl.⁷ .................................................. C12N 9/00

(52) U.S. Cl. ................. 435/183; 435/320.1; 435/252.3; 435/254.11; 435/325; 435/419; 536/23.1; 536/23.2; 536/23.5

(58) Field of Search ............................... 536/23.1, 23.2, 536/23.5; 435/320.1, 252.3, 254.11, 419, 325, 183

(56) References Cited

PUBLICATIONS

Summers et al. Cloning, expression and characterization of the cDNA encoding human hepatic squalene synthase, and its relationship to phytoene synthase. Gene (1993) 136:185–192.*

Robinson et al., "Conservation Between Human and Fungal Squalene Synthetases: Similarities in Structure and Function." Molecular and Cellular Biology 1993. vol. 13, No. 5, pp. 2706–2717.

Jiang et al. "Transcriptional Regulation by Lovastatin and 25–Hydroxycholesterol in HepG2 Cells and Molecular Cloning and Expression of the cDNA for the Human Hepatic Squalene Synthase." J. Biol. Chem. 1993. vol. 268, No. 17, pp. 12818–12824.

* cited by examiner

Primary Examiner—Ponnathapu Achutamurthy
Assistant Examiner—Kathleen Kerr
(74) Attorney, Agent, or Firm—Celera Genomics; Justin D. Karjala

(57) ABSTRACT

The present invention provides amino acid sequences of human squalene synthase proteins and nucleic acid sequences encoding these squalene synthase proteins. The present invention provides isolated squalene synthase proteins and encoding nucleic acid molecules, vectors and host cells containing these nucleic acid molecules, and processes for producing the squalene synthase proteins.

24 Claims, 32 Drawing Sheets

```
   1 GCGCCTGGGG ACCGCAGAGG TGAGAGTCGC GCCCGGGAGT CCGCCGCCTG
  51 CGCCAGGATG GAGTTCGTGA AATGCCTTGG CCACCCCGAA GAGTTCTACA
 101 ACCTGGTGCG CTTCCGGATC GGGGGCAAGC GGAAGGTGAT GCCCAAGATG
 151 GACCAGGACT CGCTCAGCAG CAGCCTGAAA ACTTGCTACA AGTATCTCAA
 201 TCAGACCAGT CGCAGTTTCG CAGCTGTTAT CCAGGCGCTG GATGGGGAAA
 251 TGCGCAACGC AGTGTGCATA TTTTATCTGG TTCTCCGAGC TCTGGACACA
 301 CTGGAAGATG ACATGACCAT CAGTGTGGAA AAGAAGGTCC CGCTGTTACA
 351 CAACTTTCAC TCTTTCCTTT ACCAACCAGA CTGGCGGTTC ATGGAGAGCA
 401 AGGAGAAGGA TCGCCAGGTG CTGGAGGACT TCCCAACGTA CTGCCACTAT
 451 GTTGCTGGGC TGGTCGGAAT TGGCCTTTCC CGTCTTTTCT CAGCCTCAGA
 501 GTTTGAAGAC CCCTTAGTTG GTGAAGATAC AGAACGTGCC AACTCTATGG
 551 GCCTGTTTCT GCAGAAAACA AACATCATCC GTGACTATCT GGAAGACCAG
 601 CAAGGAGGAA GAGAGTTCTG GCCTCAAGAG GTTTGGAGCA GGTATGTTAA
 651 GAAGTTAGGG GATTTGCTA AGCCGGAGAA TATTGACTTG GCCGTGCAGT
 701 GCCTGAATGA ACTTATAACC AATGCACTGC ACCACATCCC AGATGTCATC
 751 ACCTACCTTT CGAGACTCAG AAACCAGAGT GTGTTTAACT TCTGTGCTAT
 801 TCCACAGGTG ATGGCCATTG CCACTTTGGC TGCCTGTTAT AATAACCAGC
 851 AGGTGTTCAA AGGGGCAGTG AAGATTCGGA AAGGGCAAGC AGTGACCCTC
 901 ATGATGGATG CCACCAATAT GCCAGCTGTC AAAGCCATCA TATATCAGTA
 951 TATGGAAGAG ATTTATCATA GAATCCCCGA CTCAGACCCA TCTTCTAGCA
1001 AAACAAGGCA GATCATCTCC ACCATCCGGA CGCAGAATCT TCCCAACTGT
1051 CAGCTGATTT CCCGAAGCCA CTACTCCCCC ATCTACCTGT CGTTTGTCAT
1101 GCTTTTGGCT GCCCTGAGCT GGCAGTACCT GACCACTCTC TCCCAGGTAA
1151 CAGAAGACTA TGTTCAGACT GGAGAACACT GATCCCAAAT TTGTCCATAG
1201 CTGAAGTCCA CCATAAAGTG GATTTACTTT TTTTCTTTAA GGATGGATGT
1251 TGTGTTCTCT TTATTTTTTT CCTACTACTT TAATCCCTAA AGAACGCTG
1301 TGTGGCTGGG ACCTTTAGGA AAGTGAAATG CAGGTGAGGA GAACCTAAAC
1351 ATGAAAGGAA AGGGTGCCTC ATCCCAGCAA CCTGTCCTTG TGGGTGATGA
1401 TCACTGTGCT GCTTGCGGCT CATGGCAGAG CATTCAGTGC CACGGTTTAG
1451 GTGAAGTCGC TGCATATGTG ACTGTCATGA GATCCTACTT AGTATGATCC
1501 TGGCTAGAAT GATAATTAAA AGTATTTAAT TTGAAAAAAA AAAAAAAAAA
1551 AAAAAAAAAA AAAAAAAAAA AAAAAAAAAA AAAAAAAAAA AAAAAAAAAA
1601 AAAAAA  (SEQ ID NO:1)
```

FEATURES:
5'UTR:          1-57
Start Codon:    58
Stop Codon:     1180
3'UTR:          1183

Homologous proteins:
Top 10 BLAST Hits

```
                                                              Score      E
CRA|108000024649260 /altid=gi|12734163 /def=ref|XP_005134.2| fa...   770    0.0
CRA|18000004925908  /altid=gi|4758350  /def=ref|NP_004453.1| farn...  743    0.0
CRA|18000004929946  /altid=gi|2135096  /def=pir||I38245 farnesyl-... 741    0.0
CRA|18000004993865  /altid=gi|2136196  /def=pir||I52090 squalene ... 740    0.0
CRA|18000004932414  /altid=gi|6753838  /def=ref|NP_034321.1| farn... 671    0.0
CRA|18000004937535  /altid=gi|9506591  /def=ref|NP_062111.1| farn... 654    0.0
CRA|1000682330885   /altid=gi|6002565  /def=gb|AAF00038.1| (AF0903... 582   e-165
CRA|335001098694081 /altid=gi|11514495 /def=pdb|1EZF|A Chain A,...   579   e-164
CRA|18000005103884  /altid=gi|2463565  /def=dbj|BAA22557.1| (AB00... 282   1e-74
CRA|18000005103885  /altid=gi|7434086  /def=pir||T00489 farnesyl-... 280   4e-74
```

FIGURE 1, page 1 of 2

BLAST dbEST hits:

```
                                               Score    E
gi|12926380 /dataset=dbest /taxon=960...       1441    0.0
gi|12945082 /dataset=dbest /taxon=960...       1370    0.0
gi|12921315 /dataset=dbest /taxon=960...       1346    0.0
gi|11642571 /dataset=dbest /taxon=96...        1330    0.0
gi|9141948  /dataset=dbest /taxon=9606...      1281    0.0
gi|13040072 /dataset=dbest /taxon=960...       1233    0.0
gi|12944143 /dataset=dbest /taxon=960...       1055    0.0
```

EXPRESSION INFORMATION FOR MODULATORY USE:
library source:
From BLAST dbEST hits:
gi|12926380 placenta
gi|12945082 T cells from T cell leukemia
gi|12921315 Fetal brain
gi|11642571 pancreas
gi|9141948 Burkitt lymphoma
gi|13040072 bladder From tissue screening panels:
Whole liver

```
  1 MEFVKCLGHP EEFYNLVRFR IGGKRKVMPK MDQDSLSSSL KTCYKYLNQT
 51 SRSFAAVIQA LDGEMRNAVC IFYLVLRALD TLEDDMTISV EKKVPLLHNF
101 HSFLYQPDWR FMESKEKDRQ VLEDFPTYCH YVAGLVGIGL SRLFSASEFE
151 DPLVGEDTER ANSMGLFLQK TNIIRDYLED QQGGREFWPQ EVWSRYVKKL
201 GDFAKPENID LAVQCLNELI TNALHHIPDV ITYLSRLRNQ SVFNFCAIPQ
251 VMAIATLAAC YNNQQVFKGA VKIRKGQAVT LMMDATNMPA VKAIIYQYME
301 EIYHRIPDSD PSSSKTRQII STIRTQNLPN CQLISRSHYS PIYLSFVMLL
351 AALSWQYLTT LSQVTEDYVQ TGEH    (SEQ ID NO:2)
```

FEATURES:
Functional domains and key regions:
[1] PDOC00001 PS00001 ASN_GLYCOSYLATION
N-glycosylation site Number of matches: 2
    1      48-51 NQTS
    2   239-242 NQSV

[2] PDOC00005 PS00005 PKC_PHOSPHO_SITE
Protein kinase C phosphorylation site

Number of matches: 5
    1     39-41 SLK
    2     50-52 TSR
    3   158-160 TER
    4   313-315 SSK
    5   322-324 TIR

[3] PDOC00006 PS00006 CK2_PHOSPHO_SITE
Casein kinase II phosphorylation site

Number of matches: 3
    1     81-84 TLED
    2   145-148 SASE
    3   147-150 SEFE

[4] PDOC00008 PS00008 MYRISTYL
N-myristoylation site

Number of matches: 2
    1   137-142 GIGLSR
    2   276-281 GQAVTL

[5] PDOC00009 PS00009 AMIDATION
Amidation site 22-25 GGKR

[6] PDOC00802 PS01044 SQUALEN_PHYTOEN_SYN_1
Squalene and phytoene synthases signature 1

128-143 YCHYVAGLVGIGLSRL

[7] PDOC00802 PS01045 SQUALEN_PHYTOEN_SYN_2
Squalene and phytoene synthases signature 2

164-189 MGLFLQKTNIIRDYLEDQQGGREFWP

FIGURE 2, page 1 of 5

Membrane spanning structure and domains:

| Helix | Begin | End | Score | Certainty |
|---|---|---|---|---|
| 1 | 125 | 145 | 0.834 | Putative |
| 2 | 241 | 261 | 1.467 | Certain |
| 3 | 339 | 359 | 1.716 | Certain |

FIGURE 2, page 2 of 5

BLAST Alignment to Top Hit:
```
>CRA|18000004925908 /altid=gi|4758350 /def=ref|NP_004453.1|
          farnesyl-diphosphate farnesyltransferase 1;
          Farnesyl-diphosphate farnesyltransferase 1 (squalene
          synthase); Squalene synthase [Homo sapiens] /org=Homo
          sapiens /taxon=9606 /dataset=nraa /length=417
          Length = 417

Score =  743 bits (1898), Expect = 0.0
 Identities = 374/417 (89%), Positives = 374/417 (89%), Gaps = 43/417 (10%)

Query: 1    MEFVKCLGHPEEFYNLVRFRIGGKRKVMPKMDQDSLSSSLKTCYKYLNQTSRSFAAVIQA 60
            MEFVKCLGHPEEFYNLVRFRIGGKRKVMPKMDQDSLSSSLKTCYKYLNQTSRSFAAVIQA
Sbjct: 1    MEFVKCLGHPEEFYNLVRFRIGGKRKVMPKMDQDSLSSSLKTCYKYLNQTSRSFAAVIQA 60

Query: 61   LDGEMRNAVCIFYLVLRALDTLEDDMTISVEKKVPLLHNFHSFLYQPDWRFMESKEKDRQ 120
            LDGEMRNAVCIFYLVLRALDTLEDDMTISVEKKVPLLHNFHSFLYQPDWRFMESKEKDRQ
Sbjct: 61   LDGEMRNAVCIFYLVLRALDTLEDDMTISVEKKVPLLHNFHSFLYQPDWRFMESKEKDRQ 120

Query: 121  VLEDFPT---------------------------------------YCHYVAGLVG 137
            VLEDFPT                                       YCHYVAGLVG
Sbjct: 121  VLEDFPTISLEFRNLAEKYQTVIADICRRMGIGMAEFLDKHVTSEQEWDKYCHYVAGLVG 180

Query: 138  IGLSRLFSASEFEDPLVGEDTERANSMGLFLQKTNIIRDYLEDQQGGREFWPQEVWSRYV 197
            IGLSRLFSASEFEDPLVGEDTERANSMGLFLQKTNIIRDYLEDQQGGREFWPQEVWSRYV
Sbjct: 181  IGLSRLFSASEFEDPLVGEDTERANSMGLFLQKTNIIRDYLEDQQGGREFWPQEVWSRYV 240

Query: 198  KKLGDFAKPENIDLAVQCLNELITNALHHIPDVITYLSRLRNQSVFNFCAIPQVMAIATL 257
            KKLGDFAKPENIDLAVQCLNELITNALHHIPDVITYLSRLRNQSVFNFCAIPQVMAIATL
Sbjct: 241  KKLGDFAKPENIDLAVQCLNELITNALHHIPDVITYLSRLRNQSVFNFCAIPQVMAIATL 300

Query: 258  AACYNNQQVFKGAVKIRKGQAVTLMMDATNMPAVKAIIYQYMEEIYHRIPDSDPSSSKTR 317
            AACYNNQQVFKGAVKIRKGQAVTLMMDATNMPAVKAIIYQYMEEIYHRIPDSDPSSSKTR
Sbjct: 301  AACYNNQQVFKGAVKIRKGQAVTLMMDATNMPAVKAIIYQYMEEIYHRIPDSDPSSSKTR 360

Query: 318  QIISTIRTQNLPNCQLISRSHYSPIYLSFVMLLAALSWQYLTTLSQVTEDYVQTGEH 374
            QIISTIRTQNLPNCQLISRSHYSPIYLSFVMLLAALSWQYLTTLSQVTEDYVQTGEH
Sbjct: 361  QIISTIRTQNLPNCQLISRSHYSPIYLSFVMLLAALSWQYLTTLSQVTEDYVQTGEH 417    (SEQ
ID NO:4)

>CRA|108000024649260 /altid=gi|12734163 /def=ref|XP_005134.2|
          farnesyl-diphosphate farnesyltransferase 1 [Homo
          sapiens] /org=Homo sapiens /taxon=9606 /dataset=nraa
          /length=431
          Length = 431

Score =  743 bits (1898), Expect = 0.0
 Identities = 374/417 (89%), Positives = 374/417 (89%), Gaps = 43/417 (10%)

Query: 1    MEFVKCLGHPEEFYNLVRFRIGGKRKVMPKMDQDSLSSSLKTCYKYLNQTSRSFAAVIQA 60
            MEFVKCLGHPEEFYNLVRFRIGGKRKVMPKMDQDSLSSSLKTCYKYLNQTSRSFAAVIQA
Sbjct: 15   MEFVKCLGHPEEFYNLVRFRIGGKRKVMPKMDQDSLSSSLKTCYKYLNQTSRSFAAVIQA 74

Query: 61   LDGEMRNAVCIFYLVLRALDTLEDDMTISVEKKVPLLHNFHSFLYQPDWRFMESKEKDRQ 120
            LDGEMRNAVCIFYLVLRALDTLEDDMTISVEKKVPLLHNFHSFLYQPDWRFMESKEKDRQ
Sbjct: 75   LDGEMRNAVCIFYLVLRALDTLEDDMTISVEKKVPLLHNFHSFLYQPDWRFMESKEKDRQ 134

Query: 121  VLEDFPT---------------------------------------YCHYVAGLVG 137
            VLEDFPT                                       YCHYVAGLVG
Sbjct: 135  VLEDFPTISLEFRNLAEKYQTVIADICRRMGIGMAEFLDKHVTSEQEWDKYCHYVAGLVG 194
```

FIGURE 2, page 3 of 5

```
Query: 138  IGLSRLFSASEFEDPLVGEDTERANSMGLFLQKTNIIRDYLEDQQGGREFWPQEVWSRYV 197
            IGLSRLFSASEFEDPLVGEDTERANSMGLFLQKTNIIRDYLEDQQGGREFWPQEVWSRYV
Sbjct: 195  IGLSRLFSASEFEDPLVGEDTERANSMGLFLQKTNIIRDYLEDQQGGREFWPQEVWSRYV 254

Query: 198  KKLGDFAKPENIDLAVQCLNELITNALHHIPDVITYLSRLRNQSVFNFCAIPQVMAIATL 257
            KKLGDFAKPENIDLAVQCLNELITNALHHIPDVITYLSRLRNQSVFNFCAIPQVMAIATL
Sbjct: 255  KKLGDFAKPENIDLAVQCLNELITNALHHIPDVITYLSRLRNQSVFNFCAIPQVMAIATL 314

Query: 258  AACYNNQQVFKGAVKIRKGQAVTLMMDATNMPAVKAIIYQYMEEIYHRIPDSDPSSSKTR 317
            AACYNNQQVFKGAVKIRKGQAVTLMMDATNMPAVKAIIYQYMEEIYHRIPDSDPSSSKTR
Sbjct: 315  AACYNNQQVFKGAVKIRKGQAVTLMMDATNMPAVKAIIYQYMEEIYHRIPDSDPSSSKTR 374

Query: 318  QIISTIRTQNLPNCQLISRSHYSPIYLSFVMLLAALSWQYLTTLSQVTEDYVQTGEH 374
            QIISTIRTQNLPNCQLISRSHYSPIYLSFVMLLAALSWQYLTTLSQVTEDYVQTGEH
Sbjct: 375  QIISTIRTQNLPNCQLISRSHYSPIYLSFVMLLAALSWQYLTTLSQVTEDYVQTGEH 431   (SEQ
ID NO:5)

>CRA|18000004929946 /altid=gi|2135096 /def=pir||I38245
        farnesyl-diphosphate farnesyltransferase (EC 2.5.1.21),
        hepatic - human /org=human /taxon=9606 /dataset=nraa
        /length=417
        Length = 417

Score =  741 bits (1893), Expect = 0.0
 Identities = 373/417 (89%), Positives = 373/417 (89%), Gaps = 43/417 (10%)

Query: 1    MEFVKCLGHPEEFYNLVRFRIGGKRKVMPKMDQDSLSSSLKTCYKYLNQTSRSFAAVIQA 60
            MEFVKCLGHPEEFYNLVRFRIGGKRKVMPKMDQDSLSSSLKTCYKYLNQTSRSFAAVIQA
Sbjct: 1    MEFVKCLGHPEEFYNLVRFRIGGKRKVMPKMDQDSLSSSLKTCYKYLNQTSRSFAAVIQA 60

Query: 61   LDGEMRNAVCIFYLVLRALDTLEDDMTISVEKKVPLLHNFHSFLYQPDWRFMESKEKDRQ 120
            LDGEMRNAVCIFYLVLRALDTLEDDMTISVEKKVPLLHNFHSFLYQPDWRFMESKEKDRQ
Sbjct: 61   LDGEMRNAVCIFYLVLRALDTLEDDMTISVEKKVPLLHNFHSFLYQPDWRFMESKEKDRQ 120

Query: 121  VLEDFPT---------------------------------------YCHYVAGLVG 137
            VLEDFPT                                       YCHYVAGLVG
Sbjct: 121  VLEDFPTISLEFRNLAEKYQTVIADICRRMGIGMAEFLDKHVTSEQEWDKYCHYVAGLVG 180

Query: 138  IGLSRLFSASEFEDPLVGEDTERANSMGLFLQKTNIIRDYLEDQQGGREFWPQEVWSRYV 197
            IGLSRLFSASEFEDPLVGEDTERANSMGLFLQKTNIIRDYLEDQQGGREFWPQEVWSRYV
Sbjct: 181  IGLSRLFSASEFEDPLVGEDTERANSMGLFLQKTNIIRDYLEDQQGGREFWPQEVWSRYV 240

Query: 198  KKLGDFAKPENIDLAVQCLNELITNALHHIPDVITYLSRLRNQSVFNFCAIPQVMAIATL 257
            KKLGDFAKPENIDLAVQCLNELITNALHHIPDVITYLSRLRNQSVFNFCAIPQVMAIATL
Sbjct: 241  KKLGDFAKPENIDLAVQCLNELITNALHHIPDVITYLSRLRNQSVFNFCAIPQVMAIATL 300

Query: 258  AACYNNQQVFKGAVKIRKGQAVTLMMDATNMPAVKAIIYQYMEEIYHRIPDSDPSSSKTR 317
            AACYNNQQVFKGAVKIRKGQAVTLMMDATNMPAVKAIIYQYMEEIYHRIPDSDPSSSKTR
Sbjct: 301  AACYNNQQVFKGAVKIRKGQAVTLMMDATNMPAVKAIIYQYMEEIYHRIPDSDPSSSKTR 360

Query: 318  QIISTIRTQNLPNCQLISRSHYSPIYLSFVMLLAALSWQYLTTLSQVTEDYVQTGEH 374
            QIISTIRTQNLPNCQLISRSHYSPIYLSFVMLLAALSWQYL TLSQVTEDYVQTGEH
Sbjct: 361  QIISTIRTQNLPNCQLISRSHYSPIYLSFVMLLAALSWQYLATLSQVTEDYVQTGEH 417   (SEQ
ID NO:6)
```

FIGURE 2, page 4 of 5

Hmmer search results (Pfam):

| Model | Description | Score | E-value | N |
|---|---|---|---|---|
| PF00494 | Squalene and phytoene synthases | 425.8 | 4e-124 | 2 |

Parsed for domains:

| Model | Domain | seq-f | seq-t | | hmm-f | hmm-t | | score | E-value |
|---|---|---|---|---|---|---|---|---|---|
| PF00494 | 1/2 | 47 | 126 | .. | 1 | 88 | [. | 124.6 | 1.1e-33 |
| PF00494 | 2/2 | 127 | 291 | .. | 146 | 317 | .] | 301.1 | 1.3e-86 |

FIGURE 2, page 5 of 5

```
   1 TATTTATTCC TAATTAAATG GGGAGGAAAG TCTTTGAAGA GGAACCTCTA
  51 CTTTACTTTT TATACCGTCA TGGCTGGAAA CTAAGTTTTT AAGATTTTTC
 101 TGGGGTTCCC TTGGCCGAGG TGGGGAGTGG GAGGGCTGTC CAGTGGTAGG
 151 GACTTAGGAT TTTTAGTTTA CAGTAGTAGG GGAAACACTC TGTAATCTAA
 201 TACATAAGTA AATGATGTAT TAGAATATGG TAAATATAGG CAAGTAGACC
 251 CCCACTGGGA TTAGCAGTGG TGGAAATGTG AGAGAGGGCA AACAGGTGGG
 301 TCTAGATGAG GTGTGAGCAG ACTCGAGGGG CACAGGAGTT AGTCAAGCCA
 351 GTATCTGGGG GATAGTGCAG GAATAGTGAA CAGCTAGACA AAAAGTCCTA
 401 GGGCCAGAGA AAGCAAAAGC ATAAGAGATG GAGGCCAGAG AGGTAATCTG
 451 GGTGGAAGGC TGCAGCCTCT CAGGATCCCT ATAGGTGCTT TGGCTTTTGT
 501 TGGAGAGACA CTGAACAGCT TTGGGCAGTG AACGTACCTG ACAGGTTTCC
 551 TGTTTGTTTT TGAGATGAAG TCTCGCTCTT GTCCCCAGG CTGGAGTGCA
 601 ATAGCGCGAT CTCAGCTCAC TGCAACCTCT GCCTCCTGTG TTCAAGCGAT
 651 TCTCCTGCCT CAGCCTCCCA GGTAGCTGGG ATTATAGGCG CCTGCCACCA
 701 TGCCTGGCTA ATTTTTGTAT TTTTAGTAGA GACGCAGTTT CAGCATGTTG
 751 GCCAGGCTGG TCTTGAACTC CAGACCTCAG GTGATCCGCC CGCCTTGGCC
 801 TCCCAAAGTG CTGGGATTAC AGGCGTGAGC CACCGCGCTC GGCTAGACCT
 851 GACAGGTTTT AAAAGGATTA CTGGTTGCTG TGTTAAAACA GACTGCAGGA
 901 TGGCTTAGGT AGCCAGTAGG TTTTTTTTTT TTTTGGAGAC GTAGTCTTGC
 951 TCTGTTGGCC TGGCTGGAGT GCAGCGGTGT CATCTTGGCT CACTGCAAAC
1001 TCCGCTTCCC GGGTTCAAGT GATTCTCCTG CCTCAGCCTC CGGAGTAGTT
1051 GGGACTACAG GCGCCCACCA CCACACTCGG CTTTTTGTA TTTTTAGTAG
1101 AGACGGGTTT CACCATGTTG CCAGGATGG TCTCGATCTC TTGACCTCGT
1151 GATCCACCCG CCTTGGCCTC CCAAAGTGTT GCGATTACAG GCGTGAGCCA
1201 CCACGCCTGG ACGGGTAGCC AGTAGTTTCT AGGGCTGGAG AGATCTAGGA
1251 TGAGAGAAGT TTCCACATTC CTGTTACAGG CTCTCTAAGG CTTCAGCTCC
1301 TTTTTCTAGG ACTAAGCTGG ATCTCAAGTA AACACTAGAG AGGGGGCAGC
1351 TGAAGCTCCA GGAGTGTGTG GGGCTCCCTG GGGCTGGATG GCGGTGGCGG
1401 GCAGGCGAGC TGGGCTGTGC TCGGGTGTGT TACAGTAAAG ACGCCCAGCT
1451 TGGCGCTGGC CCGGCCTTTT CACGGTTTTA GGCTCTACAG AGAGCGGCTG
1501 CAGAGCTCAC CCGGCTGGCA GGAGCCACCG AGGCCGGACA CGTGGGCGAC
1551 TTATTGACCA AGTGGGGAGG AAGCAGCCCC GCACTGCTCT CCCGACTGCG
1601 GACCACCGTT GGGCTCATGC GCATCATAAG CCCCACCGCC TCACCTCCAG
1651 TCCCCACAGC GTTCGCGCTC CCAGCCGGGG TAAGCGGAAG AAAACAAAGG
1701 CCCGGCTCCA TCAGGGCACC AATCCCGCTC GTCGGCCTCT TTCTCGGCCT
1751 CCAATGAGCT TCTAGGGTGT TATCACGCCA GTCTCCTTCC GCGACTGATT
1801 GGCCGGGGTC TTCCTAGTGT GAGCGGCCCT GGCCAATCAG GCGCCCGTCA
1851 GCCCACCCCA CGAGGCCGCA GCTAGCCCCG CTGGCGGCCG AGGCCGGTTG
1901 AAGTGGGCGG AGCGGCGGGC GGGGCGTCGC CGTACTAGGC CTGCCCCCTG
1951 TCCGGCCAGC CCCTCGAAGC ACCTACTCCA CAGGTCCAGC CGGCCGGTGA
2001 GCGCCTGGGG ACCGCAGAGG TGAGAGTCGC GCCCGGGAGT CCGCCGCCTG
2051 CGCCAGGATG GAGTTCGTGA AATGCCTTGG CCACCCCGAA GAGTTCTACA
2101 ACCTGGTGCG CTTCCGGATC GGGGCAAGC GGAAGGTGAT GCCCAAGATG
2151 GACCAGGTGG GCCGAGCCTC CCTGCTTGCC CGGGGCGGGG AAGGAGCTCG
2201 CTGGGCCGGC CTCAGGGCCT GAGCGGCCGG GCCCGGATCT GGGGCAAGGG
2251 GCGCGGCGAG CAGGGCCGAC GCCTGGGTGT TCCCGTCCCC CTTTCCTCGA
2301 GCCTTCCCCC TGTAGGGCCC GGGTGGACGC GGCCGTCCTG GCTGACCTGT
2351 CCCTGCCCCC GCAAGCCGCC CTGGGCATGA GCGACTTTTG CGTGGTTCCC
2401 GGTGGTTGCG CTCCCCGTTT CGTCCCCTCC GTGAGCATCG GCGCTTACCG
2451 GTATTTTAAC CCGAGGGTTA CACATCTGAG GCAATGTGGG TGGGTTACGC
2501 GGGAGAGGAC GAGTGAGTTT TTTGGTAAGC GGAATGAACT ATGCAGATAA
2551 CATCACATGA AGGCCGTTTC TGGAATGAAG TCTGACTCCT CCAGTTTCAC
2601 CACCTCTTCC GGAGCTCTCC CCGCCTTGCT GCCTTCCATC GCTTCATCCT
2651 CGGTGCTTCC TGAGTTTTAA AATCGCCTAT CTACGCTTCC AAGTTCCAAT
2701 GAGTTATCTA ACGTCTATGG ATTAGCTAGG TGGTTGGTGG AAGGTCAGAA
2751 CTTGGTTTTA CTTAGATTTT TATCTGCCTC ATGCCTGTAC TATTTGTTTA
2801 ATGAATGCAT AGGAGGTGTT TTTATTCCAA CAAGAAATT ATTCGTACGC
2851 GATTATTGAA TGAATAGACA AATTCAGCCA AGTTCTCTG GTCTGGACCA
2901 GCCTGGCTGA TTTCTGTAAC TTTTTTGGGC CAACAGGACA GTAGCAAATG
2951 TGACTCAGGC CGAGGCTTGA TAGGTGCCTG AACATCGGAG TCTTTCTTTC
3001 AGTGTCCATG TGCTTCAGTA AACACACTAG AAAATAAATT TCTGGTTTTT
3051 GTCCCCAGTA GACTACACCC TCATTTGGTG TTATTTTTCA CGTGCTATCT
3101 TTAATACAGG TACATCCTTC AGTCTATTTG TAGAACATTC AGTTTTCTTC
```

FIGURE 3, page 1 of 25

```
3151 ATCTTTTCTT TGCCGGTGCT ACATTATTTG AATTATTTTG CTACAGAATA
3201 ACTTCTATTA TTTGATATGG CAGATGTCAC TTTTTATATT TAGATATAGC
3251 ATTCATTTAT TTAACAAATA TTTGACGACC AGTTGTATAT CAGATAGTGT
3301 TCTAGGTGCT GGAGGTACAA CAGTGAACAA GCTAGGTGAA GACCTTGATT
3351 TTATAAAACT TACTTTTTAG TGGAAGAGAG ACAATTTAAA AAAGCGAATG
3401 TACAGTTTTT CACGTGGAGA AAAGCACTGC AGAGGAAGAT ACTAGCAGGG
3451 CAAGGGATCT GAGTGCAGTC AGACCTCATT TGGGTCCAGA CTTCATTCCT
3501 CTATGTCTCT TTCCTTTCTA CAGAAAGACT GTTAGAGAAA ATGGTAGCAT
3551 TGGTTTCCTG TTGGGAGGGA AAGTGGGTGG TCATGGTAAG TGGGTAGAGA
3601 AAGACTTCAC AGTATACTGT TTTTGTACAT TTTGAGTTTT TTTAAAAGCG
3651 AGACTTGAGC TATTCTAGCT CTGATAATAT GGTGCAGTAT TTGTTATGTT
3701 AGTTGTAGTC TTTCTGGGCA GTTTTACAT CCCCATGAGC CGTTAAAAAA
3751 ATACCTGAAC CTTTAATTAG GGGAAATAAA TTGGAAAAAT ACATTTCCCT
3801 TCACTTAACA TTATCTTAGT TTCTCTTTTT TTTTTTTTT TTTTTTGAGA
3851 TGGAGTCTTG CTCTGTTACC CAGGCTGGAG TGCAGTGGTG GCGGGACCTC
3901 AGCTAGATGC AGCCTCCGCC TCCTGGGTTC AAGCAATTCT CCTGCCTCAG
3951 CCTGCTGAGT AGCTGGGATT ACAGGCACCT GCCACTACGC CCGGCTGATT
4001 TTTTGGTATT TTTAGTAGAG ACGGGGTTTC ACCATGTTGG CGAGGCTGGT
4051 TTTGAACTCT TGACCTCAAG TGATCTGCTC GCCTTGGTCT CCCAAAGTGC
4101 TAGGATTACA GGCGTGAGCC ACTGCACCCG GCCTTTTTTT TTTTTTTTT
4151 GAGGGGGGGG TCTCACTCCA TCGTCCAGGC TAGAATGCTG TGGCCTGAAC
4201 ATGACTCACT CCAGTTTTGA CTTCCTTGGC TGAAGCCATC CTCCCACCTC
4251 GGCTTCCTGA TCCCGAGTAG CTGGGACTCC AGGCACGTGT CACCAATGCA
4301 TGGCTAATTT TTAAATTTTT TTGTAGACAC AATGTCTCGC TGCATTGCCC
4351 AGGCTGGTCT TGAACTCCTG AGCTCAAGCG ATTTTCCCAC CTCAGCCTTC
4401 AAAGTGCTGG GATTACAGGT GTGAGCCACT GCACCCAACC AGTTTCTCTC
4451 TGCAAACTAG GGAAAAAATT TACGCTTAGC AGATATTGAG GGCTGATTAT
4501 TTCTATCACA GAAGCATTTG GCTATAGAAT TTCAGGGTTT AGTAAACTTG
4551 ATTTACACTG AATTTTTAGG TGCATATCAG TAAATCTACG GCATATGCC
4601 GCCTGCAAGT TGTGTGGCAT CACCCAAAAG CCGAGAGTAA TGGAAAGAGC
4651 AGGCTGTTAG TAATCAGGCA GATCTGGCTC CTGTCCAATC TAAATCCTGT
4701 TATTTAGACT AATATCTTAA GTCTGTTATT AAGTCCGATT TCTGACGCTA
4751 TTAAGTTAGG TGAACAACCT TGGTAACTTA ACCTCTGAAC CACAGTTACT
4801 TCATCTGTAA AATAGGGATG TATGTATGGT AACGATTTTT TAACCACAAC
4851 TTCCCAACTC TAAGATGGTC TGAAAAGAAT TTTTTGAGTG TTTGGCTCAG
4901 AATCACTTGG CAGCAAAACC TGACTTGAAG TTGAGGCTTC ATTCATCCCA
4951 CTTAGTATAT TCAAATGTTT TGCTAAAGAA ATAATTATGA GGTGCTACTT
5001 CACACTGACT AGGGTTGTAT ATGCATTTTA TTGCCTATTT TCTAAAACAC
5051 TAAAAATGCT AAATTCTGCC CCAGGTCTTG CCACAGATGT TTCAGTGGAC
5101 TATGGGCCTG TGAGACCTTA AAGGGTTGAT TGAGTAAGGA TCACAGGTGA
5151 TGTCCGCATT GTGCTTGGCA TGGAGTTAAG TGCTTGATAA ATGGTGGTTA
5201 TCAATCTGAT TATGTAAATT TATGTAAATT CAGTTCTCAA GTTGTGGTT
5251 TTTTTCCCCT CCTGGAGAAA TCTATTCTAT TTAAAGTGA GGAAGGCTCC
5301 GTGGAGGGCT GGTAGCTGGT AGCTGTTCAC TTGTGGAACT TTCAGCCTGA
5351 GGCTGGAGCC CCTTCCTGGG AGTCTGCTCT TGTCGTCTTC CTGACCACCC
5401 CCACACCCTT CCTCTAAATT CCCTCCATCC CTGTTTTTCT CCCGCTTGCG
5451 AGCTTTTGGG AGTGTGCTGA ATCTCAGACT GCAATAGATA AACCCAAGAG
5501 GGACAGGCAC CAGTAGCCTG AGCTTGCTTT CTCCCCTGGC TCATGGGAAT
5551 CAAGCAGTAG AAATTTTTAG TGAGTGTTGT TTTCCATAGT ATGCTTACTA
5601 GTTGTGTCTT CCTGTTTTGT TCTTGGTGAT TTGAAGAAAC CTGTTTACAA
5651 GGTAAGGGAC TGAAACAAAT AGGTGACAGG AAAAAGAGCA GCAGGGGTAC
5701 GAGCTGGAGG AGTAAGTGGC TTGGCTTGCT CTCTTTCAGA ATGGAGGGCT
5751 GTATGGAAAG GAGGGGTAGT GTTCTTGAAG AGTGTTGGGG TTTAAATCTA
5801 GGGGGACCGT GTCTTGGCAT TGATTGAAAC TCCTGGCTTA ACATCACCCC
5851 GAAACTGTTA GTTGGACTGA ACATGACATT TGGCAGTGCA GTTAAAAACA
5901 CTTCCTGCTG TAGCCTGGTA ATGGTCAGGC TATGTGAAGA GCTGCTCTGG
5951 AGCTCAGTCC AGAGCGGGTA TTCTGTTTCT TTCACTCTGA AATCCTGCCT
6001 CTCGATATTT TGAGAAGGAA GGAGTTGGTG AATTGTTTTA AAATCCTCGA
6051 TGAATGTCTT CATTTATTCA TGACACCACT TCTGAATATA TTTATGTGCC
6101 AGACGCTGAA GTTTACTAAT ATTATGGTGC CCAGTAAATA CTTGTTTTTA
6151 CTAATATTTT TTATGGCAAT AAAATGACTT TTTCAGGATT ATGTGATTTA
6201 AAAGATTGAC CCTTTTGGCA AAATACGTAT TCATGATAGG AAATATATAC
6251 AACATAGTTC ACTTAAACCT CCCACCAGAG CCCAGGGTTC ACTGTTACCA
```

FIGURE 3, page 2 of 25

```
6301 TTCTGAAGTG ACTGGAATTT CCTAGAAGTG GATATGCCAT ATTTTTTTAA
6351 CCACTCCTAT TGGATATTTG TTTTTTATTT TTTTGAGATG GGGTCCCACT
6401 CTGCAGTGTA CAATATCATA GTTCACTGTA ACGTGTATCT CTTGGGCTCA
6451 AGCGATCCTC CCCACCTCAG CCTCCCTGAG TAGCTAGTCT TCAGTAGCTA
6501 GACTATAGGT GGGCGCCACC ACAGCTGGCT TTTTAAAAAA TTTTTTATGA
6551 ACACGAGGTC TCACTATGTT GCCCAGGCTG CCCTCAAACT CCTGGGCTCA
6601 AGTGATTCTC CCACCTTGGC CTTCCGAAGT GCAGGGATTA TAGGCGTGCG
6651 CCACTGCACC CGGCCCTGTT GGATAAATGA TTCCAGTCTC TCCCAAAAAG
6701 AACTGTTGTA AGACTGTGGG GTGAGGGGAG GGAAGGGACA AATAGGAACC
6751 CGCCGTATTT TCCACTCCCT GTGGGCCTAA AACTGCTCTA AAAAATAGTC
6801 CATGAAAAAA TACATAGTAC AAACAGCAAC TCTTTCTGAT ATGCTTGCAT
6851 TTAAAATCAG GCTTTTTCTC CCTTTTGGAA AAACACAGTC CTTGTTTGCT
6901 TTAGGGAAGA GTAAAGGTCA GTGCGCTGCA TTGCATTAAT TTCGAAGGGA
6951 AAGATGAGAA GACATCTTGA AAGGAATGGC TGGCTTTCTA GAGAATAGTA
7001 GAGGCTTAAT AGGTGTCATA GAAAAACCAG GGTTGGACAA TGGTAGTAAA
7051 ACGGCAAAAC AGATTTTATT CAGAAAAACT ACTGCAGTAA GAGGAGAGAG
7101 ACCTCGGTAC AGAACTGCTC CACTGCGAAT ACAAAGAAAA GTAGGAATTG
7151 ATGGCGGGGG AGCCGGATGT CAGTGGATGG AAAATTATTA CGAGGAAACA
7201 CAGGGGTGTG CATTCTTGCT GAAGGCAGGC CAGAGTTATC AGACATCACC
7251 TGAGGGATGG AGGGGGATGT GGAACCTAAT CGGCTGTCTA GGGTGATCAG
7301 ATACTGAAGT TGGGGGATTC TGGTCAAATC AATTTAGCAG GATTCTTGGT
7351 AAAACTGGGC GATGCAAAGA CAGATGCGTT GAGTACAAAG TCCAGGCTTT
7401 ATTGGGAAGA GGATTTCAGC GGAGCCCGAG TAGAGTTTGG TCTAGGGAGA
7451 CTCTGTCACT GGGAGGACGA GCGAGCCGCT CGGAAGTGCG CTGGGTTCTC
7501 TTAGCGGCCA GTGGGTTCTG GTGAGAAGGG CAACAGCGGG AGGAGGCGCC
7551 GGTGCGGAGC GGGAGGCCGG GGGGGGCTG GCGGGGCTGC GGGGCGGGCC
7601 CGTTGTGGGT CGGCCCAGCG CGTATTCGAG TAGAGGGCGA GCCCGTCCCG
7651 CCTCTCGTCG GGCGCTTCCC AGATCTGCTT GAGTCTATGG AGGAAAAACT
7701 CCGCGGGGTC CGCGATTCCC ATGGCCGCAG CCGCCTGCGG CACCAAGGCC
7751 ATGGCCCTCT TCAAGCGCAC CTTGGTGCTG AGTCCCGCCG CGGCGCCCAG
7801 GGGCCCGGGC GCAGGCACCG CCCCGCGGGG CTGCTGCTTG CCTCCTGCCG
7851 CCTGGCCCTG CAAGGACTGG CCTCGGGGAG AGGGCGGCAG GCTGTGGAGC
7901 CGCCTGCCCC AGTCCCAGTC CCACTCCCAC TCCCACTCCC ACTCCCACTC
7951 CTGCTCCTCG ACGTCTCCCA CCGCCGTGTG TGTTGTCTGC CCGCAGGACT
8001 CGCTCAGCAG CAGCCTGAAA ACTTGCTACA AGTATCTCAA TCAGACCAGT
8051 CGCAGTTTCG CAGCTGTTAT CCAGGCGCTG GATGGGGAAA TGCGGTGAGT
8101 GATGGAGGCA GCGCCTCTGG CTTGGAGGAA AGCTTGTCCG GGACTTTTGA
8151 GTGTGTTGGA AGCTACCTTT TGATATAGCG CTCAGCGTTG CAGCCTCGTT
8201 GCTGTGGCTT ATCCAGAACA TAGCCCGGCC CTACGTGTTT ACTTTAGAAA
8251 GCCCTTCCAG GCTCTTTGCC ATCTAGTAGA GTCCCTGCGG GCCCAGCCTT
8301 TCAGAGAAGG GGGGGGAGGG GGTGATGTTT ATTAACTTTT TTTAGTCTTG
8351 GCAGCTGAAC CTGCCTGTGA GCAGGTCGTG TATTTCTCGG CTTCCCTTAT
8401 CCAACTTTGC ATTTCTATTT CTAGCATATT GGGTTGATTC TTTTGAAGCT
8451 GCCTCTGTGC ACATTACACC CATGAACTTA GACCAGTTGC CTTTATGTAT
8501 GATCGTATTT ATACTGAGAA GTTACTGTGT TTTTTGACTT TCTTTTCTAT
8551 TTGCTACATA TTAGTTCGGT CTAAACGTTT GGTCTTCTGG TCTCCATAGT
8601 TCTACATTGG TTAAATGCAA CTCACTTCTG GGAGTAGTGG TGACATTCAA
8651 CTAGTAGGCT TTTTAATAAA CTACAGAAGT TCATTACTCT CATGTAAGGA
8701 AGGAAAACTA ATGTAACTTT CGTTAAGTAT GAAAAGCGTT GGATATCCTT
8751 ATAGTTCTTT AGAGTTAAGG GTGAGATGGG TTTAGAAAGT GGCCAGGCAC
8801 AAGTTATTTT AAAATAAAAA ATCTTTGGCT GTTTGTTCCA ATATATTAAT
8851 AGTTTTCCCT TTTTTACAGC AACGCAGTGT GCATATTTTA TCTGGTTCTC
8901 CGAGCTCTGG ACACACTGGA AGATGACATG ACCATCAGTG TGGAAAAGAA
8951 GGTCCCGCTG TTACACAACT TTCACTCTTT CCTTTACCAA CCAGACTGGC
9001 GGTTCATGGA GAGCAAGGAG AAGGATCGCC AGGTGCTGGA GGACTTCCCA
9051 ACGGTGAGTG GGGTTACGCA TCTTGTCTAC GGACTGTTGT GTTCATAATT
9101 GCTAACGTGG TTGTCCGGTA GCCTCCATAC ATGTGGAGAA AGGTTAAATA
9151 AGCATTCTGA GGGCAGCATA ATGTGAGGGT TAAAAACTCC GGTAGCCAAG
9201 ACTCTGAAGC CAGGCTGCCT GGGTTGGAAT CTCAAATCTC CCACTTACTA
9251 AACTGTTGGT TACTTACAAA GACTCTCTGT GCCTCAGTTT CTTCATCTGT
9301 AAAATAGGGG TAATAATAAC ACCTACCTCA TGGTATTCTG AGGATTCAAA
9351 GAATTAACGT AGGTAATGCT CTTAGAATGT TAGCTACTGC TGTTATTATC
9401 AGTATTGGAA GTCCAGTGTT TCTTCCTGTG GGAAGACGCA GTCAAATTTT
```

FIGURE 3, page 3 of 25

```
 9451 AGTGTTGTGA AAGATTCTCA GGCTAGCTCA CAAAAGCCTG CCGACTGTAT
 9501 GATGCAGCCT ACCTGTAACA CTGCTGGCCT CTTGACTACC CGGAGCCTGG
 9551 TAGCATGGGA CTGCTGCTCA CGATGGGCAG CAGCCTGGCA TGGGGGCGGT
 9601 GTCTGTTGGC AGCTAGGGCG AGCCTCTGCC ACTTCACCTG TGATCCTGGG
 9651 CAAGTTCCTT ATCTGCTTTG TGTCTCCGTC TCCTCGTTTG TAAAGTTAGA
 9701 GCTGAGAGGA TTAATTTCGC ACATATAAAG TACTTAGTGC CTGGTACAGG
 9751 GTAAGTATTC TGTAAGTATT AGCTATTTGG TCTATTTTGT TGGAGTAAAG
 9801 TGGGTTATAG TTAAAATCCT AAGATTTTTA AAGTCCCTCA AGTTCACGTG
 9851 GACATCTGCC TAGGTCCTAC TATCCTAGAA TTCGCATGTC TTATCACACA
 9901 AATAACTGAT TCTTCCATAT CTTATAAATA AAGGTTTGAT TTAGCAAAGT
 9951 CACATGTTGT GTAATAGCTC GAAGAAGCCC TTTTTGTCCA CAGTTGCCAG
10001 AGCTTTTGGA GAACAGTCCT TATGTTATTG AAACAAACCT AATCTGTAGC
10051 TGAGTTGGGA GGGAGCTAAG TGGACAGAGA GTCCTCCACC CAAACAAAAG
10101 AATCTTTGAT TCTTGGGCAT AATGGGAGCA ATATTTAAAA AAAAAAAAAA
10151 AAAAAAAAAA GGAATGTTTG GGAAGACTC TTGCGGTGCA AAGGCTGTTT
10201 CAGATTGCTG AGATCAGACC TTAAGTACCA AAGCCCAAAT ATAGTACAAC
10251 ATAATACAAA TGAGAAGAAA ATAGCTGAAG AATAATTCGA GTTTATACAG
10301 TACAATTCAA GAGAAGAAAG AAAATTTATG ACGACTAGCT GGGTGAGAAT
10351 TAGAACTGTA ACCCTGGGAA GGTCCTGGTG ATTTGACTCT CACAGGACAC
10401 CTGATGACCA GAGGATGGGT TTCCTTTGAT GGGAAATCTG TGGCGATTCA
10451 TTGATGGCC TCTGAATTCT GCTGAAGCAG AGGAAGTAGT AATACCCCAT
10501 TTATAATGGA AGTGCATTCT CACTTAAAAA CAACTAATAT TATTCTAGCT
10551 GGACCTAGCC TCTAGAAACA GCCAAATTAC ATTTGACTTG AGTGGATTCA
10601 TAATAATTAA AAAATTTCTG GGGCATGGGA TAAATGTGTT AGGTATTGCT
10651 AAGTCAAGGC AGCCCTATCC CCTCAGCAGA AGTGAGGGAA TATGAAAGTG
10701 TGTGAATGCT AACATAATTT TGGGGAATAT CGCCGTCAGA TTTCCAGATG
10751 ATATTCCAAC ATGTTTGTGA AACTTCAGTG TCTTCCTGTG TTCATACAGT
10801 GTTCCAGTGG AAAAATAATG CTTAGTTCTG GAAGGTTTCA GATGTGAACA
10851 CTGAACTCAT CGTTTTCTTT TTTGGGTAGT AGAGTTAGAG ATTCCATCCT
10901 CTTGAAAGCA CAGTTGCCCC GGGAAGAGTA AAAGGGAGCA GAAGGCGTAA
10951 GCCAGGCACG GCTGTTTTCA CTGTTGTTCA CCTTTTGTAT CCTTACGAAT
11001 ATGAAGATGT ACTAAGTTGT GTGTTTTGCG TGCATATATA ATTTTAAGCT
11051 ACTTGAGTTG TAGGTCCCTC CAGTCTGTGA TTCAGTTTGA GATGGGACTG
11101 TATGGGAATT AACAGTGCCT TGTCTTCTTA AGCAGTGATT TGTGTATGTG
11151 CTGATATAGC TCAGTATGTC TTTGAAACCA GTTGTCTGGG GCTAGGCCTG
11201 CAATCAGCTT TTGGCTAAGA GGTCCCAGGA TGGAACAAGT AGTGTGAAAG
11251 AGGACTGATA CCTTGGCCTC ACACACAGTA CTGCTCTTAG ACTGGGGCAA
11301 GTGAAACTCC TCACTTCAGA GTGCCCCATT CTAGGCCCCC TCACTCCCAA
11351 AGGGGTGAGG GATCACTGGG GCCATGGGAA TGTGCTTGTT CAGCTCTCGT
11401 GGGCTCTCCT TCTGTACCAC GTTCTGGACA TCTGGAGTTC CTTGCCCCAA
11451 ATCCCTGAGC CCACGTCTGC GTCCGCACAG TCTATTTCCT AAGGTCAGTC
11501 CATCTCCTCC AGGTGGGAAC GTGCCACCAT TGACTGTGCC CTTGGGCCTG
11551 AGTGATGGCC AAGGGCTGTG TTGGGGAGTG TTGTGGATGG ATCCTGGCAC
11601 CGAGGGCTGG GATATCCTCT CAAATGAATG TGAGGTGCCT CCCAGTGCTG
11651 GAGAGAGCGG GATTCAGGAA GCAGTGGAAG GGAAGAGCCT GGGATATGGG
11701 GATCAGCTGT CTGTGCCCTG CTGCATTCTG GAATAAAACT CTGAGGGACT
11751 AAGAATTCTA AATTCAAACC TGAATCAACC AGGTTGTTAC AAAGATAAGT
11801 TTGTCAGTGC AGGAGGATAC AATATATTTT ACTTAAGTTA CTAGCTCGAT
11851 TGATCATTTT TAAATTTTTA GCTACATATA GTATGTGGGC CTCCATTTGT
11901 CCTCTTATCC CAGGCCTTGC AGAATTTAGG AATAAGCCTC AATACAGTGT
11951 TCTAACCCAG TGACTTCCGC CTCGATGTAC AGTAGATTGA ACCTGATCCT
12001 TTATACTTTA GTGATCATTA GTTGATACCA GTTCAAGTCA GGCTTTCTAG
12051 AAATCTCATT GTATGTTAGG GGTTCGATTA GAGTACAGTC ATGCATCACT
12101 TAATGAATGG CCACAGGATA CATTCTGAGA AACGCATTGA TAGATGATTT
12151 CATCATTCTG TGAACATCAT AGAGTGTACT TACACATACC AAGATGGCAT
12201 AGCTACTACA GACGTAGGCT CTGTGGTACA GGCCATTGCT CCAAGGCTGC
12251 ACATCTCTAC AGGATGGTAC TGTACTGAAT ACTGTAGGCA ATTGGAGCAC
12301 AGTGGTAAGT ATTTGTGTAT TTAAACATAG AAAAGGTATA GTAAAAACAG
12351 GGTGTTACAG TCTTAAGGGC CCACCATTGT ATTTCCAGTC TCCGTTGACT
12401 GAAACATCAT TATACAGTAC ATGAGCACGT ATCTTTCTCA CCTGGTACTA
12451 GTGGAAAGCT AGAAGGCTTA GAAGTCTACC TGTAAACATA GCTTAAGTAA
12501 TAATACAGCC TTATTTTTAA ATGATAATAG CAATAATAGT GTTCACTTAT
12551 TGAGCATTTT ACTATGAGTT ACTTACTAAA TATATTTCAT CGTTAATTTA
```

FIGURE 3, page 4 of 25

```
12601 CTCTTTGTGT TATTTGATCT ATAACATCGT TTAACAGGGA AATTACCTAG
12651 TACATAATGT ACTGTTATCT ACATTTTATC TAGATGAGGA AACTGAGGCA
12701 CAGAGAAATT AAGTACTTTG CCTAGGATTA CCCGTGAAGT TAAGTGACAG
12751 AATCAATGAA TCTGGAAGGT CTGGCTTCAG ATCTCTTGTG CTGAGTCACT
12801 CGCATACTTT ACTACCTCTA AGGTTTCTAA TCAGAGGAAT TTGTATCTGT
12851 ATTCCCTGCT ACTCTTACCC TCTATGTGGG ATTTGGCCTT TCTCCATTAT
12901 CCCTGTGAAC TCGCTCTGGG ACCTTCCTTC TTGTACTTGG AACCATCAGA
12951 AAGTGATCTG AGAACATAGA AATCTACTGT GTTGTGAAAC AGAATTACCT
13001 GGAAGCGGAA AAAGCCCTCC TGGCTCAATT CACATGTCAC GGCTTATGGT
13051 CGTATCCGGG GAACATATGA AACTGGGCAC TGAGTGCGGA GTCAGGAAAG
13101 CCCTGTCCAT CCTCTGGGTT TCTGGGGAAA ACGTGGACCC CTTCATTGTC
13151 ACTTTCTCCT GTATATTTTT GTTTTTACTT TTAGAACTGT ACAATTACGT
13201 AATAAATAAT AAAAAGTCGT TGGAAGGATA GGTGAAGTTC AGAAGTGAAA
13251 GTGTTTTGGA GGAGTCTAAG CTCCTTCCCA CCCTCATTGA CCTTTCCTCT
13301 CTAATAAATA GAACTGGTCT AACCAAGGAT CTGTGGAATG AGCAGAGTCC
13351 AACGGAGATT CAGGGATTCT AATAACCTCT TGTAGAATCA CTGGTTTGTT
13401 TCAGCCACAA GAAGGAATTA CCTTTTGACA TTGGCTTGAA CAGCTGTTGT
13451 GCAAAGAAAA ACTTTTTGGA AAGTTCTGGA AGTACCAGAT TGATTTTATA
13501 GGTTTTTTTT TTTTTTTTTG GAGGGACATG GGGGTATTGA CAGTTGATGT
13551 TAATCAGAAA TCCTAAATTA TGTGTATTCC TGGTATGTTG CAATCAGCCG
13601 GCCACCTGGT TTTCCTCTGG GCTCTTAATT TTAGGTGTAT TCCGAGGAAG
13651 TTTTTCTAAC TTTTCTGTAA ACACAGACCA GGTATATTGC ATACTTTCAA
13701 TGTTTAACCA AATCTCTTCA CTGTTTGCAG TATTATCTGT AGGCTCTCAT
13751 GTTTTAAGAC TTCCCCATGG TGTTTTGTA TTGTATTTTG CTAACCTATA
13801 AACAATTCTT TGAACTTAAA ACAAGATATT TGGGCAGTAA CAATAAATTT
13851 TAAAACATC AATTCAACTT TTTTACATTA GGGCTTGGAC TATGGAAAAA
13901 GTATTGGGCA GCATGCCTCA TACTGAGTTG TTTAATGAAT TTAAAAGTAT
13951 AGCCNNNNNN NNNNNNNNNN NNNNNNNNNN NNNNNNNNNN NNNNNNNNNN
14001 NNNNNNNNNN NNNNNNNNNN NNNNNNNNNN NNNNNNNNNN NNNNNNNNNN
14051 NNNNNNNNNN NNNNNNNNNN NNNNNNNNNN NNNNNNNNNN NNNNNNNNNN
14101 NNNNNNNNNN NNNNNNNNNN NNNNNNNNNN NNNNNNNNNN NNNNNNNNNN
14151 NNNNNNNNNN NNNNNNNNNN NNNNNNNNNN NNNNNNNNNN NNNNNNNNNN
14201 NNNNNNNNNN NNNNNNNNNN NNNNNNNNNN NNNNNNNNNN NNNNNNNNNN
14251 NNNNNNNNNN NNNNNNNNNN NNNNNNNNNN NNNNNNNNNN NNNNNNNNNN
14301 NNNNNNNNNN NNNNNNNNNN NNNNNNNNNN NNNNNNNNNN NNNNNNNNNN
14351 NNNNNNNNNN NNNNNNNNNN NNNNNNNNNN NNNNNNNNNN NNNNNNNNNN
14401 NNNNNNNNNN NNNNNNNNNN NNNNNNNNNN NNNNNNNNNN NNNNNNNNNN
14451 NNNNNNNNNN NNNNNNNNNN NNNNNNNNNN NNNNNNNNNN NNNNNNNNNN
14501 NNNNNNNNNN NNNNNNNNNN NNNNNNNNNN NNNNNNNNNN NNNNNNNNNN
14551 NNNNNNNNNN NNNNNNNNNN NNNNNNNNNN NNNNNNNNNN NNNNNNNNNN
14601 NNNNNNNNNN NNNNNNNNNN NNNNNNNNNN NNNNNNNNNN NNNNNNNNNN
14651 NNNNNNNNNN NNNNNNNNNN NNNNNNNNNN NNNNNNNNNN NNNNNNNNNN
14701 NNNNNNNNNN NNNNNNNNNN NNNNNNNNNN NNNNNNNNNN NNNNNNNNNN
14751 NNNNNNNNNN NNNNNNNNNN NNNNNNNNNN NNNNNNNNNN NNNNNNNNNN
14801 NNNNNNNNNN NNNNNNNNNN NNNNNNNNNN NNNNNNNNNN NNNNNNNNNN
14851 NNNNNNNNNN NNNNNNNNNN NNNNNNNNNN NNNNNNNNNN NNNNNNNNNN
14901 NNNNNNNNNN NNNNNNNNNN NNNNNNNNNN NNNNNNNNNN NNNNNNNNNN
14951 NNNNNNNNNN NNNNNNNNNN NNNNNNNNNN NNNNNNNNNN NNNNNNNNNN
15001 NNNNNNNNNN NNNNNNNNNN NNNNNNNNNN NNNNNNNNNN NNNNNNNNNN
15051 NNNNNNNNNN NNNNNNNNNN NNNNNNNNNN NNNNNNNNNN NNNNNNNNNN
15101 NNNNNNNNNN NNNNNNNNNN NNNNNNNNNN NNNNNNNNNN NNNNNNNNNN
15151 NNNNNNNNNN NNNNNNNNNN NNNNNNNNNN NNNNNNNNNN NNNNNNNNNN
15201 NNNNNNNNNN NNNNNNNNNN NNNNNNNNNN NNNNNNNNNN NNNNNNNNNN
15251 NNNNNNNNNN NNNNNNNNNN NNNNNNNNNN NNNNNNNNNN NNNNNNNNNN
15301 NNNNNNNNNN NNNNNNNNNN NNNNNNNNNN NNNNNNNNNN NNNNNNNNNN
15351 NNNNNNNNNN NNNNNNNNNN NNNNNNNNNN NNNNNNNNNN NNNNNNNNNN
15401 NNNNNNNNNN NNNNNNNNNN NNNNNNNNNN NNNNNNNNNN NNNNNNNNNN
15451 NNNNNNNNNN NNNNNNNNNN NNNNNNNNNN NNNNNNNNNN NNNNNNNNNN
15501 NNNNNNNNNN NNNNNNNNNN NNNNNNNNNN NNNNNNNNNN NNNNNNNNNN
15551 NNNNNNNNNN NNNNNNNNNN NNNNNNNNNN NNNNNNNNNN NNNNNNNNNN
15601 NNNNNNNNNN NNNNNNNNNN NNNNNNNNNN NNNNNNNNNN NNNNNNNNNN
15651 NNNNNNNNNN NNNNNNNNNN NNNNNNNNNN NNNNNNNNNN NNNNNNNNNN
15701 NNNNNNNNNN NNNNNNNNNN NNNNNNNNNN NNNNNNNNNN NNNNNNNNNN
```

FIGURE 3, page 5 of 25

```
15751 NNNNNNNNNN NNNNNNNNNN NNNNNNNNNN NNNNNNNNNN NNNNNNNNNN
15801 NNNNNNNNNN NNNNNNNNNN NNNNNNNNNN NNNNNNNNNN NNNNNNNNNN
15851 NNNNNNNNNN NNNNNNNNNN NNNNNNNNNN NNNNNNNNNN NNNNNNNNNN
15901 NNNNNNNNNN NNNNNNNNNN NNNNNNNNNN NNNNNNNNNN NNNNNNNNNN
15951 NNNNNNNNNN NNNNNNNNNN NNNNNNNNNN NNNNNNNNNN NNNNNNNNNN
16001 NNNNNNNNNN NNNNNNNNNN NNNNNNNNNN NNNNNNNNNN NNNNNNNNNN
16051 NNNNNNNNNN NNNNNNNNNN NNNNNNNNNN NNNNNNNNNN NNNNNNNNNN
16101 NNNNNNNNNN NNNNNNNNNN NNNNNNNNNN NNNNNNNNNN NNNNNNNNNN
16151 NNNNNNNNNN NNNNNNNNNN NNNNNNNNNN NNNNNNNNNN NNNNNNNNNN
16201 NNNNNNNNNN NNNNNNNNNN NNNNNNNNNN NNNNNNNNNN NNNNNNNNNN
16251 NNNNNNNNNN NNNNNNNNNN NNNNNNNNNN NNNNNNNNNN NNNNNNNNNN
16301 NNNNNNNNNN NNNNNNNNNN NNNNNNNNNN NNNNNNNNNN NNNNNNNNNN
16351 NNNNNNNNNN NNNNNNNNNN NNNNNNNNNN NNNNNNNNNN NNNNNNNNNN
16401 NNNNNNNNNN NNNNNNNNNN NNNNNNNNNN NNNNNNNNNN NNNNNNNNNN
16451 NNNNNNNNNN NNNNNNNNNN NNNNNNNNNN NNNNNNNNNN NNNNNNNNNN
16501 NNNNNNNNNN NNNNNNNNNN NNNNNNNNNN NNNNNNNNNN NNNNNNNNNN
16551 NNNNNNNNNN NNNNNNNNNN NNNNNNNNNN NNNNNNNNNN NNNNNNNNNN
16601 NNNNNNNNNN NNNNNNNNNN NNNNNNNNNN NNNNNNNNNN NNNNNNNNNN
16651 NNNNNNNNNN NNNNNNNNNN NNNNNNNNNN NNNNNNNNNN NNNNNNNNNN
16701 NNNNNNNNNN NNNNNNNNNN NNNNNNNNNN NNNNNNNNNN NNNNNNNNNN
16751 NNNNNNNNNN NNNNNNNNNN NNNNNNNNNN NNNNNNNNNN NNNNNNNNNN
16801 NNNNNNNNNN NNNNNNNNNN NNNNNNNNNN NNNNNNNNNN NNNNNNNNNN
16851 NNNNNNNNNN NNNNNNNNNN NNNNNNNNNN NNNNNNNNNN NNNNNNNNNN
16901 NNNNNNNNNN NNNNNNNNNN NNNNNNNNNN NNNNNNNNNN NNNNNNNNNN
16951 NNNNNNNNNN NNNNNNNNNN NNNNNNNNNN NNNNNNNNNN NNNNNNNNNN
17001 NNNNNNNNNN NNNNNNNNNN NNNNNNNNNN NNNNNNNNNN NNNNNNNNNN
17051 NNNNNNNNNN NNNNNNNNNN NNNNNNNNNN NNNNNNNNNN NNNNNNNNNN
17101 NNNNNNNNNN NNNNNNNNNN NNNNNNNNNN NNNNNNNNNN NNNNNNNNNN
17151 NNNNNNNNNN NNNNNNNNNN NNNNNNNNNN NNNNNNNNNN NNNNNNNNNN
17201 NNNNNNNNNN NNNNNNNNNN NNNNNNNNNN NNNNNNNNNN NNNNNNNNNN
17251 NNNNNNNNNN NNNNNNNNNN NNNNNNNNNN NNNNNNNNNN NNNNNNNNNN
17301 NNNNNNNNNN NNNNNNNNNN NNNNNNNNNN NNNNNNNNNN NNNNNNNNNN
17351 NNNNNNNNNN NNNNNNNNNN NNNNNNNNNN NNNNNNNNNN NNNNNNNNNN
17401 NNNNNNNNNN NNNNNNNNNN NNNNNNNNNN NNNNNNNNNN NNNNNNNNNN
17451 NNNNNNNNNN NNNNNNNNNN NNNNNNNNNN NNNNNNNNNN NNNNNNNNNN
17501 NNNNNNNNNN NNNNNNNNNN NNNNNNNNNN NNNNNNNNNN NNNNNNNNNN
17551 NNNNNNNNGGT GGAGAGTTCT GTAGATGTCT GTTAGGTCTG CTTGGTCCAG
17601 AGCTGAGTTC AAGTCCTGGA TATCCTTGTT AACCTTTTGT CTTGTTGATC
17651 TATCTAATAT TGACAGTGGG ATGTTAGACT CGCACACAAT AATAATGAGA
17701 GACTTTAAGT CTTTTTCTAG GTCTCTAAGG ACTTGCTTTA TGAATCTGGG
17751 TGCTCCTGTA TTGGGTACAT ATATGTTTAA GATAGTTAGC TCTTCTTGTT
17801 GAATTGATCC CTTTACCATT ATGTAGTGGC CTTCTTTGTC TCTTTTGATC
17851 TTAGTTGGTT TAAAGTCTGT TTTATTAGAG ACTAGGATTG CATTCCCTGC
17901 TTTTTTTTTT CGCTTGGTAG ATCTTCCTCC AGCTGTTTAT TTGAGCCTA
17951 TGTGCATCTC TGCACGTGAG ACGGGTCTCC TGAATACAGC ACAGTGACGG
18001 GCCTTGACTG TTTATCCAAT TTGCCAGTCT GCGTCTTTTA ACTGGGGCAT
18051 TTAGCCCACT TATATTTAAG GTTAATATTG TTATGTTTGA ATTTGATCTG
18101 TCATTATGAT GTTTGCTGGT TATTTTGCCC ATTAATTGAT GCAGTTCTT
18151 CCTAGCCTCG ATGGTCTTTA CAATTTGGCA TGTTTTTGCA GTGGCTGGTA
18201 CCAGTTGTTC CTTTCCATTT TTACTGCTTC CTTCAGGAGC TCTTTTAGGG
18251 CAGGCCTGGT GGTGACAAAA TCTCTGAGCA TTTGCTTGTC TGTGAAGGAT
18301 TTTATTTCTC CTTCACTTGT GAAACTTAGT TTGGCTGGTT ATGAGATTCT
18351 GGGTTGAAAA TTCTTTAAGA ATGCTGAATA TTGGCCCCCA CTCTCTTCTG
18401 GCTTGTAGGG TTTCTGCTGA GAGATCTGCT GTTAGTCTGA TGGGCTTCCC
18451 TTTGTGGGTA ACCCGACCTT TCTCTCTGGC AGCCCTTAAC ATTTTTTCCT
18501 TCATTTCAAC GTTGGTGAAT CTGACAATTA CGTATCTTGG GATTGCGCTT
18551 CTCGAGGAAT GTCTTTGTGG TGTTCTCTGT ATTTCCTGAA TTTGAATGTT
18601 GACCTGCCTT GCTAGGTTGG GGAAGTTCTC CTGGATAATA TACTGAAGAG
18651 TGTTTTGTAA CTTGGTTCCA TTCTGTCTAT CACTTTCAGG TACAACAATC
18701 ATAGCATTGG TCTTTTCACA TAGTCGCATA TTTATTGAAG CCTTTGTTCA
18751 TTTCTTTTCA TTCTTTTTTC TCTAATCTTG TCTTCTTGCT TTATTTCATT
18801 AATTTGATCT TCGATCACTG ATATCCTTTC TTCTGCTTGA TCGAATCGGC
18851 TATTGAAGCT TGTTTATGCT TTGTGAAATT CTTGTACTTT GGTTTTCAGC
```

```
18901 TCCATCAGGT CATTTAAGCT CTTCTCTACA CTGGTTATTC TAGTTAGCCA
18951 TTTGTCCAAC CTTTTCTCAA GGTTTTAAGT TTCCTTGCGA TGGGTCAGAA
19001 CGTGCTGCTT TAGCTTGGAG AAGTTTGTTA TTACCAACCT TCTGAAGCCT
19051 ACTTCTGTCA ACTCGTTAAA CTCATTGTCC ATCCAGTTTT GTTCCTTTGC
19101 TGGTGAGGAG TTACGTTCCT TTGGAGGAGA AGAGGCGTTC TGTTTTTGGA
19151 ATTTTCAGCC TTTCTGCTGT GGTTTCTCCC CATCTTTGTG GTTTTATCTA
19201 CCTTTGGTCT TTGATTTTGG TGACGTACAG ATGGGTTTTG GTGTGGGTGT
19251 CCTTTTTGTT GATATTGATC CTATTCCTTT GTTTGTTAGT TTTCCTTCTA
19301 ACAGAGGCCC GTCAGCTGCA GGTCTGTTGG AGTTGCTGGA GGTCCACTCT
19351 AGACCCTGTT TACCTGGGTA TCACCAGTGG AGGCTGCAGA ACAGCAAATA
19401 TCGCGGCCTG ATCCTTCCTC TGGAAGCTTC GTCCAAGAAG GACACCCACC
19451 TATATGAGGT GTCTGTCGGC CCCTACTGGG AGGTGTCTCC TCCCAGTCAG
19501 GCTACATGGG GCTCAGGGAC CCACTTGAGG AGGCAGTCTG TCCGTTACTG
19551 GAGTTCAAAT GCCGAGCTGG GAGAACCACT GCTCTCTTCA GAGCTGTCAG
19601 GCAGGGATGT TTAAATCTGC AGAAGCCGTC TGCTGCCTTT TGTTTAGATA
19651 TGCCCTGCCC CCAGAGATGC AATCTAGAGA GGCAGTAGGC CTTGCGGTGG
19701 GCTCCACCCA GTTCAAGCTT CCTTGCTGCT TTGTTTACAC TGTGAGCATA
19751 GAAGTGCGTA CTGAAGCCTC AGCAATGGCG GGGAGGCGCT TCCCCTCACC
19801 AAGCTCCAGC ATCCCAGCTT GATCTCAGAC TGCTTGGCTA GCAGCAAGCA
19851 AGGTTCCATG GGCATGGGAC CCCCGAGCC AGGCACTGGA GGCAATCACC
19901 TGCTCTGCCA GTTGCGAAGA CTGGGAAAAG CACAGTATTT GGGCAGAGTA
19951 TACTGTTCCT CCAGGTACAG TCACTCACGC CTTTCCTTGG CTAGGAAAGG
20001 GAAATCCCCT GACCCCTTGC ACTTCCTGGA TGAGGTGACG TCCTGCCCTG
20051 CTTTGGCTCA CCCTCCATGG GCTGCACCCA CTGTCCAACC AGTGCCAATG
20101 AGATGAACCA GGTACCTCAG TTGGAAATGC AGAAATCACC CATCTTCTGC
20151 ATCGATCTTG CTGGGAGCTG TAGACCAGAG CTGTTCCTAC TGGGGCATCT
20201 TGGAAGCAAC TCTGGGTCTG AGTTTCTGTT TGTTGCCCTG ATGTATATCC
20251 CCAGTGCCTA GAATGATACT TGTTACATAG GAAGTGCTTG ATCCATGTTT
20301 GCACAAATGA ATCTTTCTCA TAATGAGGTT TCTCTAAACA AGCTGTTCTC
20351 CCAAAAACTT ACACCCAGCT TTATGTTGAA GCATCTCATT ATACATTGGA
20401 AAGATGAAAT GTGTAGTGAG ACTTGAATC TTCTTTTGAA TCTAGAAACA
20451 TTAGCATTTT TAGACCATTC TATTTTAATA TTTATGAAAT TTATGAAATA
20501 ATAAGAAACA TGAGGCCGGG CTCAGTGGCT TATGCCTGTA ATCCCAGCAG
20551 TTTGGGAGGC CAGGGCTAGT GGATCATGAG GTCAGGAATT TGAGACCAGC
20601 TTGGCCAACA TGGTGAAACC CCACTTCTAC TAAAAATATA AAATTAGCT
20651 GGGCGTGGTG GTGCATGCCT GTAATGCCAG CTCCTGGAGA GGCTGAGGCA
20701 GGAGAATCAT TTGAACCTGG GAGGCGGAGT TTGCAGTGAG CTGAGATCGT
20751 GCCATTGCAC TCCAGCCTGG GCAACAGG GAGACTCCAT CTCAAAACA
20801 AAAACAAAAA CAAAAAAAAT GTGTGACCTA AATTAGGCTT ATAGATGAAC
20851 CATTGCAGTC ATGATTAATT CCGCCATTGT TTGCCTTGTG ATCTTTGGTG
20901 CCATGTCTGT ACATATTTCA TGATTTCTGT GTTTTTACGG TTTCCATTTC
20951 AGATCTCCCT TGAGTTTAGA AATCTGGCTG AGAAATACCA AACAGTGATT
21001 GCCGACATTT GCCGGAGAAT GGGCATTGGG ATGGCAGAGT TTTTGGATAA
21051 GCATGTGACC TCTGAACAGG AGTGGGACAA GGTTAGTCTC ATAAAACAGT
21101 GTCTGTGTGT GATGTATTAG ACAGAGCTGG CAGTCCTCAT AGTGAAGCTC
21151 AGAACAAGAA AAGTTGTCCA GTATTTCAG CCCCTCTGGT TTTACAATTC
21201 ATCTGTTTAG GTTGAATGTC TCATCATAAA CAGTTTATTC CAGAGTTAAT
21251 TCCAAACCAG CAGCTATGTA GGATATCAGC CAGGCTAGGA GTAGGGTACT
21301 GGAGAGAAGT GCTTATCTAG ACAAAGGGAT GTAATTGACC ATGAAGATTA
21351 AAACTACACA TCAAAACATA AGGTAGGGTT AGGAGTCTTG CCTATTTTTC
21401 ATAGGAATGG TGTTTGTGAG ACTTACTCAT CACTTCTGTG GAAGTAAAGA
21451 CATTTTATTT ATTTATTTTA AAGCCAGTCA GATTTAGCAG GCAGAGACAT
21501 TTCAGACATC TAAAGTGTTG ATGTATTTCA TACCTTTAAC TGTGCTTAAA
21551 TTAGGATCTC CGAAAAGATG CTGCTACATG GTCACTACGT TAGTGTAGGT
21601 CCAAGGTCTT GGGCCTCTTA ATTTTTCAAA CCTCAAAACT TGACAGCAGT
21651 TATCTTTGGA ACTGCTGATT TGTGCTTCCT AAGTTAACAG CATACAATGA
21701 CTGCTAGAAA TCAATTTCTG CATTTAAGGT GAAGTTAGCC GGGTACTATG
21751 GTTTACCTGT AATCTCAGCA CTTTGGGAGG CTGAGGTGGG AGGATCATTT
21801 GAGCCCAGGA GTTAGACACA AGCCTAAGCA ACATAGCGAG ACCCCGTCTT
21851 TCAAAAAATT AAAAAATGAG CAGGGAATTG GTGGCATGTG CCTGTGGTCC
21901 CCAGCTACTC TGGAGGCTGA GGTGTGGGAG GATTGCTTGA GCCCAAGAGT
21951 TGAAGGTTGC AGTGAGCCAT GATTGTGCCA CTGCACTCCA ACGTGGGTGA
22001 CAGAGCAAGA CACCTACTGA AAGAAAATAA AGTTGAAGTT AAAACTTCTG
```

```
22051 GCCAAGAACC AGCACTGGTT ATGATAGTAA CTCATTTTCT GTTGTGCAGA
22101 TTTATTCAGG AAACTTAATT TTAGGTTGTT GAATAGAAGT TTTGATCAGA
22151 TAAAATTGAA TTAAAAAAAA TTTTTTTTGA GACAGGGTCT TGCTGTTATC
22201 CAGGCTGGTG TGTAGTGGTG TGATCACGGC TCCCCGCAGC CTCAACCTCC
22251 TGGGCTCAGG TGATCCTCCC ACCTCAGCCT ACCGAGTAGC TGTAACTACA
22301 GTGCATGACA CCATACCAGG CTCATTTTTG TACATTTTTT GTAGAGAGAG
22351 GGTTTTGCCA TGTTGCCCAG GCTAGTCTCA AACTCCTGGC ATCAAACAGT
22401 CCTCCCACTC TGGCCTCTCA AATGTTGGGA TTACAGGCAT GACCAGCCAA
22451 TTATTTCAAG GAGTTATTTT TTTTCTTCTA CTTTGGGGGA AGATGAATTA
22501 TATAAGTCTC CATTTTAGGA GTATTTCTAC CAAAAGAACT ATTATCTTCA
22551 AATATATTTT TGGATAGTAC TATAGATATA CTAATTTTTT TTTAAATTTC
22601 TAGTAATTCT TTTGAAGATT TTGTATAGCT GTCCAAAGCC AATTTCTGTC
22651 TACCTAATTT CAGCAAGATT TCACTCTTTT CATGTTACTT TTGTCCCAGA
22701 ACAAATTTCA AGTGCTTTCT CTTCACCTGT GCATTCTTCC CCCTGATTAG
22751 TCTCTGGCTT TGTATTACTT TCAGTCAGAG ACGACTTTTT TTTTTTGAGA
22801 CAGGGTCTCA CTCTGTCACC CAGACTGGAA TGCAGTGGCA CAGACAAGGC
22851 AGCCTTGACC TTCTGGGCTC AAGCAATCTT CCTTGCCCTC AGCCTCCTGA
22901 GTAACTGGGA CCACAGGCAC GTTGCCACCA TGCCTGGCTA ATTTATTTTA
22951 ATTTTTATTA TTTTTGAGAC AGGGTATTGC TCTGTCACCC AGGCTGGAGT
23001 GTAGTGGCAT GATCAAGGCT CACTGCAGCC TTCACCTCCT GTGCTCAAGC
23051 AGTCCTCTCA CCTCAGCCTC CCCATTAGCT GGGACTATAG GTCCACACCA
23101 CTACACCAGG CTAATTTTTG TAATTTTTTG GTAGAGACAG GGTTTCATCG
23151 TGTTGCCTAG GCTGGTCTTG AGCTCCTGGG CTCAAGCGAT TCACCTGCCT
23201 TAGCCTCCCA GGTGTGAGCC ACTACACTCA GCCTTTTAAA ATTTTTTACA
23251 GAGATGAGGT CTTGCTTTGT TGGCCAGGCT GGTCTAAAAC TCTTGGGCTC
23301 AAGCAGTCCC CTCTCCACAG CCTCCCAAAA TTCCGGGATT ACAGGCGTGA
23351 ACTTCGGTCA TTTCCTAACT TTTACCCTTC CTAATGACAC TCCAGAGCTT
23401 ACCTTCTTTA CTTTTGCTTC TTAAGTTAAC TAATAGACAA TTATTGTATG
23451 TGGATATTGC ATTAAGTTGT CTTAGGATAC CCTTTTCAGA GGAGGACAGC
23501 TTTTGACAAA TTGCTGTCGC GGAAAAAAAA AGTATTTGGC AATTAAGAGT
23551 TGCATTTACT GAAATCTCTG TTGAGAGAGG GGAAGTTACG TTGTCTCTAA
23601 AAGAAAAACT AAAAAGAAAA GGGGAAGTTT TAGCAAAGTT GTTAAAGCCT
23651 GACACTTAAG TCATACTACC TAGTTTTGAA CTCTTAGCCC CTGCCACAGA
23701 CACGGCAGCC CCTTGAACCT TCCTGGGTTC AAGCGAGCCT CCTACTTCAG
23751 CCCCCTGAGT AACTGGGACC ACTGGCCTGT GTCACTGTGC CTGGCTAATT
23801 TTTTTTTTTT CCTCACATGG GCAATGTTGG GCAAGTTAAA TCGACTTCTT
23851 TGTGCCTCAG TTTCCTCATC TGAAATGGAG ATCATACTGC TATGTACCTG
23901 ATACAATGTT TGTGAGGATT GAATGTGCAG AGTTCTTTTT TTCTGTTGTT
23951 GTTGTTTTGA GACGGAGTCT CACTCTGNNN NNNNNNNNNN NNNNNNNNNN
24001 NNNNNNNNNN NNNNNNNNNN NNNNNNNNNN NNNNNNNNNN NNNNNNNNNN
24051 NNNNNNNNNN NNNNNNNNNN NNNNNNNNNN NNNNNNNNNA TCTCGTGATC
24101 CGCCCGTCTC AGCTTCCCAA AGTGCTGGGA TTACAGGCAT GAGCCATCGT
24151 GCCCGGCTGA ATGTGCAGAG TTCTTAAAAC CGTGTCAAGA ACATAAAATA
24201 GTTATTTGTT CTTTCATATA ATGATGATTT TGAGGGCCTG CGGATCTTGA
24251 CATGTTATCA GATTGGTCAA AAAAAGATTA AACCATAGTT GGTATTGTCC
24301 TAGTTCCTGT TACCAGAATA TTCCATCTTT CATCGTTGCC TTCTCTCATA
24351 GTTTTATGTA TCAAAAAGTT TATTGTAAAG CTAGGCCGGG CACGGTGTCT
24401 TGGGCTGGTA ATCCCAGCAC TTTGGGAGGC CAAGGCTGGC AGATCAGTTG
24451 AGGTCAGGAG TTCGAGACCA GCGTGGCCAA CATGGTGAAA CCCCGTCTCT
24501 ACTAAAAATA AAAAATTAGC TGGATGTGGT GGTGGGTGCT TTAATTCCAG
24551 CTACTCAGGA AGCTGAGGCA GGAGAATCAC TTGAACCCAA GAGGCAGAGG
24601 TTGCAGTGAG TTGAGATTGT GCCACTGCAC TCCAGCCCAG GGACAAAGT
24651 GAGACTTGAT CTCAAAAAAA AAAAAAAAAA AAAGTTATTG TAAAGCTAGA
24701 CACGGTGGTA TTTGCCTACA ATCCCAGCTG TTCGGGAAGC TGAGGCAGAA
24751 AGATTGCTTG GGTCCAGTAG TTTGAGTCTA ACGTGGGCAA ATATATGAGA
24801 CTCCATCTCA AAAAAAAAAA TAAAAAATAA AATAAAAAA ATGTTTACTA
24851 GTTTTTTTCA GTAGCCTTTT ATTATAGTAG CAGTACATGT GTATTGTAGA
24901 AATTTGGAAA ATACAAGTGA AAAATAAAAA CATCAAATTC CGTCAGCCA
24951 GAGACTGCTG TGAAATGTTT TGAGCACATC CTTCTTGAAT GTTTTTTAAA
25001 TCCTGGTATG TATATTTGTA TTTTAAAATC AAAATGCATT CTTACCCATT
25051 CTCTTTTGAA CCTGCTTTTT TGTAGCTAAT GATCTCTAGT GTGTCCATTT
25101 CAGTAAAAAT TCCATTATTA AAGTGCTTTA AAAATCGTCT CTTACAGTAC
25151 TGCCACTATG TTGCTGGGCT GGTCGGAATT GGCCTTTCCC GTCTTTTCTC
```

FIGURE 3, page 8 of 25

```
25201 AGCCTCAGAG TTTGAAGACC CCTTAGTTGG TGAAGATACA GAACGTGCCA
25251 ACTCTATGGG CCTGTTCTG CAGAAAACAA ACATCATCCG TGACTATCTG
25301 GAAGACCAGC AAGGAGGAAG AGAGTTCTGG CCTCAAGAGG TAACAGATTC
25351 AGGGTATTTT GGGGGAAAAT AACTTTAGAC ATTCTCTGAA AAATCCTTTA
25401 ACTCTTGTGG TTGCGGGTGA CAGAAAAACA AGCCAGGCCT CCCCCAGGCA
25451 GCATAAGGGG ATGTGGAAAA TAGGATAGAT TGACATGAGT TTGCTTCAGG
25501 TAGACTGGCT GACTCCCAGG ATTCACACCA CGTAATCAGT ATATTCAAGC
25551 CTTGCTGTCC TTGATTTCTT TCAGACGGTC TTTCTCCAAG TGGTGGATAT
25601 GGTAACAACC CACGTGCACT AGCTTAACAA AAAGTTCTTA GGAATGGCTT
25651 TGTTCGGCCT GGCGCAGTGG CTCATGCCTG TAATCCCAAC AGTTTGAGAG
25701 GCCAAGGTGG GCGGATCACC TGAGGCCAGG AGTTCGAGAC CAGCCTGGCC
25751 AACATAGTGA AACCCCGTGT TTACTAAAAA ATACAAAAAT TAGCCGGGCG
25801 TGGTGGCAAG GGCTTGTAAT CCCAGCTACC TGGGAGGCTG AGGCAGGAGA
25851 ATCGCTTGAA CCCAGGAAGC AGAGATTGCG GTGAGCTCAG ATTGTGCCAC
25901 TGCACTCCAG CCTGGGCGAC AGAGTGAGAC TCCCTCTCAA AAGAAGAGGA
25951 AGGGCTTGGT TCTTCTGCTC AGCCCTGAAT CAGTTACTGT TGCTACACAG
26001 CTGAGTTCTC TGGCCTCACC TGGATTACGT CTACACAGTA CACACAGAAT
26051 GGATTTCCCC CAAAGAAAGA ATTCTGCGGC AGGAAGGGGA AAGGGATGGC
26101 AGGTAGACAA AAACTCCAGG TGTCTGTAAT AAGGGACAGG GTCGATCTTT
26151 AATTAAAACA TGGACAGGGA ACAGAAAGCT TTTGATACTG ATTTGTTCA
26201 GAAGGAAAGT AGAAAATTTT ATGACTGTTC CCTGAATTTA TTCCAGCATT
26251 TACCTTTTGC TTTCCATAAA AGTGTTTCCT GCAGCCAAGT ACTTTAAAGT
26301 TTTAAAAAGA CGGGTGAGGC TAAGTGTGGT GTCTCATACT TATAATCCCA
26351 GTGCTGAGGC CAGGAGTTCA AGACCAGCCT GAGCAACACA GCAAGATACC
26401 ATCTCTATAA AAAATTGTTA GAAAATGATT CTGCTGAAAG AGCAAAAATA
26451 AAATTAAAAG AAAGTAGAAA AAATAAAACT AAATTTAAAA GATTAACTGG
26501 GCATGTTGGC ATGCACCTGT ATTCCTAGGT ATTCGGGAGG CTAAGGCACA
26551 AGGATCCCTT GAGCGCAGGA GCTCAAGGTT GGATTGAGTT GTAATCACAC
26601 CACTGCACTC CAGCCTCGGT GGCACAATGA AACTGTCTCA AGAAAAAAAA
26651 AAAGTGACAG AGGGAAACAA TATTTGCAAT TCATAGAGCA GATACAGGGT
26701 TCATATTCCT AATATTAAAA AAACTTCTA AAAGTTAAGA AAAAGGCCAA
26751 CTGCCCCACA GAAAATGGG CAAGGAGATA AGAACAAGAT TGTTCACAGG
26801 AAGAGACACA CAGATGATTA TTAAAAATCT GAAAAGATGC TGAGTCTTAC
26851 TCCTAAGAAA AATTCACATT TAAACTACTC TGGGGGCTGG GCAAGGTGGC
26901 TCACGCCTGT AATCTCAACA CTGGGAGACC AAGGCAGGAA GATCACTGAA
26951 GCCAGGGTAT CGAGACCAGC CTGGACAACG TAGTGAGACC TTATCTCTTA
27001 AAACAAAACA AACAAAACA AAACAGTAAAA AACAGTAAA ATTGGCCGGG
27051 CACAGTGACT CCTGCCTATA ATCCCAGCAC TTTGGGAAGC CCAGGTGAGT
27101 GGATCACTTG AGGTCAGGTG TTTGAGAACA GCCTGGCCAA CATGGCAAAA
27151 TTCCGTCTCT ACTAAAATTA CAAAAATTAG CCAAGTGTGG TGGCATACGC
27201 TGGTAGGGCC AGCTACTTGG GAGGCTGATG TGAGACTCCA TTTAAAAAAA
27251 AAAAATCAAA AATTAGCTGG GTATAGTGGC ACACCCCTAT AGTTCTCGCT
27301 CCTTGGGAGG TTGAGGCAGG AGGATTGCCT GAGCCCAGGA GTTCAAGGCT
27351 GCAGTGAACC ATGATCACAC CACTGCATTC TAGCAGCCTG GGAGACAGAG
27401 CAAAACCCTT GTCTCAAAAC AAACAAACAA CAACAAAAAC AAAAACACT
27451 TCCCTCAGCT CAGACATGGC CTTTTAAGTT TCCTAGGTGA CTCGTGTGCA
27501 GCCAGGGTTG AGAAACCACT CTTGTCTTAC CCCTCTTTTG CAGACACAGG
27551 GCTCAGAGAA GGGAAGGGGA TTGTCTGGGG ATGTATAGTG AGGCAGTGGC
27601 TGCCTTGGAA GTGGAGTCTC AGTCTCCCGG CTCCTAGGCC AGCCCCTGAC
27651 CACTGTTCCA TTGTCTCCCA GACAGAACAT CAGCCACGGG CATGTGATGC
27701 ATGAGCGTGA GCCACACCAT CTTGCACACA CAGGAGCAGA GCCCTGCTCT
27751 TCTCATTCAC TTACTTTATC TGTAAAATAG CATCATTTCT ACCACACGGT
27801 GGTGGTGTGA ATAAAATGAG ATGAACTTCT AGCATAGAGT GCTTAGTAAA
27851 GGTTCTGGAC ATTTCGTAGT AGTTGAATCA TGCCAAATGT GGTCCTAGGT
27901 GATTGGCTTC TTTTGCTAGC ATGTTTTCAG GGCTCCTCCA TGCTGGGGCA
27951 TTGCATCACT GCTTTATTCC TTTTTATCGC CTAGTATTAT TCCACTGTGT
28001 GGATAGACCA CATTTATCCA TTCATCAGTT GGAGGATATT TGGGTTCTTC
28051 CCATTTTTTT TGGCTATGGT GAATAGTACT GTGTACATTT GCATATAAGG
28101 TTTTGTGTAG ATGTGTGTTT TCCTTTTTCT TGGGTCTATG CTGAGAAGTG
28151 GAATTGCTGG TTCATACAGC AGCTCGAACC TTGTGAGGAG CTGCCAGACG
28201 CTTTTCCAAG GTCGCTCCAC CATTTTACAT TCCCGTCAGC AGTGTGAGAG
28251 TCCCAGTTTC ACCAGCACTT GTTGTTATCT CTTTTTAACT GTATGTATAT
28301 ATACTTAACA TTTTATTTAT AATAAATGTA CATAATAGAG AATTTGCCAT
```

FIGURE 3, page 9 of 25

```
28351 TTTAACTATT TTTAAGTCTA TTATTCAGTG GCATTAAGTA CATTAATGAT
28401 GTTATATAAC CATCAACACT ATGTTCCAG AACTTTCGCT AGCTTCAGAG
28451 AATCCTCTAA ATAATATCAT TAAAAATCAT CAAGCCGAAT CCCACTGTTA
28501 GAATTAAAGG TTTTATTTCA CTTTCAAGTT ATCAGGATCC AGGGAGGTGT
28551 AATACACTTA GAGGATAGAC TCAGCTCATT TCCCAGCTAT GCCTTTCAGC
28601 AGCATTCTTA CCAGAGTAGG AATATAATGT TAGTCATTAT TTAGAGGCCT
28651 GGCCATCTTG AGAAGGTTTA CTGTTTAGTC TGCAGTACAA TTATAACTGT
28701 TTTTGTATAT TGGGTTATTT TTTTCAGAAG TAGGCCAGTA GCTCTAACAG
28751 GAGCCTCTTT AGCCTGAATT CGTCCAAGTA GTGCAGTGTT GCACTAGTTG
28801 TCCCTCGGGA CATGCTCCCC AATACGTAAC TCACTTCCAG GTTGCAACTG
28851 GACACTTACT GGTAGTCAGA AATAGCTATT GCATGGAGCT TAAAATGAAC
28901 TTGATCTTCG TGAAAGATGA GTCTGCAGCT AAGAGACTTT ACTGTATATC
28951 ATAGTGTTTT TTTTTGTTTT GTTTTGTTTT TGTTTTGTG ACGGAGTCTC
29001 ACTCTTTCAC CCAGGCTGGA GTGCAATGGC GAGATCTTGA CTCACTGCAA
29051 CCTCCGCCCC CTAGGTTCAA GCAATTCTTC TGTCTCACCC TCCTGAGTAG
29101 CTGGGATTAC AGGCGCCTGC CACCGTACCC GGCTAGTTTT TGTATTTTTA
29151 GTAGACACAG GGTTTCACCA CCTTGGCCAG GCTGGTCTTG AACTCCTGAC
29201 CTCGTGATCC ACCCTCCTCG GCCTCCCAAA GTGCTGGGAT TACAGGCGTG
29251 AGCCACGGCG CCCAGCCTGT ATCATAGTTC TTATGCACAA AGACCCTTTA
29301 ATATTGTTTG TAAATTCTCC CCTATGCACA CGCTGACCTG TTCCTTAATC
29351 TTCTTATCTG TCTAGGTTTG GAGCAGGTAT GTTAAGAAGT TAGGGGATTT
29401 TGCTAAGCCG GAGAATATTG ACTTGGCCGT GCAGTGCCTG AATGAACTTA
29451 TAACCAATGC ACTGCACCAC ATCCCAGATG TCATCACCTA CCTTTCGAGA
29501 CTCAGAAACC AGAGTGTGTT TAACTTCTGT GCTATTCCAC AGGTAGGGAA
29551 CGGGGCTCCT CTGGGTGGAT ACGGGGCTAA AGGGAGTGGG GTAGGAGTAA
29601 GGGTGGATTT TGCTGTGCTA TATTCAAGGA TATGATTCCT TAAAAAGACG
29651 ATGACTCCAG TTTATTACGC TGGGAGTTTC ATAGCACCCG CCTTTGCTTC
29701 CAGCCACCAA ACTCAGCTCA GCCTTGAGGT TAAGCCTGCT CCTTTTCAGA
29751 ACCTTCTTTC CGGATTTACT ATTTTCTACA GCTATCCTAA ACTAGTTAGG
29801 TTCTTTTCCT CACAGTTAAG TCAAGGTCTT TGGCTTAGAT TTATGGGGAG
29851 TGCTGGGTAA AACCTGGGTG AAGCTGTTAT CATTAAAAAG TCTTCATTAA
29901 GCACCTAATT ACTGCTGTCC TTTTCCTAGA CCCGGCATAA AAAGAACCTG
29951 GTCCGGTAGA CCTAGCCTCT CAGTATGCTA GGAACTTACA CTTTTTAGTT
30001 GCCTTTACCA AGTATTGCAG ATACTACTGC AAATAAGTGA AGAAAGTAAC
30051 AGCATTTAAC TGATTTGGGA ACTTGGTTTG ATCTTGTTCT AATGACCCAC
30101 TTCGAATGGT GGTTGAAAGT AAAATCTGTA TCGCCGTCTT ATGTTTCCAT
30151 TTACCTAGAA ATACTTTACC TTTGAGCACA GGAAATTAAT CCCCTTCTGG
30201 TTGTTCTCCC CCTGGCATTG GTTTTAAATA TATAATGATT ATGTTTGTTG
30251 TAGGAAAAAT AGAAAAACAA CTACAATAGA AAATTCTTCC CATATATTAT
30301 TTTGAAATAC ATATTTCCGA TCCGATAATC CATTGCTCTA GCATGGAAAA
30351 TGTTGGATTT ACTTGTGTTT GCTTTTTCCA AATAAAATGG AACTTTTGTG
30401 GCTACATTAT AGAATTGTTT TAGACTGCTT AATTCTGTGT GTTGTTGAGA
30451 AAGGGAGGAG TGGGGAAGGT AAAAATCTTG ACATACTTTC TTCGTGGGTA
30501 TTTTTTCTTG AGCGATTCCA TCTTAGTTGA TTAGCAGTTA GCAATTGCCC
30551 ATTCAACAGA AGGTTTTCTT ACCTTTTTGT GATAATGATA GCTAACGACA
30601 TCATTTCTTC TTTTTTTCCCT CTCTTCTTGT TGTCTCTAGG TGATGGCCAT
30651 TGCCACTTTG GCTGCCTGTT ATAATAACCA GCAGGTGTTC AAAGGGGCAG
30701 TGAAGATTCG GAAAGGGCAA GCAGTGACCC TGATGATGGA TGCCACCAAT
30751 ATGCCAGCTG TCAAAGCCAT CATATATCAG TATATGGAAG AGGTGGGTTT
30801 TTATTTAACT ACTTGGATAA TTTGTAGCTA CTTTTATGAT TTAGTAATGT
30851 CACTGTTTAA CCAGGTTTGG ATATTAGATG ATCCTAACAA TTCACTATCC
30901 TGTGGCCTAA AGAGACAGGA ATTGATATCC TTTATAAGGA AAAAAGTCTA
30951 TTCACAGGAG CCGAGCAGAT TGCTCACTGC TGTGTAGTAC CCTGGTGAGA
31001 GGAGATAAAT GGAGCAAGGC TGTAGGTTGG AGCCCCTCAG TAGAATCATA
31051 GATTTTGAGC TGCAAGATGA TGCAGGAGGC CAACCAAGCT TCTTGTTGCT
31101 GGTGAGGAAT GTGAGGTTGA AGCTTGTCTG TGCTGATGCA GTGCGTGATT
31151 GAGTGGATCT CTGGCTCCCG TCCATGTGTC CTGACACCCA GTCTGGTACT
31201 TTCATTATGC CACAGGCCTC AATTGAAAAA TCACAGTAGG GAATTTAGGC
31251 CAAGGAAAGC CATCAAGTTG CAATTATTTC CTAAATTTTC TTTGGAAAAT
31301 TTCATTTCAA ATACCAAAAC CATCCTATAA AAAGAAAACT TACCTTCTTA
31351 GGTCAAATCT CTAATATTTG ACTAGGTTCA AAAAGTTTAT TTCTGGCCAG
31401 GCACAGTAGC TTACTCCTGA AATCCCAGCA CTTTGGGAGA CCAAGGTGGG
31451 AGGATCACTT GAGGCCAGGA ATTCAAGACC AGCCCGGGCG ACATAGCAAG
```

FIGURE 3, page 10 of 25

```
31501 ACCCCATTTC TACAAAAAAT TTAAAAATTG TCATGGTGGT GCACGCCTGT
31551 GGTCCCAGCT ACTCAGGAGG CTGAGGCAGG TGGATCACAT GAGCCTGAGA
31601 GGTCGAGGCT ACAGTAAGCT GTGTGATTTC ATCATTGCAC TCTAGCCTGG
31651 GTGATAGAGT GAGACTTTGT CTCAAAAAAA AAAAAAAAAA AAAAAGTCTT
31701 AGAGACCAGA AGTCTCTGTA ATCTCTAATA ATCTCTAGGC CCTAGAGCAG
31751 TGGTTTGTAA ATGGAGGTGA TTTGCTCCCC TCCCCCCAGA GGACATTGGA
31801 CAATGTCTGG AGACATTTTT GATTGTCCTA ACCGGCAGGA ATCGGGTGCT
31851 ACTGGCATCT GGTGAGTAGA GGCCCAGGAT GATGCTGTGA TCCTCAGGTG
31901 TGATCCTGTT GAGAATGAAA CACTGTAGAC TTTATGAAAA CATACAAGAC
31951 CCTCATCATT TTTCCTTTGC CTGAGCTCCC TCCCCAGAGG TTACCTCTGT
32001 TCATGGTTTT GTGCATCCGT CTAGTCCCCC TGTTACGCGT TTACAGGAAT
32051 ATGGTTTGCA ACAGTGTTTT CATCTAAATA GAATTATACA AAATAGCGAT
32101 TTCTGATTTC TCTTGCATAT TGCACATTCT TCTTATACTT CCTCCCTACC
32151 TTTATCTGAC ACAGAAATGC TGTATGTCCA GAACTTCTAT CAGAGGCACC
32201 TATGGAAGTC TAAGGGAAGA CCACATCGCT TTTAAAAACC CTAAAATTTT
32251 GTAGTCACTA GATGAAAATA TTCAGCCAGT GACCCAAAAA ATTGCTACCA
32301 ATGAGACTCT CCATTTTGCC ATGTAGCCAG AACTTACTTT GATCTATGTG
32351 CCTGGGGTAG TGACCAAGTA GGTGGGTAGG AGTAATCTCA GGGAAACTTG
32401 AGGCCCCAGC CTCATGGCTA GGGTCATAAT TTGAACCCAG GTCTGTCTGA
32451 CATCAGAATC CATGATGTTA ACCCCAATTC TAAGGGGTTC AACTACCCTT
32501 TCTAAATGGA ATCCTGCTAT ATTAAGCACT ATTTATTCAT TTTATATAAA
32551 CTAGAAACAT TTTATGTAGT AAGTAGTTGA GAGTGTTTTG GTTTTGCAGT
32601 TTGATCACTA GTTTTAGAAA CCAGTTTTTA AACACTTGT GGCCAATTCC
32651 ATTACTATAT TAAAATTCAG ATTTATTTGG TTTTTCCTTA ACTATTGGGA
32701 TTAAATCCTG GTTGTAATTC ATAGTTTGAG GGCGAGGGTG GGCAGTCTAC
32751 ATTTGGCTGA GCCCTGTTTT TGTGAATAAA TGTTATCAGA ACACAGCCAC
32801 ACCCATTTGC TTCTATGTCT TCTGTGGCTG CTTTTGCAAT GTGACGGCCG
32851 AGTTGAGGAG CTGCAACAGG CGATGACTTG TAAAGCTGAA AATATTTTTT
32901 GGCCCTTGAA TAAGAGGTTG GCTGACTTCT GACTTAGGGC ATCAGTTGTT
32951 CTGTTATCCC AGTAAAACTC AAGGCATTAG GGGAGAAATG TTAATATTAA
33001 TACTTAAGTT GATTTGATTT AGGGAAATCT TTGAAGATTT CTAAGTCTTA
33051 AGCAGTAGAA CCTGTTAATG GTTTTAGTTT CAGCAGTAAG GACATTTTAC
33101 AAGTAAAGTT TTAAATGAAA ACATTTTGTA TGAAGCCACA AGTCGTCTGG
33151 CCTCTTGCTG GTGTCCAGAT ATTAACACTG ATCCTATTTC TCCTTGCTGA
33201 CCAAGTCTGT CCTTTGTAGT AAGAAAGGAA GAAACGTTGA CTCTGTCCGA
33251 TCTCTGGACT TAGTGTTGTA GCGAGCATGC ACCTGGAAGG GACTTGCCAG
33301 AGGACCTCCT CATGCTCTC CAGTGCTTAG TGGGGGCTTG GAGTGCAGCC
33351 CCAGGTCTTC ACGAGCAGTT GGCCACACTG CAGGGCCCTC ACCCCACTCT
33401 GGAGCAGCCT CTGCTTCAAA CCAGCCTGGA TGCTTGTCAG CTGGGGAGAA
33451 GATCAACCTG CTATTTGGG ATAGAAATAA ATGCTCAGCC AAACGGCCAG
33501 AAACCCCCAT TCCCCTCTCT GCCAAAGTGA ATTCCTTGGC AGGGAGAAGC
33551 TTGTTCGTGT CTCTGCACAC TTCCTGTGCC CTCCTGTGT TAAGTCAGAG
33601 AATCATCCGG CTCTTTGAGC CCCAGGTGCC TAGCTGCTCA AGGATGGTCC
33651 CCAGCCAGCA GCTGCCAGGA ATCACCTGGG AGCCCATTAA GACATCCAGC
33701 CCCCACCCAA ACCTATCGAA TCAGAATCTG CCTTTTTTTC CCAAATGATG
33751 TTTTTGCTTT AATGGAAGTT TAGATGTTCA TAGACAAGAG TTTTAAATGA
33801 TGATCAAGCT GATTCCATAT TCGCAGTTGT AAGTAGAACT GCTGAGACGT
33851 GGAAGTACCA CATGGACTCA CAGAGGAGCT GCTGTATGTA GCACAGCATT
33901 GCACAAGAGC TTATTTCAGT CTAGTAAACA TTTATAGGAG CCTGTGTCAT
33951 TTAATCATCA AGCCTCGCAC TGTGGCTCAC ACCTGTAATC CCAAAACTTT
34001 GGGAGGCTGA GGCAGGCAGA TCACTTGAGG TAAGGAGTTC GAGACCAGCC
34051 TGGCCAATAT GGCAAAACCC TGTCTCTACT AAAAATACAA CATTTAGCCA
34101 GGTGTGGTGG TGCACACTTG TCATCCCAGC TATTCGGAGG CCTGAGACAT
34151 GAGCATCGCT TGAACTCGGG AGGTGGAGGT TGTAGTGAGC TGAGATGGCA
34201 CCACTGCACT CCAGCCTGGG CAACAGGGTG AAGGCCCTTT CTCAAACTCC
34251 TCAAGTATTT GGCTTCAACT TTATGCCGGG CATGTAGATG AAAAGTCGGC
34301 TATGACCTGT CCTTGACAAG CAGATGTAAC TCCTTGATTG AGGCTAGTAG
34351 GTTTTTAAGA CCTGAATAAT TGAGTTTGCA GAAACCTACT GTGTGCCTTC
34401 AGGTAAATGG AGAGTGGGGT TTGGTCTAGC AACGAAGCAT CTAGAAGGTC
34451 TCTTTGGCCT TACCGGCTCT GTTTTAGGTA AGTCCACGTC TGAGTACCAG
34501 TGACTGCAGC TCTTCCAGTT GTGCTGTCAT GTTTATATGT TAGAAATGAT
34551 CATCAAAGGA CTCAAAAGTT TTGCCACTAA TTGTATTACC GGGGACTGTC
34601 ACAACCAAGA TTTCTCTTAA TTTATTCACC TTACTTATCT CCTGGAAGGG
```

```
34651 CATATTGAAG TGCTCTTGGA GTTCTCTAAA AGGGTTTTTG TTGGTTGTGT
34701 ATATTCACTT GGGTGCCAGC GATTGATTCC AAATAAGTAA ATCTTTTTTC
34751 CCAAAAGGAT GTAAGATGGC TTATGGTTAT AAGTACAACA GGCTAACAAA
34801 GTACAAGTAG ATGAGAAAGT AAAATGAAGA AATAAAGTCA TAGGAGCCAC
34851 AGAATTAACC CAGGAATGAA TAAGTGTGTA GTTTGGTGCT GATGTTATCA
34901 TCCTTTATTT GTACATTGCT TGTACAGTTG CTCTGAGAAG GTAAGTCTTA
34951 AATTTTCAAA AGTGAAATGT CACCGAGCAT GGTGGCTGAT GCCTCTAATC
35001 TCAGCACTTT GGGAGGCTGA GGCAGGCGGA TCACTTGAGG TCAGGAGTTC
35051 GAAACCAGCC TGACTTATGT GATGAAACCC TGTCTCTACT AAAAAAAAAA
35101 AAAAAAAAAA AAAAAAAAAA AAAAATCCAA AAGTTAGTTG GGCATGGTGG
35151 CAGGTGCCTG TAATCCCAGC TACTTGGGAG GCTGAGGCAG GAGAATCGCA
35201 TGAACCTGGG AAGTGGAGGC TGCAGTGAGC CAAGATTGCA CCACTGCACT
35251 CTAGCCTGGG TGACAGAGCG AGACACCATC TTAAAAAAAA AAAAAAATCT
35301 ACAATATACC AAAACCATTA CTTACCTGAG AAACTATTCT CAGGGTCATT
35351 GTAGTGAATG CCTATTTTAT GGCTTTTGAT GGCATCAGGG CACTCAGGTC
35401 ATTTACAAGA GTAGTGTGTG AGACCCTGTG TGTCACTGCC ACTCATCTTG
35451 GCCTTCGGCC ACTGCTGTAG CAACCAGTTT CCAAGTAGGG CTGGACCTTG
35501 CCTTCTGCTC CAGAGACCTC TCGCTTCCTG CCCTTGGGCT TCTGACGAGC
35551 TGCAGGAACT GCCTGGCACG TGGGTCCCCA CAACCCAGAG GAGGTGAGGG
35601 CCACCTCTCT GCTCCTCAGG GCCACCTTTC ATAAGGCTCC TTGAAGGTCC
35651 CTCAAGATCA AGCCAACTCA ACACATCCTT GATAGGCCTT CCTGCCTTCT
35701 GTTTCACTTC TCCACTCGTT TCCAAATAAA TGGCTGCATG CAAGCTTTTG
35751 CCTCAGGTTC TGCTTTTAGG AGGAAGGCTA AGACAAGCAG TAAAGCAACA
35801 TGGGCAGGCA GAAGGATGAC TTCTAATAGA ATTATCTCAT CACTATATAT
35851 TTTACTTTAT GGATGCTTGT ATTGAAAAGT CTTGGCTGGG TGGAGTGGCT
35901 CACGCCTGTA ATCCCAGCCC TTTGGGAGGC CGAGGTGGGT GGATCACTTG
35951 AGGTCTGGAG TTTGAGACCA GCCTGACCAA CACTGGTAAA ACCTTGTCTC
36001 TATTAAAAAT GCAAAAATTA GCCAGGATG CACGCTTGCT GTGTGCCAGC
36051 ACAGGGCTAG GCTGGAGATA AAAGGTGAG TAAGTAGGTG CGGTGTAGTC
36101 AGGGTGAAAA CTACAGATGG TCCATTTCCA CGTAAGTGGA AAGGTAAAGG
36151 TATGTACAAT AGGGTGGCTC CTGGCTGAAC CTGGAGCTGC AGACAGGTTT
36201 TCTAGAAGGC ATAATCCTGA AGTTGAGACT TGGGGCCTA GGTAGGAGCC
36251 AGTTGAAGGG ACGTGGGAGG CGCATTCCAG AGAGAAGGAG TGGTATGAGA
36301 CTGGAACAGA GGTGTGCAGC AGCATCGCAT GGGCGAAACA ACAGTAGACA
36351 GTTGTTCTTT TGTTTTTGTT TGTTTTTTGA GACAGGGTCT TGTTCTGTCA
36401 TCCAGGCTGG AGTGCAGTGG CATGATCTCG GATCACTGCA ACCTCCACCT
36451 CCCAGGCTCA AGTGATCTTC CCACCCCAGT CCCCAAGTAG CTGGGGGACC
36501 ACAGGTGCAT GCCACGATGC CCGGCTAATT TTTGTACATT TTGTAGAAAC
36551 AGGGTTTTAC TGTGTTGTCC AGGCTGGTCT TAAACGCCTG AGCTTAAGCA
36601 GTCTACATGC CTCAGCCTCC TGAAGTGCTG GGATTCCAAA CATGAGCCAC
36651 TGTGCCTGGC CCGGCAACTG TTACTAGACT ATAGAGAGGG AGGTGGGCAA
36701 GGGCTGGTGA CACTAGACAG GTGCAGTAGG TCTGGACCAT GGGTGGCCTT
36751 GCGCTACACA TTACAGAGCT CAGGCTTTTT TTCTCCAGGT GAGAGGGCTG
36801 GTGCCACTGA GGCATCAAGC AGAGGTTTGA GATCTCCTTG GTGACAGTGT
36851 AGAGCAGACA GGTAGATTTG GAATTTAAG CTTAGACTCA CGTTGGAGAC
36901 TGAGATAGCT CATCTGAGAG GCACTCAGGG CCTAATCTCA GGCAGTAATT
36951 TTAGGGATGT AGGGGAAGAG ATGGATTCTG CACATACTTG GGAGGCTTGT
37001 GGAGGAGTGG GGAGGGAGGC ACAGGGAGGA CTCCAGGGTG GTTCATACGG
37051 CTCCCTGCTT CTGTTCCTGT CCCCCTTTGT CAAGCTGTGG TCTGTACTGC
37101 GTGTTCCATC TTGTTTCTAA GCTGCTTTTG CCCAGTCTTT CCAGCATTTC
37151 CCTTTCGTCA TGTTAGTCTG TGCCTGTCTA CGTGAACTAT GGTGACGTTT
37201 ATTGGGCCTG GCACTGTGAG GTGCTGGGA TGTGAAGATC ATTGTGGCTC
37251 AGCCGCTGCT CTCGAGGGCC TCTGGGTGCA GTATGCACAC CTGTGCCTCC
37301 TGTTTGCTCA GGAAGACAGG CTTTGAGATG AGCTGGGGCT GACATCCCCA
37351 CCTTATCATT GGGATGGCTT TGGGTAAGTT ATGTTCATGT TCTCTGAGCC
37401 TCCCTTTCCT CATTGGTAAA ATGGGTATAA AATACCTGCC AGTGGAGGGT
37451 TGTTGTAAGT AGCCATGGAA AATGTAAAGC ACATAGCACT TACCATTTTT
37501 TCCTGTGTCT TTAACAGATT TATCATAGAA TCCCGACTC AGACCCATCT
37551 TCTAGCAAAA CAAGGCAGAT CATCTCCACC ATCCGGACGC AGAATCTTCC
37601 CAACTGTCAG CTGATTTCCC GAAGCCACTA CTCCCCCATC TACCTGTCGT
37651 TTGTCATGCT TTTGGCTGCC CTGAGCTGGC AGTACCTGAC CACTCTCTCC
37701 CAGGTAACAG AAGACTATGT TCAGACTGGA GAACACTGAT CCCAAATTTG
37751 TCCATAGCTG AAGTCCACCA TAAAGTGGAT TTACTTTTTT TCTTTAAGGA
```

```
37801 TGGATGTTGT GTTCTCTTTA TTTTTTTCCT ACTACTTTAA TCCCTAAAAG
37851 AACGCTGTGT GGCTGGGACC TTTAGGAAAG TGAAATGCAG GTGAGAAGAA
37901 CCTAAACATG AAAGGAAAGG GTGCCTCATC CCAGCAACCT GTCCTTGTGG
37951 GTGATGATCA CTGTGCTGCT TGTGGCTCAT GGCAGAGCAT TCAGTGCCAC
38001 GGTTTAGGTG AAGTCGCTGC ATATGTGACT GTCATGAGAT CCTACTTAGT
38051 ATGATCCTGG CTAGAATGAT AATTAAAAGT ATTTAATTTG AAGCACCATT
38101 TGAATGTTCG TACTAGTAGA AAATGATGTG AATTTTCTTT CTGTTCGGCT
38151 CCTATTTTTC TCATCATTTT GTTTTCTTTA ATTGGGTTGA ATGGAGTAGA
38201 TAGAAATATT TATGGTTTAG GTAACAGTTA GATGTTTCCT AAGAATGCAA
38251 ACTGCCTTTT CCACACAAAG GCTGGGAATA AAATTCTGGG TATTCTCGTA
38301 TTCTCATTTA AAGGAGTTTA GCTTCAGAG AGAAACAGCA GGATTGCTTT
38351 TGACCTTTTA GAAGATTGGT CTCCAGTAAA GGTGGACATT TTTGAGATTT
38401 TTATAATAAA GAATTTAATT GCTCTGCATT TGTCAAGTAC AGTTCGCTTG
38451 AAAGCCTGCC TGACTGTGGA AAAGATGGAG CTCAAGAATG GAGTTGATGG
38501 CCCAGCGTGG TGGCTCATGC CTGTAATCCC AGCACTTTGG GAGGCTGAGG
38551 CGGTCGGATC ACGACATTAG GGGATCGAGA CCATCCTGGC TAACACGGTG
38601 AAACCCCGT CTCTACTAAA AAAAAAAAAA ATTAGCCAGG CGTGGTGGCG
38651 GGTGCCTGTA GTTCCAGCTA CTCGGGAGGC TGAGGCAGGA GAATGGCTTA
38701 AACCCGGGAG GCGGAGCTTG CAGTGAGCTC AGATCGCGCC ACTGCACTAC
38751 CAGTCTGGGC AACAGAGCGA GACTCCATCT CAAAAAAAGG AAAAAATTGT
38801 AAAAAAAAAA AAAAAAAAAN NNNNNNNNNN NNNNNNNNNN NNNNNNNNNN
38851 NNNNNNNNNN NNNNNNNNNN NNNNNNNNNN NNNNNNNNNN NNNNNNNNNN
38901 NNNNNNNNNN NNNNNNNNNN NNNNNNNNNN NNNNNNNNNN NNNNNNNNNN
38951 NNNNNNNNNN NNNNNNNNNN NNNNNNNNNN NNNNNNNNNN NNNNNNNNNN
39001 NNNNNNNNNN NNNNNNNNNN NNNNNNNNNN NNNNNNNNNN NNNNNNNNNN
39051 NNNNNNNNNN NNNNNNNNNN NNNNNNNNNN NNNNNNNNNN NNNNNNNNNN
39101 NNNNNNNNNN NNNNNNNNNN NNNNNNNNNN NNNNNNNNNN NNNNNNNNNN
39151 NNNNNNNNNN NNNNNNNNNN NNNNNNNNNN NNNNNNNNNN NNNNNNNNNN
39201 NNNNNNNNNN NNNNNNNNNN NNNNNNNNNN NNNNNNNNNN NNNNNNNNNN
39251 NNNNNNNNNN NNNNNNNNNN NNNNNNNNNN NNNNNNNNNN NNNNNNNNNN
39301 NNNNNNNNNN NNNNNNNNNN NNNNNNNNNN NNNNNNNNNN NNNNNNNNNN
39351 NNNNNNNNNN NNNNNNNNNN NNNNNNNNNN NNNNNNNNNN NNNNNNNNNN
39401 NNNNNNNNNN NNNNNNNNNN NNNNNNNNNN NNNNNNNNNN NNNNNNNNNN
39451 NNNNNNNNNN NNNNNNNNNN NNNNNNNNNN NNNNNNNNNN NNNNNNNNNN
39501 NNNNNNNNNN NNNNNNNNNN NNNNNNNNNN NNNNNNNNNN NNNNNNNNNN
39551 NNNNNNNNNN NNNNNNNNNN NNNNNNNNNN NNNNNNNNNN NNNNNNNNNN
39601 NNNNNNNNNN NNNNNNNNNN NNNNNNNNNN NNNNNNNNNN NNNNNNNNNN
39651 NNNNNNNNNN NNNNNNNNNN NNNNNNNNNN NNNNNNNNNN NNNNNNNNNN
39701 NNNNNNNNNN NNNNNNNNNN NNNNNNNNNN NNNNNNNNNN NNNNNNNNNN
39751 NNNNNNNNNN NNNNNNNNNN NNNNNNNNNN NNNNNNNNNN NNNNNNNNNN
39801 NNNNNNNNNN NNNNNNNNNN NNNNNNNNNN NNNNNNNNNN NNNNNNNNNN
39851 NNNNNNNNNN NNNNNNNNNN NNNNNNNNNN NNNNNNNNNN NNNNNNNNNN
39901 NNNNNNNNNN NNNNNNNNNN NNNNNNNNNN NNNNNNNNNN NNNNNNNNNN
39951 NNNNNNNNNN NNNNNNNNNN NNNNNNNNNN NNNNNNNNNN NNNNNNNNNN
40001 NNNNNNNNNN NNNNNNNNNN NNNNNNNNNN NNNNNNNNNN NNNNNNNNNN
40051 NNNNNNNNNN NNNNNNNNNN NNNNNNNNNN NNNNNNNNNN    (SEQ ID NO:3)
```

FEATURES:
Start:    2058
Exon:     2058-2156
Intron:   2157-7996
Exon:     7997-8094
Intron:   8095-8869
Exon:     8870-9053
Intron:   9054-25147
Exon:     25148-25339
Intron:   25340-29365
Exon:     29366-29542
Intron:   29543-30639
Exon:     30640-30792
Intron:   30793-37517
Exon:     37518-37736

FIGURE 3, page 13 of 25

Stop: 37737

CHROMOSOME MAP POSITION:
Chromosome # 8

ALLELIC VARIANTS (SNPs):

| DNA Position | Major | Minor | Domain | Protein Position | Major | Minor |
|---|---|---|---|---|---|---|
| 825 | G | A | Beyond ORF(5') | | | |
| 2632 | C | T | Intron | | | |
| 4430 | C | T | Intron | | | |
| 4791 | C | T | Intron | | | |
| 4886 | G | C | Intron | | | |
| 4887 | A | T | Intron | | | |
| 4889 | T | A | Intron | | | |
| 5110 | G | T | Intron | | | |
| 6911 | G | A | Intron | | | |
| 7212 | A | G | Intron | | | |
| 7355 | C | T | Intron | | | |
| 7398 | T | C | Intron | | | |
| 7653 | T | C | Intron | | | |
| 8310 | A | G | Intron | | | |
| 8145 | C | T | Intron | | | |
| 8031 | G | A | Exon | 45 | R | K |
| 8462 | G | C | Intron | | | |
| 8873 | C | T | Exon | 67 | N | N |
| 9190 | C | T | Intron | | | |
| 9311 | T | - | Intron | | | |
| 9847 | T | C | Intron | | | |
| 10460 | C | T | Intron | | | |
| 20204 | G | A | Intron | | | |
| 20362 | C | A | Intron | | | |
| 21166 | G | A | Intron | | | |
| 21477 | G | A | Intron | | | |
| 22230 | C | T | Intron | | | |
| 22941 | A | G | Intron | | | |
| 23963 | C | T | Intron | | | |
| 25686 | A | C | Intron | | | |
| 26018 | A | G | Intron | | | |
| 26078 | G | A | Intron | | | |
| 26625 | C | G | Intron | | | |
| 27151 | C | T | Intron | | | |
| 28032 | G | A | Intron | | | |
| 28772 | G | A | Intron | | | |
| 29572 | C | T | Intron | | | |
| 29761 | C | T | Intron | | | |
| 30732 | G | C | Exon | 281 | L | L |
| 30841 | G | T | Intron | | | |
| 31376 | G | A | Intron | | | |
| 32032 | A | G | Intron | | | |
| 32525 | A | G | Intron | | | |
| 34179 | G | T | Intron | | | |
| 34249 | T | C | Intron | | | |
| 34451 | T | C | Intron | | | |
| 34532 | T | C | Intron | | | |
| 36541 | T | C | Intron | | | |
| 36607 | A | G | Intron | | | |
| 36681 | A | G | Intron | | | |
| 37493 | C | T | Intron | | | |
| 37966 | C | A | Beyond ORF(3') | | | |
| 37973 | T | C | Beyond ORF(3') | | | |

FIGURE 3, page 14 of 25

| | | | |
|---|---|---|---|
| 38113 | C | A | Beyond ORF(3') |
| 38298 | G | C | Beyond ORF(3') |

Context:

DNA
Position
825        GCAGTGAACGTACCTGACAGGTTTCCTGTTTGTTTTTGAGATGAAGTCTCGCTCTTGTCC
           CCCAGGCTGGAGTGCAATAGCGCGATCTCAGCTCACTGCAACCTCTGCCTCCTGTGTTCA
           AGCGATTCTCCTGCCTCAGCCTCCCAGGTAGCTGGGATTATAGGCGCCTGCCACCATGCC
           TGGCTAATTTTTGTATTTTTAGTAGAGACGCAGTTTCAGCATGTTGGCCAGGCTGGTCTT
           GAACTCCAGACCTCAGGTGATCCGCCCGCCTTGGCCTCCCAAAGTGCTGGGATTACAGGC
           [G,A]
           TGAGCCACCGCGCTCGGCTAGACCTGACAGGTTTTAAAAGGATTACTGGTTGCTGTGTTA
           AAACAGACTGCAGGATGGCTTAGGTAGCCAGTAGGTTTTTTTTTTTTGGAGACGTAGT
           CTTGCTCTGTTGGCCTGGCTGGAGTGCAGCGGTGTCATCTTGGCTCACTGCAAACTCCGC
           TTCCCGGGTTCAAGTGATTCTCCTGCCTCAGCCTCCGGAGTAGTTGGGACTACAGGCGCC
           CACCACCACACTCGGCTTTTTGTATTTTTAGTAGAGACGGGTTTCACCATGTTGGCCAG 2632       GCCGTCCTGGCTGACCTGTCCCTGCCCCCGCAAGCCGCCCTGGGCATGAGCGACTTTTGC
           GTGGTTCCCGGTGGTTGCGCTCCCCGTTTCGTCCCCTCCGTGAGCATCGGCGCTTACCGG
           TATTTTAACCCGAGGGTTACACATCTGAGGCAATGTGGGTGGGTTACGCGGGAGAGGACG
           AGTGAGTTTTTTGGTAAGCGGAATGAACTATGCAGATAACATCACATGAAGGCCGTTTCT
           GGAATGAAGTCTGACTCCTCCAGTTTCACCACCTCTTCCGGAGCTCTCCCCGCCTTGCTG
           [C,T]
           CTTCCATCGCTTCATCCTCGGTGCTTCCTGAGTTTTAAAATCGCCTATCTACGCTTCCAA
           GTTCCAATGAGTTATCTAACGTCTATGGATTAGCTAGGTGGTTGGTGGAAGGTCAGAACT
           TGGTTTTACTTAGATTTTTATCTGCCTCATGCCTGTACTATTTGTTTAATGAATGCATAG
           GAGGTGTTTTTATTCCAACAAGAAAATTATTCGTACGCGATTATTGAATGAATAGACAAA
           TTCAGCCAAGTTCTTCTGGTCTGGACCAGCCTGGCTGATTTCTGTAACTTTTTTGGGCCA 4430       GGCCTTTTTTTTTTTTTTTGAGGGGGGGGTCTCACTCCATCGTCCAGGCTAGAATGCT
           GTGGCCTGAACATGACTCACTCCAGTTTTGACTTCCTTGGCTGAAGCCATCCTCCCACCT
           CGGCTTCCTGATCCCGAGTAGCTGGGACTCCAGGCACGTGTCACCAATGCATGGCTAATT
           TTTAAATTTTTTTGTAGACACAATGTCTCGCTGCATTGCCCAGGCTGGTCTTGAACTCCT
           GAGCTCAAGCGATTTTCCCACCTCAGCCTTCAAAGTGCTGGGATTACAGGTGTGAGCCAC
           [C,T]
           GCACCCAACCAGTTTCTCTCTGCAAACTAGGGAAAAAATTTACGCTTAGCAGATATTGAG
           GGCTGATTATTTCTATCACAGAAGCATTTGGCTATAGAATTTCAGGGTTTAGTAAACTTG
           ATTTACACTGAATTTTTAGGTGCATATCAGTAAATCTACGGGCATATGCCGCCTGCAAGT
           TGTGTGGCATCACCCAAAAGCCGAGAGTAATGGAAAGAGCAGGCTGTTAGTAATCAGGCA
           GATCTGGCTCCTGTCCAATCTAAATCCTGTTATTTAGACTAATATCTTAAGTCTGTTATT 4791       GGCTGATTATTTCTATCACAGAAGCATTTGGCTATAGAATTTCAGGGTTTAGTAAACTTG
           ATTTACACTGAATTTTTAGGTGCATATCAGTAAATCTACGGGCATATGCCGCCTGCAAGT
           TGTGTGGCATCACCCAAAAGCCGAGAGTAATGGAAAGAGCAGGCTGTTAGTAATCAGGCA
           GATCTGGCTCCTGTCCAATCTAAATCCTGTTATTTAGACTAATATCTTAAGTCTGTTATT
           AAGTCCGATTTCTGACGCTATTAAGTTAGGTGAACAACCTTGGTAACTTAACCTCTGAAC
           [C,T]
           ACAGTTACTTCATCTGTAAAATAGGGATGTATGTATGGTAACGATTTTTTAACCACAACT
           TCCCAACTCTAAGATGGTCTGAAAAGAATTTTTTGAGTGTTTGGCTCAGAATCACTTGGC
           AGCAAAACCTGACTTGAAGTTGAGGCTTCATTCATCCCACTTAGTATATTCAAATGTTTT
           GCTAAAGAAATAATTATGAGGTGCTACTTCACACTGACTAGGGTTGTATATGCATTTTAT
           TGCCTATTTTCTAAAACACTAAAAATGCTAAATTCTGCCCCAGGTCTTGCCACAGATGTT 4886       CTACGGGCATATGCCGCCTGCAAGTTGTGTGGCATCACCCAAAAGCCGAGAGTAATGGAA
           AGAGCAGGCTGTTAGTAATCAGGCAGATCTGGCTCCTGTCCAATCTAAATCCTGTTATTT
           AGACTAATATCTTAAGTCTGTTATTAAGTCCGATTTCTGACGCTATTAAGTTAGGTGAAC
           AACCTTGGTAACTTAACCTCTGAACCACAGTTACTTCATCTGTAAAATAGGGATGTATGT
           ATGGTAACGATTTTTTAACCACAACTTCCCAACTCTAAGATGGTCTGAAAAGAATTTTTT
           [G,C]
           AGTGTTTGGCTCAGAATCACTTGGCAGCAAAACCTGACTTGAAGTTGAGGCTTCATTCAT
           CCCACTTAGTATATTCAAATGTTTTGCTAAAGAAATAATTATGAGGTGCTACTTCACACT FIGURE 3, page 15 of 25

```
          GACTAGGGTTGTATATGCATTTTATTGCCTATTTTCTAAAACACTAAAAATGCTAAATTC
          TGCCCCAGGTCTTGCCACAGATGTTTCAGTGGACTATGGGCCTGTGAGACCTTAAAGGGT
          TGATTGAGTAAGGATCACAGGTGATGTCCGCATTGTGCTTGGCATGGAGTTAAGTGCTTG

4887      TACGGGCATATGCCGCCTGCAAGTTGTGTGGCATCACCCAAAAGCCGAGAGTAATGGAAA
          GAGCAGGCTGTTAGTAATCAGGCAGATCTGGCTCCTGTCCAATCTAAATCCTGTTATTTA
          GACTAATATCTTAAGTCTGTTATTAAGTCCGATTTCTGACGCTATTAAGTTAGGTGAACA
          ACCTTGGTAACTTAACCTCTGAACCACAGTTACTTCATCTGTAAAATAGGGATGTATGTA
          TGGTAACGATTTTTTAACCACAACTTCCCAACTCTAAGATGGTCTGAAAAGAATTTTTTG
          [A,T]
          GTGTTTGGCTCAGAATCACTTGGCAGCAAAACCTGACTTGAAGTTGAGGCTTCATTCATC
          CCACTTAGTATATTCAAATGTTTTGCTAAAGAAATAATTATGAGGTGCTACTTCACACTG
          ACTAGGGTTGTATATGCATTTTATTGCCTATTTTCTAAAACACTAAAAATGCTAAATTCT
          GCCCCAGGTCTTGCCACAGATGTTTCAGTGGACTATGGGCCTGTGAGACCTTAAAGGGTT
          GATTGAGTAAGGATCACAGGTGATGTCCGCATTGTGCTTGGCATGGAGTTAAGTGCTTGA

4889      CGGGCATATGCCGCCTGCAAGTTGTGTGGCATCACCCAAAAGCCGAGAGTAATGGAAAGA
          GCAGGCTGTTAGTAATCAGGCAGATCTGGCTCCTGTCCAATCTAAATCCTGTTATTTAGA
          CTAATATCTTAAGTCTGTTATTAAGTCCGATTTCTGACGCTATTAAGTTAGGTGAACAAC
          CTTGGTAACTTAACCTCTGAACCACAGTTACTTCATCTGTAAAATAGGGATGTATGTATG
          GTAACGATTTTTTAACCACAACTTCCCAACTCTAAGATGGTCTGAAAAGAATTTTTTGAG
          [T,A]
          GTTTGGCTCAGAATCACTTGGCAGCAAAACCTGACTTGAAGTTGAGGCTTCATTCATCCC
          ACTTAGTATATTCAAATGTTTTGCTAAAGAAATAATTATGAGGTGCTACTTCACACTGAC
          TAGGGTTGTATATGCATTTTATTGCCTATTTTCTAAAACACTAAAAATGCTAAATTCTGC
          CCCAGGTCTTGCCACAGATGTTTCAGTGGACTATGGGCCTGTGAGACCTTAAAGGGTTGA
          TTGAGTAAGGATCACAGGTGATGTCCGCATTGTGCTTGGCATGGAGTTAAGTGCTTGATA

5110      AAATAGGGATGTATGTATGGTAACGATTTTTTAACCACAACTTCCCAACTCTAAGATGGT
          CTGAAAAGAATTTTTTGAGTGTTTGGCTCAGAATCACTTGGCAGCAAAACCTGACTTGAA
          GTTGAGGCTTCATTCATCCCACTTAGTATATTCAAATGTTTTGCTAAAGAAATAATTATG
          AGGTGCTACTTCACACTGACTAGGGTTGTATATGCATTTTATTGCCTATTTTCTAAAACA
          CTAAAAATGCTAAATTCTGCCCCAGGTCTTGCCACAGATGTTTCAGTGGACTATGGGCCT
          [G,T]
          TGAGACCTTAAAGGGTTGATTGAGTAAGGATCACAGGTGATGTCCGCATTGTGCTTGGCA
          TGGAGTTAAGTGCTTGATAAATGGTGGTTATCAATCTGATTATGTAAATTTATGTAAATT
          CAGTTCTCAAGTTTGTGGTTTTTTCCCCTCCTGGAGAAATCTATTCTATTTTAAAGTGA
          GGAAGGCTCCGTGGAGGGCTGGTAGCTGGTAGCTGTTCACTTGTGGAACTTTCAGCCTGA
          GGCTGGAGCCCCTTCCTGGGAGTCTGGTCTTGTCGTCTTCCTGACCACCCCCACACCCTT

6911      CCACCTTGGCCTTCCGAAGTGCAGGGATTATAGGCGTGCGCCACTGCACCCGGCCCTGTT
          GGATAAATGATTCCAGTCTCTCCCAAAAAGAACTGTTGTAAGACTGTGGGGTGAGGGGAG
          GGAAGGGACAAATAGGAACCCGCCGTATTTTCCACTCCCTGTGGGCCTAAAACTGCTCTA
          AAAAATAGTCCATGAAAAATACATAGTACAAACAGCAACTCTTTCTGATATGCTTGCAT
          TTAAAATCAGGCTTTTTCTCCCTTTTGGAAAAACACAGTCCTTGTTTGCTTTAGGGAAGA
          [G,A]
          TAAAGGTCAGTGCGCTGCATTGCATTAATTTCGAAGGGAAAGATGAGAAGACATCTTGAA
          AGGAATGGCTGGCTTTCTAGAGAATAGTAGAGGCTTAATAGGTGTCATAGAAAAACCAGG
          GTTGGACAGTGGTAGTAAAACGGCAAAACAGATTTTATTCAGAAAACTACTGCAGTAAG
          AGGAGAGAGACCTCGGTACAGAACTGCTCCACTGCGAATACAAAGAAAAGTAGGAATTGA
          TGGCGGGGGAGCCGGATGTCAGTGGATGGAAAATTATTACGAGGAAACACAGGGGTGTGC

7212      TAAAGGTCAGTGCGCTGCATTGCATTAATTTCGAAGGGAAAGATGAGAAGACATCTTGAA
          AGGAATGGCTGGCTTTCTAGAGAATAGTAGAGGCTTAATAGGTGTCATAGAAAAACCAGG
          GTTGGACAGTGGTAGTAAAACGGCAAAACAGATTTTATTCAGAAAACTACTGCAGTAAG
          AGGAGAGAGACCTCGGTACAGAACTGCTCCACTGCGAATACAAAGAAAAGTAGGAATTGA
          TGGCGGGGGAGCCGGATGTCAGTGGATGGAAAATTATTACGAGGAAACACAGGGGTGTGC
          [A,G]
          TTCTTGCTGAAGGCAGGCCAGAGTTATCAGACATCACCTGAGGGATGGAGGGGGATGTGG
          AACCTAATCGGCTGTCTAGGGTGATCAGATACTGAAGTTGGGGATTCTGGTCAAATCAA
          TTTAGCAGGATTCTTGGTAAAACTGGGCGATGCAAAGACAGATGCGTTGAGTACAAAGTC
          CAGGCTTTATTGGGAAGAGGATTTCAGCGGAGCCCGAGTAGAGTTTGGTCTAGGGAGACT
          CTGTCACTGGGAGGACGAGCGAGCCGCTCGGAAGTGCGCTGGGTTCTCTTAGCGGCCAGT
```

FIGURE 3, page 16 of 25

7355    CAAAACAGATTTTATTCAGAAAAACTACTGCAGTAAGAGGAGAGAGACCTCGGTACAGAA
        CTGCTCCACTGCGAATACAAAGAAAAGTAGGAATTGATGGCGGGGGAGCCGGATGTCAGT
        GGATGGAAAATTATTACGAGGAAACACAGGGGTGTGCATTCTTGCTGAAGGCAGGCCAGA
        GTTATCAGACATCACCTGAGGGATGGAGGGGGATGTGGAACCTAATCGGCTGTCTAGGGT
        GATCAGATACTGAAGTTGGGGGATTCTGGTCAAATCAATTTAGCAGGATTCTTGGTAAAA
        [C,T]
        TGGGCGATGCAAAGACAGATGCGTTGAGTACAAAGTCCAGGCTTTATTGGGAAGAGGATT
        TCAGCGGAGCCCGAGTAGAGTTTGGTCTAGGGAGACTCTGTCACTGGGAGGACGAGCGAG
        CCGCTCGGAAGTGCGCTGGGTTCTCTTAGCGGCCAGTGGGTTCTGGTGAGAAGGGCAACA
        GCGGGAGGAGGCGCCGGTGCGGAGCGGGAGGCCGGGGGCGGGGCTGCGGGGCTGCGGGGC
        GGGCCCGTTGTGGGTCGGCCCAGCGCGTATTCGAGTAGAGGGCGAGCCCGTCCCGCCTCT

7398    GAGACCTCGGTACAGAACTGCTCCACTGCGAATACAAAGAAAAGTAGGAATTGATGGCGG
        GGGAGCCGGATGTCAGTGGATGGAAAATTATTACGAGGAAACACAGGGGTGTGCATTCTT
        GCTGAAGGCAGGCCAGAGTTATCAGACATCACCTGAGGGATGGAGGGGGATGTGGAACCT
        AATCGGCTGTCTAGGGTGATCAGATACTGAAGTTGGGGGATTCTGGTCAAATCAATTTAG
        CAGGATTCTTGGTAAAACTGGGCGATGCAAAGACAGATGCGTTGAGTACAAAGTCCAGGC
        [T,C]
        TTATTGGGAAGAGGATTTCAGCGGAGCCCGAGTAGAGTTTGGTCTAGGGAGACTCTGTCA
        CTGGGAGGACGAGCGAGCCGCTCGGAAGTGCGCTGGGTTCTCTTAGCGGCCAGTGGGTTC
        TGGTGAGAAGGGCAACAGCGGGAGGAGGCGCCGGTGCGGAGCGGGAGGCCGGGGCGGGG
        CTGCGGGGCTGCGGGGCGGGCCCGTTGTGGGTCGGCCCAGCGCGTATTCGAGTAGAGGGC
        GAGCCCGTCCCGCCTCTCGTCGGGCGCTTCCCAGATCTGCTTGAGTCTATGGAGGAAAAA

7653    AACTGGGCGATGCAAAGACAGATGCGTTGAGTACAAAGTCCAGGCTTTATTGGGAAGAGG
        ATTTCAGCGGAGCCCGAGTAGAGTTTGGTCTAGGGAGACTCTGTCACTGGGAGGACGAGC
        GAGCCGCTCGGAAGTGCGCTGGGTTCTCTTAGCGGCCAGTGGGTTCTGGTGAGAAGGGCA
        ACAGCGGGAGGAGGCGCCGGTGCGGAGCGGGAGGCCGGGGCGGGGCTGCGGGGCTGCGG
        GGCGGGCCCGTTGTGGGTCGGCCCAGCGCGTATTCGAGTAGAGGGCGAGCCCGTCCCGCC
        [T,C]
        CTCGTCGGGCGCTTCCCAGATCTGCTTGAGTCTATGGAGGAAAAACTCCGCGGGGTCCGC
        GATTCCCATGGCCGCAGCCGCCTGCGGCACCAAGGCCATGGCCCTCTTCAAGCGCACCTT
        GGTGCTGAGTCCCGCCGCGGCGCCCAGGGGCCCGGGCGCAGGCACCGCCCCGCGGGGCTG
        CTGCTTGCCTCCTGCCGCCTGGCCCTGCAAGGACTGGCCTCGGGGAGAGGGCGGCAGGCT
        GTGGAGCCGCCTGCCCCAGTCCCAGTCCCACTCCCACTCCCACTCCCACTCCCACTCCTG

8310    CAGCCTGAAAACTTGCTACAAGTATCTCAATCAGACCAGTCGCAGTTTCGCAGCTGTTAT
        CCAGGCGCTGGATGGGAAATGCGGTGAGTGATGGAGGCAGCGCCTCTGGCTTGGAGGAA
        AGCTTGTCCGGGACTTTTGAGTGTGTTGGAAGCTACCTTTTGATATAGCGCTCAGCGTTG
        CAGCCTCGTTGCTGTGGCTTATCCAGAACATAGCCCGGCCCTACGTGTTTACTTTAGAAA
        GCCCTTCCAGGCTCTTTGCCATCTAGTAGAGTCCCTGCGGGCCCAGCCTTTCAGAGAAG
        [A,G]
        GGGGGAGGGGGTGATGTTTATTAACTTTTTTTAGTCTTGGCAGCTGAACCTGCCTGTGA
        GCAGGTCGTGTATTTCTCGGCTTCCCTTATCCAACTTTGCATTTCTATTTCTAGCATATT
        GGGTTGATTCTTTTGAAGCTGCCTCTGTGCACATTACACCCATGAACTTAGACCAGTTGC
        CTTTATGTATGATCGTATTTATACTGAGAAGTTACTGTGTTTTTTGACTTTCTTTTCTAT
        TTGCTACATATTAGTTCGGTCTAAACGTTTGGTCTTCTGGTCTCCATAGTTCTACATTG

8145    CAGCCTGAAAACTTGCTACAAGTATCTCAATCAGACCAGTCGCAGTTTCGCAGCTGTTAT
        CCAGGCGCTGGATGGGAAATGCGGTGAGTGATGGAGGCAGCGCCTCTGGCTTGGAGGAA
        AGCTTGTCCGGGAC
        [C,T]
        TTTGAGTGTGTTGGAAGCTACCTTTTGATATAGCGCTCAGCGTTGCAGCCTCGTTGCTGT
        GGCTTATCCAGAACATAGCCCGGCCCTACGTGTTTACTTTAGAAAGCCCTTCCAGGCTCT
        TTGCCATCTAGTAG

8031    CAGCCTGAAAACTTGCTACA
        [G,A]
        GTATCTCAATCAGACCAGTC

8462    GCTACCTTTTGATATAGCGCTCAGCGTTGCAGCCTCGTTGCTGTGGCTTATCCAGAACAT
        AGCCCGGCCCTACGTGTTTACTTTAGAAAGCCCTTCCAGGCTCTTTGCCATCTAGTAGAG

FIGURE 3, page 17 of 25

```
       TCCCTGCGGGCCCAGCCTTTCAGAGAAGGGGGGGAGGGGGTGATGTTTATTAACTTTTT
       TTAGTCTTGGCAGCTGAACCTGCCTGTGAGCAGGTCGTGTATTTCTCGGCTTCCCTTATC
       CAACTTTGCATTTCTATTTCTAGCATATTGGGTTGATTCTTTTGAAGCTGCCTCTGTGCA
       [G,C]
       ATTACACCCATGAACTTAGACCAGTTGCCTTTATGTATGATCGTATTTATACTGAGAAGT
       TACTGTGTTTTTTGACTTTCTTTTCTATTTGCTACATATTAGTTCGGTCTAAACGTTTGG
       TCTTCTGGTCTCCATAGTTCTACATTGGTTAAATGCAACTCACTTCTGGGAGTAGTGGTG
       ACATTCAACTAGTAGGCTTTTTAATAAACTACAGAAGTTCATTACTCTCATGTAAGGAAG
       GAAAACTAATGTAACTTTCGTTAAGTATGAAAAGCGTTGGATATCCTTATAGTTCTTTAG

8873   AAACGTTTGGTCTTCTGGTCTCCATAGTTCTACATTGGTTAAATGCAACTCACTTCTGGG
       AGTAGTGGTGACATTCAACTAGTAGGCTTTTTAATAAACTACAGAAGTTCATTACTCTCA
       TGTAAGGAAGGAAAACTAATGTAACTTTCGTTAAGTATGAAAAGCGTTGGATATCCTTAT
       AGTTCTTTAGAGTTAAGGGTGAGATGGGTTTAGAAAGTGGCCAGGCACAAGTTATTTTAA
       AATAAAAAATCTTTGGCTGTTTGTTCCAATATATTAATAGTTTTCCCTTTTTTACAGCAA
       [C,T]
       GCAGTGTGCATATTTTATCTGGTTCTCCGAGCTCTGGACACACTGGAAGATGACATGACC
       ATCAGTGTGGAAAAGAAGGTCCCGCTGTTACACAACTTTCACTCTTTCCTTTACCAACCA
       GACTGGCGGTTCATGGAGAGCAAGGAGAAGGATCGCCAGGTGCTGGAGGACTTCCCAACG
       GTGAGTGGGGTTACGCATCTTGTCTACGGACTGTTGTGTTCATAATTGCTAACGTGGTTG
       TCCGGTAGCCTCCATACATGTGGAGAAAGGTTAAATAAGCATTCTGAGGGCAGCATAATG

9190   ATCTGGTTCTCCGAGCTCTGGACACACTGGAAGATGACATGACCATCAGTGTGGAAAAGA
       AGGTCCCGCTGTTACACAACTTTCACTCTTTCCTTTACCAACCAGACTGGCGGTTCATGG
       AGAGCAAGGAGAAGGATCGCCAGGTGCTGGAGGACTTCCCAACGGTGAGTGGGGTTACGC
       ATCTTGTCTACGGACTGTTGTGTTCATAATTGCTAACGTGGTTGTCCGGTAGCCTCCATA
       CATGTGGAGAAAGGTTAAATAAGCATTCTGAGGGCAGCATAATGTGAGGGTTAAAAACTC
       [C,T]
       GGTAGCCAAGACTCTGAAGCCAGGCTGCCTGGGTTGGAATCTCAAATCTCCCACTTACTA
       AACTGTTGGTTACTTACAAAGACTCTCTGTGCCTCAGTTTCTTCATCTGTAAAATAGGGG
       TAATAATAACACCTACCTCATGGTATTCTGAGGATTCAAAGAATTAACGTAGGTAATGCT
       CTTAGAATGTTAGCTACTGCTGTTATTATCAGTATTGGAAGTCCAGTGTTTCTTCCTGTG
       GGAAGACGCAGTCAAATTTTAGTGTTGTGAAAGATTCTCAGGCTAGCTCACAAAAGCCTG

9311   GAGCAAGGAGAAGGATCGCCAGGTGCTGGAGGACTTCCCAACGGTGAGTGGGGTTACGCA
       TCTTGTCTACGGACTGTTGTGTTCATAATTGCTAACGTGGTTGTCCGGTAGCCTCCATAC
       ATGTGGAGAAAGGTTAAATAAGCATTCTGAGGGCAGCATAATGTGAGGGTTAAAAACTCC
       GGTAGCCAAGACTCTGAAGCCAGGCTGCCTGGGTTGGAATCTCAAATCTCCCACTTACTA
       AACTGTTGGTTACTTACAAAGACTCTCTGTGCCTCAGTTTCTTCATCTGTAAAATAGGGG
       [T,-]
       AATAATAACACCTACCTCATGGTATTCTGAGGATTCAAAGAATTAACGTAGGTAATGCTC
       TTAGAATGTTAGCTACTGCTGTTATTATCAGTATTGGAAGTCCAGTGTTTCTTCCTGTGG
       GAAGACGCAGTCAAATTTTAGTGTTGTGAAAGATTCTCAGGCTAGCTCACAAAAGCCTGC
       CGACTGTATGATGCAGCCTACCTGTAACACTGCTGGCCTCTTGACTACCCGGAGCCTGGT
       AGCATGGGACTGCTGCTCACGATGGGCAGCAGCCTGGCATGGGGCGGTGTCTGTTGGCA

9847   CTGGTAGCATGGGACTGCTGCTCACGATGGGCAGCAGCCTGGCATGGGGCGGTGTCTGT
       TGGCAGCTAGGGCGAGCCTCTGCCACTTCACCTGTGATCCTGGGCAAGTTCCTTATCTGC
       TTTGTGTCTCCCGTCTCCTCGTTTGTAAAGTTAGAGCTGAGAGGATTAATTTCGCACATAT
       AAAGTACTTAGTGCCTGGTACAGGGTAAGTATTCTGTAAGTATTAGCTATTTGGTCTATT
       TTGTTGGAGTAAAGTGGGTTATAGTTAAAATCCTAAGATTTTTAAAGTCCCTCAAGTTCA
       [T,C]
       GTGGACATCTGCCTAGGTCCTACTATCCTAGAATTCGCATGTCTTATCACACAAATAACT
       GATTCTTCCATATCTTATAAATAAAGGTTTGATTTAGCAAAGTCACATGTTGTGTAATAG
       CTCGAAGAAGCCCTTTTTGTCCACAGTTGCCAGAGCTTTTGGAGAACAGTCCTTATGTTA
       TTGAAACAAACCTAATCTGTAGCTGAGTTGGGAGGGAGCTAAGTGGACAGAGAGTCCTCC
       ACCCAAACAAAAGAATCTTTGATTCTTGGGCATAATGGGAGCAATATTTAAAAAAAAAAA

10460  AGGAATGTTTGGGGAAGACTCTTGCGGTGCAAAGGCTGTTTCAGATTGCTGAGATCAGAC
       CTTAAGTACCAAAGCCCAAATATAGTACAACATAATACAAATGAGAAGAAAATAGCTGAA
       GAATAATTCGAGTTTATACAGTACAATTCAAGAGAAGAAAGAAATTTATGACGACTAGC
       TGGGTGAGAATTAGAACTGTAACCCTGGGAAGGTCCTGGTGATTTGACTCTCACAGGACA
       CCTGATGACCAGAGGATGGGTTTCCTTTGATGGGAAATCTGTGGCGATTCATTGATGGGC
```

FIGURE 3, page 18 of 25

```
       [C,T]
       TCTGAATTCTGCTGAAGCAGAGGAAGTAGTAATACCCCATTTATAATGGAAGTGCATTCT
       CACTTAAAAACAACTAATATTATTCTAGCTGGACCTAGCCTCTAGAAACAGCCAAATTAC
       ATTTGACTTGAGTGGATTCATAATAATTAAAAAATTTCTGGGGCATGGGATAAATGTGTT
       AGGTATTGCTAAGTCAAGGCAGCCCTATCCCCTCAGCAGAAGTGAGGGAATATGAAAGTG
       TGTGAATGCTAACATAATTTTGGGGAATATCGCCGTCAGATTTCCAGATGATATTCCAAC

20204  TCTGCCAGTTGCGAAGACTGGGAAAAGCACAGTATTTGGGCAGAGTATACTGTTCCTCCA
       GGTACAGTCACTCACGCCTTTCCTTGGCTAGGAAAGGGAAATCCCCTGACCCCTTGCACT
       TCCTGGATGAGGTGACGTCCTGCCCTGCTTTGGCTCACCCTCCATGGGCTGCACCCACTG
       TCCAACCAGTGCCAATGAGATGAACCAGGTACCTCAGTTGGAAATGCAGAAATCACCCAT
       CTTCTGCATCGATCTTGCTGGGAGCTGTAGACCAGAGCTGTTCCTACTGGGGCATCTTGG
       [G,A]
       AGCAACTCTGGGTCTGAGTTTCTGTTTGTTGCCCTGATGTATATCCCCAGTGCCTAGAAT
       GATACTTGTTACATAGGAAGTGCTTGATCCATGTTTGCACAAATGAATCTTTCTCATAAT
       GAGGTTTCTCTAAACAAGCTGTTCTCCCAAAAACTTACACCCAGCTTTATGTTGAAGCAT
       CTCATTATACATTGGAAAGATGAAATGTGTAGTGAGACTTTGAATCTTCTTTTGAATCTA
       GAAACATTAGCATTTTTAGACCATTCTATTTTAATATTTATGAAATTTATGAAATAATAA

20362  CCTCCATGGGCTGCACCCACTGTCCAACCAGTGCCAATGAGATGAACCAGGTACCTCAGT
       TGGAAATGCAGAAATCACCCATCTTCTGCATCGATCTTGCTGGGAGCTGTAGACCAGAGC
       TGTTCCTACTGGGGCATCTTGGAAGCAACTCTGGGTCTGAGTTTCTGTTTGTTGCCCTGA
       TGTATATCCCCAGTGCCTAGAATGATACTTGTTACATAGGAAGTGCTTGATCCATGTTTG
       CACAAATGAATCTTTCTCATAATGAGGTTTCTCTAAACAAGCTGTTCTCCCAAAAACTTA
       [C,A]
       ACCCAGCTTTATGTTGAAGCATCTCATTATACATTGGAAAGATGAAATGTGTAGTGAGAC
       TTTGAATCTTCTTTTGAATCTAGAAACATTAGCATTTTTAGACCATTCTATTTTAATATT
       TATGAAATTTATGAAATAATAAGAAACATGAGGCCGGGCTCAGTGGCTTATGCCTGTAAT
       CCCAGCAGTTTGGGAGGCCAGGGCTAGTGGATCATGAGGTCAGGAATTTGAGACCAGCTT
       GGCCAACATGGTGAAACCCCACTTCTACTAAAAATATAAAAATTAGCTGGGCGTGGTGGT

21166  TAATTCCGCCATTGTTTGCCTTGTGATCTTTGGTGCCATGTCTGTACATATTTCATGATT
       TCTGTGTTTTTACGGTTTCCATTTCAGATCTCCCTTGAGTTTAGAAATCTGGCTGAGAAA
       TACCAAACAGTGATTGCCGACATTTGCCGGAGAATGGGCATTGGGATGGCAGAGTTTTTG
       GATAAGCATGTGACCTCTGAACAGGAGTGGGACAAGGTTAGTCTCATAAAACAGTGTCTG
       TGTGTGATGTATTAGACAGAGCTGGCAGTCCTCATAGTGAAGCTCAGAACAAGAAAAGTT
       [G,A]
       TCCAGTATTTTCAGCCCCTCTGGTTTTACAATTCATCTGTTTAGGTTGAATGTCTCATCA
       TAAACAGTTTATTCCAGAGTTAATTCCAAACCAGCAGCTATGTAGGATATCAGCCAGGCT
       AGGAGTAGGGTACTGGAGAGAAGTGCTTATCTAGACAAAGGGATGTAATTGACCATGAAG
       ATTAAAACTACACATCAAAACATAAGGTAGGGTTAGGAGTCTTGCCTATTTTTCATAGGA
       ATGGTGTTTGTGAGACTTACTCATCACTTCTGTGGAAGTAAAGACATTTTATTTATTTAT

21477  TCAGCCCCTCTGGTTTTACAATTCATCTGTTTAGGTTGAATGTCTCATCATAAACAGTTT
       ATTCCAGAGTTAATTCCAAACCAGCAGCTATGTAGGATATCAGCCAGGCTAGGAGTAGGG
       TACTGGAGAGAAGTGCTTATCTAGACAAAGGGATGTAATTGACCATGAAGATTAAAACTA
       CACATCAAAACATAAGGTAGGGTTAGGAGTCTTGCCTATTTTTCATAGGAATGGTGTTTG
       TGAGACTTACTCATCACTTCTGTGGAAGTAAAGACATTTTATTTATTTATTTTAAAGCCA
       [G,A]
       TCAGATTTAGCAGGCAGAGACATTTCAGACATCTAAAGTGTTGATGTATTTCATACCTTT
       AACTGTGCTTAAATTAGGATCTCCGAAAAGATGCTGCTACATGGTCACTACGTTAGTGTA
       GGTCCAAGGTCTTGGGCCTCTTAATTTTTCAAACCTCAAAACTTGACAGCAGTTATCTTT
       GGAACTGCTGATTTGTGCTTCCTAAGTTAACAGCATACAATGACTGCTAGAAATCAATTT
       CTGCATTTAAGGTGAAGTTAGCCGGGTACTATGGTTTACCTGTAATCTCAGCACTTTGGG

22230  GGATTGCTTGAGCCCAAGAGTTGAAGGTTGCAGTGAGCCATGATTGTGCCACTGCACTCC
       AACGTGGGTGACAGAGCAAGACACCTACTGAAAGAAAATAAAGTTGAAGTTAAAACTTCT
       GGCCAAGAACCAGCACTGGTTATGATAGTACTCATTTTCTGTTGTGCAGATTTATTCAG
       GAAACTTAATTTTAGGTTGTTGAATAGAAGTTTTGATCAGATAAAATTGAATTAAAAAAA
       ATTTTTTTTGAGACAGGGTCTTGCTGTTATCCAGGCTGGTGTGTAGTGGTGTGATCACGG
       [C,T]
       TCCCCGCAGCCTCAACCTCCTGGGCTCAGGTGATCCTCCCACCTCAGCCTACCGAGTAGC
       TGTAACTACAGTGCATGACACCATACCAGGCTCATTTTTGTACATTTTTTGTAGAGAGAG
```

```
              GGTTTTGCCATGTTGCCCAGGCTAGTCTCAAACTCCTGGCATCAAACAGTCCTCCCACTC
              TGGCCTCTCAAATGTTGGGATTACAGGCATGACCAGCCAATTATTTCAAGGAGTTATTTT
              TTTTCTTCTACTTTGGGGGAAGATGAATTATATAAGTCTCCATTTTAGGAGTATTTCTAC

22941         AATTTCTGTCTACCTAATTTCAGCAAGATTTCACTCTTTTCATGTTACTTTTGTCCCAGA
              ACAAATTTCAAGTGCTTTCTCTTCACCTGTGCATTCTTCCCCCTGATTAGTCTCTGGCTT
              TGTATTACTTTCAGTCAGAGACGACTTTTTTTTTTGAGACAGGGTCTCACTCTGTCACC
              CAGACTGGAATGCAGTGGCACAGACAAGGCAGCCTTGACCTTCTGGGCTCAAGCAATCTT
              CCTTGCCCTCAGCCTCCTGAGTAACTGGGACCACAGGCACGTTGCCACCATGCCTGGCTA
              [A,G]
              TTTATTTTAATTTTTATTATTTTTGAGACAGGGTATTGCTCTGTCACCCAGGCTGGAGTG
              TAGTGGCATGATCAAGGCTCACTGCAGCCTTCACCTCCTGTGCTCAAGCAGTCCTCTCAC
              CTCAGCCTCCCCATTAGCTGGGACTATAGGTCCACACCACTACACCAGGCTAATTTTTGT
              AATTTTTTGGTAGAGACAGGGTTTCATCGTGTTGCCTAGGCTGGTCTTGAGCTCCTGGGC
              TCAAGCGATTCACCTGCCTTAGCCTCCCAGGTGTGAGCCACTACACTCAGCCTTTTAAAA

23963         ATACTACCTAGTTTTGAACTCTTAGCCCCTGCCACAGACACGGCAGCCCCTTGAACCTTC
              CTGGGTTCAAGCGAGCCTCCTACTTCAGCCCCCTGAGTAACTGGGACCACTGGCCTGTGT
              CACTGTGCCTGGCTAATTTTTTTTTTTCCTCACATGGGCAATGTTGGGCAAGTTAAATC
              GACTTCTTTGTGCCTCAGTTTCCTCATCTGAAATGGAGATCATACTGCTATGTACCTGAT
              ACAATGTTTGTGAGGATTGAATGTGCAGAGTTCTTTTTTTCTGTTGTTGTTGTTTTGAGA
              [C,T]
              GGAGTCTCACTCTG

25686         CTGAAAAATCCTTTAACTCTTGTGGTTGCGGGTGACAGAAAAACAAGCCAGGCCTCCCCC
              AGGCAGCATAAGGGGATGTGGAAAATAGGATAGATTGACATGAGTTTGCTTCAGGTAGAC
              TGGCTGACTCCCAGGATTCACACCACGTAATCAGTATATTCAAGCCTTGCTGTCCTTGAT
              TTCTTTCAGACGGTCTTTCTCCAAGTGGTGGATATGGTAACAACCCACGTGCACTAGCTT
              AACAAAAAGTTCTTAGGAATGGCTTTGTTCGGCCTGGCGCAGTGGCTCATGCCTGTAATC
              [A,C]
              CAACAGTTTGAGAGGCCAAGGTGGGCGGATCACCTGAGGCCAGGAGTTCGAGACCAGCCT
              GGCCAACATAGTGAAACCCCGTGTTTACTAAAAAATACAAAAATTAGCCGGGCGTGGTGG
              CAAGGGCTTGTAATCCCAGCTACCTGGGAGGCTGAGGCAGGAGAATCGCTTGAACCCAGG
              AAGCAGAGATTGCGGTGAGCTCAGATTGTGCCACTGCACTCCAGCCTGGGCGACAGAGTG
              AGACTCCCTCTCAAAAGAAGAGGAAGGGCTTGGTTCTTCTGCTCAGCCCTGAATCAGTTA

26018         ACCTGAGGCCAGGAGTTCGAGACCAGCCTGGCCAACATAGTGAAACCCCGTGTTTACTAA
              AAAATACAAAAATTAGCCGGGCGTGGTGGCAAGGGCTTGTAATCCCAGCTACCTGGGAGG
              CTGAGGCAGGAGAATCGCTTGAACCCAGGAAGCAGAGATTGCGGTGAGCTCAGATTGTGC
              CACTGCACTCCAGCCTGGGCGACAGAGTGAGACTCCCTCTCAAAAGAAGAGGAAGGGCTT
              GGTTCTTCTGCTCAGCCCTGAATCAGTTACTGTTGCTACACAGCTGAGTTCTCTGGCCTC
              [A,G]
              CCTGGATTACGTCTACACAGTACACACAGAATGGATTTCCCCCAAAGAAAGAATTCTGCG
              GCAGGAAGGGGAAAGGGATGGCAGGTAGACAAAAACTCCAGGTGTCTGTAATAAGGGACA
              GGGTCGATCTTTAATTAAAACATGGACAGGGAACAGAAAGCTTTTGATACTGATTTTGTT
              CAGAAGGAAAGTAGAAAATTTTATGACTGTTCCCTGAATTTATTCCAGCATTTACCTTTT
              GCTTTCCATAAAAGTGTTTCCTGCAGCCAAGTACTTTAAAGTTTTAAAAAGACGGGTGAG

26078         AAAATACAAAAATTAGCCGGGCGTGGTGGCAAGGGCTTGTAATCCCAGCTACCTGGGAGG
              CTGAGGCAGGAGAATCGCTTGAACCCAGGAAGCAGAGATTGCGGTGAGCTCAGATTGTGC
              CACTGCACTCCAGCCTGGGCGACAGAGTGAGACTCCCTCTCAAAAGAAGAGGAAGGGCTT
              GGTTCTTCTGCTCAGCCCTGAATCAGTTACTGTTGCTACACAGCTGAGTTCTCTGGCCTC
              ACCTGGATTACGTCTACACAGTACACACAGAATGGATTTCCCCCAAAGAAAGAATTCTGC
              [G,A]
              GCAGGAAGGGGAAAGGGATGGCAGGTAGACAAAAACTCCAGGTGTCTGTAATAAGGGACA
              GGGTCGATCTTTAATTAAAACATGGACAGGGAACAGAAAGCTTTTGATACTGATTTTGTT
              CAGAAGGAAAGTAGAAAATTTTATGACTGTTCCCTGAATTTATTCCAGCATTTACCTTTT
              GCTTTCCATAAAAGTGTTTCCTGCAGCCAAGTACTTTAAAGTTTTAAAAAGACGGGTGAG
              GCTAAGTGTGGTGTCTCATACTTATAATCCCAGTGCTGAGGCCAGGAGTTCAAGACCAGC

26625         TGTGGTGTCTCATACTTATAATCCCAGTGCTGAGGCCAGGAGTTCAAGACCAGCCTGAGC
              AACACAGCAAGATACCATCTCTATAAAAAATTGTTAGAAAATGATTCTGCTGAAAGAGCA
              AAAATAAAAATTAAAGAAAGTAGAAAAAATAAAACTAAATTTAAAAGATTAACTGGGCAT
```

FIGURE 3, page 20 of 25

```
        GTTGGCATGCACCTGTATTCCTAGGTATTCGGGAGGCTAAGGCACAAGGATCCCTTGAGC
        GCAGGAGCTCAAGGTTGGATTGAGTTGTAATCACACCACTGCACTCCAGCCTCGGTGGCA
        [C,G]
        AATGAAACTGTCTCAAGAAAAAAAAAAGTGACAGAGGGAAACAATATTTGCAATTCATA
        GAGCAGATACAGGGTTCATATTCCTAATATTAAAAAAAACTTCTAAAAGTTAAGAAAAAG
        GCCAACTGCCCCACAGAAAAATGGGCAAGGAGATAAGAACAAGATTGTTCACAGGAAGAG
        ACACACAGATGATTATTAAAAATCTGAAAAGATGCTGAGTCTTACTCCTAAGAAAAATTC
        ACATTTAAACTACTCTGGGGGCTGGGCAAGGTGGCTCACGCCTGTAATCTCAACACTGGG

27151   TCCTAAGAAAAATTCACATTTAAACTACTCTGGGGGCTGGGCAAGGTGGCTCACGCCTGT
        AATCTCAACACTGGGAGACCAAGGCAGGAAGATCACTGAAGCCAGGGTATCGAGACCAGC
        CTGGACAACGTAGTGAGACCTTATCTCTTAAAACAAAACAAAACAAAACAAAACAAAAAA
        AACAGTAAAAATTGGCCGGGCACAGTGACTCCTGCCTATAATCCCAGCACTTTGGGAAGC
        CCAGGTGAGTGGATCACTTGAGGTCAGGTGTTTGAGAACAGCCTGGCCAACATGGCAAAA
        [C,T]
        TCCGTCTCTACTAAAATTACAAAAATTAGCCAAGTGTGGTGGCATACGCTGGTAGGGCCA
        GCTACTTGGGAGGCTGATGTGAGACTCCATTTAAAAAAAAAAATCAAAAATTAGCTGGG
        TATAGTGGCACACCCCTATAGTTCTCGCTCCTTGGGAGGTTGAGGCAGGAGGATTGCCTG
        AGCCCAGGAGTTCAAGGCTGCAGTGAACCATGATCACACCACTGCATTCTAGCAGCCTGG
        GAGACAGAGCAAAACCCTTGTCTCAAAACAAACAAACAACAACAAAAACAAAAACACTT

28032   AGGAGCAGAGCCCTGCTCTTCTCATTCACTTACTTTATCTGTAAAATAGCATCATTTCTA
        CCACACGGTGGTGGTGTGAATAAAATGAGATGAACTTCTAGCATAGAGTGCTTAGTAAAG
        GTTCTGGACATTTCGTAGTAGTTGAATCATGCCAAATGTGGTCCTAGGTGATTGGCTTCT
        TTTGCTAGCATGTTTTCAGGGCTCCTCCATGCTGGGGCATTGCATCACTGCTTTATTCCT
        TTTTATCGCCTAGTATTATTCCACTGTGTGGATAGACCACATTTATCCATTCATCAGTTG
        [G,A]
        AGGATATTTGGGTTCTTCCCATTTTTTTTGGCTATGGTGAATAGTACTGTGTACATTTGC
        ATATAAGGTTTTGTGTAGATGTGTGTTTTCCTTTTTCTTGGGTCTATGCTGAGAAGTGGA
        ATTGCTGGTTCATACAGCAGCTCGAACCTTGTGAGGAGCTGCCAGACGCTTTTCCAAGGT
        CGCTCCACCATTTTACATTCCCGTCAGCAGTGTGAGAGTCCCAGTTTCACCAGCACTTGT
        TGTTATCTCTTTTTAACTGTATGTATATATACTTAACATTTTATTTATAATAAATGTACA

28772   AAAAATCATCAAGCCGAATCCCACTGTTAGAATTAAAGGTTTTATTTCACTTTCAAGTTA
        TCAGGATCCAGGGAGGTGTAATACACTTAGAGGATAGACTCAGCTCATTTCCCAGCTATG
        CCTTTCAGCAGCATTCTTACCAGAGTAGGAATATAATGTTAGTCATTATTTAGAGGCCTG
        GCCATCTTGAGAAGGTTTACTGTTTAGTCTGCAGTACAATTATAACTGTTTTTGTATATT
        GGGTTATTTTTTTCAGAAGTAGGCCAGTAGCTCTAACAGGAGCCTCTTTAGCCTGAATTC
        [G,A]
        TCCAAGTAGTGCAGTGTTGCACTAGTTGTCCCTCGGGACATGCTCCCCAATACGTAACTC
        ACTTCCAGGTTGCAACTGGACACTTACTGGTAGTCAGAAATAGCTATTGCATGGAGCTTA
        AAATGAACTTGATCTTCGTGAAAGATGAGTCTGCAGCTAAGAGACTTTACTGTATATCAT
        AGTGTTTTTTTTGTTTTGTTTTGTTTTTGTTTTTGTGACGGAGTCTCACTCTTTCACCC
        AGGCTGGAGTGCAATGGCGAGATCTTGACTCACTGCAACCTCCGCCCCCTAGGTTCAAGC

29572   TCATAGTTCTTATGCACAAAGACCCTTTAATATTGTTTGTAAATTCTCCCCTATGCACAC
        GCTGACCTGTTCCTTAATCTTCTTATCTGTCTAGGTTTGGAGCAGGTATGTTAAGAAGTT
        AGGGGATTTTGCTAAGCCGGAGAATATTGACTTGGCCGTGCAGTGCCTGAATGAACTTAT
        AACCAATGCACTGCACCACATCCCAGATGTCATCACCTACCTTTCGAGACTCAGAAACCA
        GAGTGTGTTTAACTTCTGTGCTATTCCACAGGTAGGGAACGGGGCTCCTCTGGGTGGATA
        [C,T]
        GGGGCTAAAGGGAGTGGGGTAGGAGTAAGGGTGGATTTTGCTGTGCTATATTCAAGGATA
        TGATTCCTTAAAAAGACGATGACTCCAGTTTATTACGCTGGGAGTTTCATAGCACCCGCC
        TTTGCTTCCAGCCACCAAACTCAGCTCAGCCTTGAGGTTAAGCCTGCTCCTTTTCAGAAC
        CTTCTTTCCGGATTTACTATTTTCTACAGCTATCCTAAACTAGTTAGGTTCTTTTCCTCA
        CAGTTAAGTCAAGGTCTTTGGCTTAGATTTATGGGGAGTGCTGGGTAAAACCTGGGTGAA

29761   ACTGCACCACATCCCAGATGTCATCACCTACCTTTCGAGACTCAGAAACCAGAGTGTGTT
        TAACTTCTGTGCTATTCCACAGGTAGGGAACGGGGCTCCTCTGGGTGGATACGGGGCTAA
        AGGGAGTGGGGTAGGAGTAAGGGTGGATTTGCTGTGCTATATTCAAGGATATGATTCCT
        TAAAAAGACGATGACTCCAGTTTATTACGCTGGGAGTTTCATAGCACCCGCCTTTGCTTC
        CAGCCACCAAACTCAGCTCAGCCTTGAGGTTAAGCCTGCTCCTTTTCAGAACCTTCTTTC
        [C,T]
```

```
       GGATTTACTATTTTCTACAGCTATCCTAAACTAGTTAGGTTCTTTTCCTCACAGTTAAGT
       CAAGGTCTTTGGCTTAGATTTATGGGAGTGCTGGGTAAAACCTGGGTGAAGCTGTTATC
       ATTAAAAAGTCTTCATTAAGCACCTAATTACTGCTGTCCTTTTCCTAGACCCGGCATAAA
       AAGAACCTGGTCCGGTAGACCTAGCCTCTCAGTATGCTAGGAACTTACACTTTTTAGTTG
       CCTTTACCAAGTATTGCAGATACTACTGCAAATAAGTGAAGAAAGTAACAGCATTTAACT

30732  ATTCTGTGTGTTGTTGAGAAAGGGAGGAGTGGGGAAGGTAAAAATCTTGACATACTTTCT
       TCGTGGGTATTTTTTCTTGAGCGATTCCATCTTAGTTGATTAGCAGTTAGCAATTGCCCA
       TTCAACAGAAGGTTTTCTTACCTTTTTGTGATAATGATAGCTAACGACATCATTTCTTCT
       TTTTTCCCTCTCTTCTTGTTGTCTCTAGGTGATGGCCATTGCCACTTTGGCTGCCTGTTA
       TAATAACCAGCAGGTGTTCAAAGGGGCAGTGAAGATTCGGAAAGGGCAAGCAGTGACCCT
       [G,C]
       ATGATGGATGCCACCAATATGCCAGCTGTCAAAGCCATCATATATCAGTATATGGAAGAG
       GTGGGTTTTTATTTAACTACTTGGATAATTTGTAGCTACTTTTATGATTTAGTAATGTCA
       CTGTTTAACCAGGTTTGGATATTAGATGATCCTAACAATTCACTATCCTGTGGCCTAAAG
       AGACAGGAATTGATATCCTTTATAAGGAAAAAAGTCTATTCACAGGAGCCGAGCAGATTG
       CTCACTGCTGTGTAGTACCCTGGTGAGAGGAGATAAATGGAGCAAGGCTGTAGGTTGGAG

30841  GCAATTGCCCATTCAACAGAAGGTTTTCTTACCTTTTTGTGATAATGATAGCTAACGACA
       TCATTTCTTCTTTTTTCCCTCTCTTCTTGTTGTCTCTAGGTGATGGCCATTGCCACTTTG
       GCTGCCTGTTATAATAACCAGCAGGTGTTCAAAGGGGCAGTGAAGATTCGGAAAGGGCAA
       GCAGTGACCCTGATGATGGATGCCACCAATATGCCAGCTGTCAAAGCCATCATATATCAG
       TATATGGAAGAGGTGGGTTTTTATTTAACTACTTGGATAATTTGTAGCTACTTTTATGAT
       [G,T]
       TAGTAATGTCACTGTTTAACCAGGTTTGGATATTAGATGATCCTAACAATTCACTATCCT
       GTGGCCTAAAGAGACAGGAATTGATATCCTTTATAAGGAAAAAAGTCTATTCACAGGAGC
       CGAGCAGATTGCTCACTGCTGTGTAGTACCCTGGTGAGAGGAGATAAATGGAGCAAGGCT
       GTAGGTTGGAGCCCCTCAGTAGAATCATAGATTTTGAGCTGCAAGATGATGCAGGAGGCC
       AACCAAGCTTCTTGTTGCTGGTGAGGAATGTGAGGTTGAAGCTTGTCTGTGCTGATGCAG

31376  GAGGCCAACCAAGCTTCTTGTTGCTGGTGAGGAATGTGAGGTTGAAGCTTGTCTGTGCTG
       ATGCAGTGCGTGATTGAGTGGATCTCTGGCTCCCGTCCATGTGTCCTGACACCCAGTCTG
       GTACTTTCATTATGCCACAGGCCTCAATTGAAAAATCACAGTAGGGAATTTAGGCCAAGG
       AAAGCCATCAAGTTGCAATTATTTCCTAAATTTTCTTTGGAAAATTTCATTTCAAATACC
       AAAACCATCCTATAAAAGAAAACTTACCTTCTTAGGTCAAATCTCTAATATTTGACTAG
       [G,A]
       TTCAAAAAGTTTATTTCTGGCCAGGCACAGTAGCTTACTCCTGAAATCCCAGCACTTTGG
       GAGACCAAGGTGGGAGGATCACTTGAGGCCAGGAATTCAAGACCAGCCCGGGCGACATAG
       CAAGACCCCATTTCTACAAAAAATTTAAAAATTGTCATGGTGGTGCACGCCTGTGGTCCC
       AGCTACTCAGGAGGCTGAGGCAGGTGGATCACATGAGCCTGAGAGGTCGAGGCTACAGTA
       AGCTGTGTGATTTCATCATTGCACTCTAGCCTGGGTGATAGAGTGAGACTTTGTCTCAAA

32032  TCTCTAGGCCCTAGAGCAGTGGTTTGTAAATGGAGGTGATTTGCTCCCCTCCCCCCAGAG
       GACATTGGACAATGTCTGGAGACATTTTTGATTGTCCTAACCGGCAGGAATCGGGTGCTA
       CTGGCATCTGGTGAGTAGAGGCCCAGGATGATGCTGTGATCCTCAGGTGTGATCCTGTTG
       AGAATGAAACACTGTAGACTTTATGAAAACATACAAGACCCTCATCATTTTTCCTTTGCC
       TGAGCTCCCTCCCCAGAGGTTACCTCTGTTCATGGTTTTGTGCATCCGTCTAGTCCCCCT
       [A,G]
       TTACGCGTTTACAGGAATATGGTTTGCAACAGTGTTTTCATCTAAATAGAATTATACAAA
       ATAGCGATTTCTGATTTCTCTTGCATATTGCACATTCTTCTTATACTTCCTCCCTACCTT
       TATCTGACACAGAAATGCTGTATGTCCAGAACTTCTATCAGAGGCACCTATGGAAGTCTA
       AGGGAAGACCACATCGCTTTTAAAAACCCTAAAATTTTGTAGTCACTAGATGAAAATATT
       CAGCCAGTGACCCAAAAAATTGCTACCAATGAGACTCTCCATTTTGCCATGTAGCCAGAA

32525  ATCGCTTTTAAAAACCCTAAAATTTTGTAGTCACTAGATGAAAATATTCAGCCAGTGACC
       CAAAAAATTGCTACCAATGAGACTCTCCATTTTGCCATGTAGCCAGAACTTACTTTGATC
       TATGTGCCTGGGGTAGTGACCAAGTAGGTGGGTAGGAGTAATCTCAGGGAAACTTGAGGC
       CCCAGCCTCATGGCTAGGGTCATAATTTGAACCCAGGTCTGTCTGACATCAGAATCCATG
       ATGTTAACCCCAATTCTAAGGGGTTCAACTACCCTTTCTAAATGGAATCCTGCTATATTA
       [A,G]
       GCACTATTTATTCATTTTATATAAACTAGAAACATTTTATGTAGTAAGTAGTTGAGAGTG
       TTTTGGTTTTGCAGTTTGATCACTAGTTTTAGAAACCAGTTTTTAAACACTTTGTGGCCA
       ATTCCATTACTATATTAAAATTCAGATTTATTTGGTTTTTCCTTAACTATTGGGATTAAA
```

FIGURE 3, page 22 of 25

```
            TCCTGGTTGTAATTCATAGTTTGAGGGCGAGGGTGGGCAGTCTACATTTGGCTGAGCCCT
            GTTTTTGTGAATAAATGTTATCAGAACACAGCCACACCCATTTGCTTCTATGTCTTCTGT

34179   CTGCTGTATGTAGCACAGCATTGCACAAGAGCTTATTTCAGTCTAGTAAACATTTATAGG
            AGCCTGTGTCATTTAATCATCAAGCCTCGCACTGTGGCTCACACCTGTAATCCCAAAACT
            TTGGGAGGCTGAGGCAGGCAGATCACTTGAGGTAAGGAGTTCGAGACCAGCCTGGCCAAT
            ATGGCAAAACCCTGTCTCTACTAAAAATACAACATTTAGCCAGGTGTGGTGGTGCACACT
            TGTCATCCCAGCTATTCCGGAGCCTGAGACATGAGCATCGCTTGAACTCGGGAGGTGGAG
            [G,T]
            TTGTAGTGAGCTGAGATGGCACCACTGCACTCCAGCCTGGGCAACAGGGTGAAGGCCCTT
            TCTCAAACTCCTCAAGTATTTGGCTTCAACTTTATGCCGGGCATGTAGATGAAAAGTCGG
            CTATGACCTGTCCTTGACAAGCAGATGTAACTCCTTGATTGAGGCTAGTAGGTTTTTAAG
            ACCTGAATAATTGAGTTTGCAGAAACCTACTGTGTGCCTTCAGGTAAATGGAGAGTGGGG
            TTTGGTCTAGCAACGAAGCATCTAGAAGGTCTCTTTGGCCTTACCGGCTCTGTTTTAGGT

34249   ATTTAATCATCAAGCCTCGCACTGTGGCTCACACCTGTAATCCCAAAACTTTGGGAGGCT
            GAGGCAGGCAGATCACTTGAGGTAAGGAGTTCGAGACCAGCCTGGCCAATATGGCAAAAC
            CCTGTCTCTACTAAAAATACAACATTTAGCCAGGTGTGGTGGTGCACACTTGTCATCCCA
            GCTATTCCGGAGCCTGAGACATGAGCATCGCTTGAACTCGGGAGGTGGAGGTTGTAGTGA
            GCTGAGATGGCACCACTGCACTCCAGCCTGGGCAACAGGGTGAAGGCCCTTTCTCAAACT
            [T,C]
            CTCAAGTATTTGGCTTCAACTTTATGCCGGGCATGTAGATGAAAAGTCGGCTATGACCTG
            TCCTTGACAAGCAGATGTAACTCCTTGATTGAGGCTAGTAGGTTTTTAAGACCTGAATAA
            TTGAGTTTGCAGAAACCTACTGTGTGCCTTCAGGTAAATGGAGAGTGGGGTTTGGTCTAG
            CAACGAAGCATCTAGAAGGTCTCTTTGGCCTTACCGGCTCTGTTTTAGGTAAGTCCACGT
            CTGAGTACCAGTGACTGCAGCTCTTCCAGTTGTGCTGTCATGTTTATATGTTAGAAATGA

34451   GAGCATCGCTTGAACTCGGGAGGTGGAGGTTGTAGTGAGCTGAGATGGCACCACTGCACT
            CCAGCCTGGGCAACAGGGTGAAGGCCCTTTCTCAAACTCCTCAAGTATTTGGCTTCAACT
            TTATGCCGGGCATGTAGATGAAAAGTCGGCTATGACCTGTCCTTGACAAGCAGATGTAAC
            TCCTTGATTGAGGCTAGTAGGTTTTTAAGACCTGAATAATTGAGTTTGCAGAAACCTACT
            GTGTGCCTTCAGGTAAATGGAGAGTGGGGTTTGGTCTAGCAACGAAGCATCTAGAAGGTC
            [T,C]
            CTTTGGCCTTACCGGCTCTGTTTTAGGTAAGTCCACGTCTGAGTACCAGTGACTGCAGCT
            CTTCCAGTTGTGCTGTCATGTTTATATGTTAGAAATGATCATCAAAGGACTCAAAAGTTT
            TGCCACTAATTGTATTACCGGGGACTGTCACAACCAAGATTTCTCTTAATTTATTCACCT
            TACTTATCTCCTGGAAGGGCATATTGAAGTGCTCTTGGAGTTCTCTAAAAGGGTTTTTGT
            TGGTTGTGTATATTCACTTGGGTGCCAGCGATTGATTCCAAATAAGTAAATCTTTTTTCC

34532   AGGCCCTTTCTCAAACTCCTCAAGTATTTGGCTTCAACTTTATGCCGGGCATGTAGATGA
            AAAGTCGGCTATGACCTGTCCTTGACAAGCAGATGTAACTCCTTGATTGAGGCTAGTAGG
            TTTTTAAGACCTGAATAATTGAGTTTGCAGAAACCTACTGTGTGCCTTCAGGTAAATGGA
            GAGTGGGGTTTGGTCTAGCAACGAAGCATCTAGAAGGTCTCTTTGGCCTTACCGGCTCTG
            TTTTAGGTAAGTCCACGTCTGAGTACCAGTGACTGCAGCTCTTCCAGTTGTGCTGTCATG
            [T,C]
            TTATATGTTAGAAATGATCATCAAAGGACTCAAAAGTTTTGCCACTAATTGTATTACCGG
            GGACTGTCACAACCAAGATTTCTCTTAATTTATTCACCTTACTTATCTCCTGGAAGGGCA
            TATTGAAGTGCTCTTGGAGTTCTCTAAAAGGGTTTTTGTTGGTTGTGTATATTCACTTGG
            GTGCCAGCGATTGATTCCAAATAAGTAAATCTTTTTTCCCAAAAGGATGTAAGATGGCTT
            ATGGTTATAAGTACAACAGGCTAACAAAGTACAAGTAGATGAGAAAGTAAAATGAAGAAA

36541   GGTAGGAGCCAGTTGAAGGGACGTGGGAGGCGCATTCCAGAGAGAAGGAGTGGTATGAGA
            CTGGAACAGAGGTGTGCAGCAGCATCGCATGGGCGAAACAACAGTAGACAGTTGTTCTTT
            TGTTTTTGTTTGTTTTTGAGACAGGGTCTTGTTCTGTCATCCAGGCTGGAGTGCAGTGG
            CATGATCTCGGATCACTGCAACCTCCACCTCCCAGGCTCAAGTGATCTTCCCACCCCAGT
            CCCCAAGTAGCTGGGGGACCACAGGTGCATGCCACGATGCCCGGCTAATTTTTGTACATT
            [T,C]
            TGTAGAAACAGGGTTTTACTGTGTTGTCCAGGCTGGTCTTAAACGCCTGAGCTTAAGCAG
            TCTACATGCCTCAGCCTCCTGAAGTGCTGGGATTCCAAACATGAGCCACTGTGCCTGGCC
            CGGCAACTGTTACTAGACTATAGAGAGGGAGGTGGGCAAGGCTGGTGACACTAGACAGG
            TGCAGTAGGTCTGGACCATGGGTGGCCTTGCGCTACACATTACAGAGCTCAGGCTTTTTT
            TCTCCAGGTGAGAGGGCTGGTGCCACTGAGGCATCAAGCAGAGGTTTGAGATCTCCTTGG
```

36607	CAGAGGTGTGCAGCAGCATCGCATGGGCGAAACAACAGTAGACAGTTGTTCTTTTGTTTT
TGTTTGTTTTTTGAGACAGGGTCTTGTTCTGTCATCCAGGCTGGAGTGCAGTGGCATGAT
CTCGGATCACTGCAACCTCCACCTCCCAGGCTCAAGTGATCTTCCCACCCCAGTCCCCAA
GTAGCTGGGGGACCACAGGTGCATGCCACGATGCCCGGCTAATTTTTGTACATTTTGTAG
AAACAGGGTTTTACTGTGTTGTCCAGGCTGGTCTTAAACGCCTGAGCTTAAGCAGTCTAC
[A,G]
TGCCTCAGCCTCCTGAAGTGCTGGGATTCCAAACATGAGCCACTGTGCCTGGCCCGGCAA
CTGTTACTAGACTATAGAGAGGGAGGTGGGCAAGGGCTGGTGACACTAGACAGGTGCAGT
AGGTCTGGACCATGGGTGGCCTTGCGCTACACATTACAGAGCTCAGGCTTTTTTTCTCCA
GGTGAGAGGGCTGGTGCCACTGAGGCATCAAGCAGAGGTTTGAGATCTCCTTGGTGACAG
TGTAGAGCAGACAGGTAGATTTGGGAATTTAAGCTTAGACTCACGTTGGAGACTGAGATA

36681	GACAGGGTCTTGTTCTGTCATCCAGGCTGGAGTGCAGTGGCATGATCTCGGATCACTGCA
ACCTCCACCTCCCAGGCTCAAGTGATCTTCCCACCCCAGTCCCCAAGTAGCTGGGGGACC
ACAGGTGCATGCCACGATGCCCGGCTAATTTTTGTACATTTTGTAGAAACAGGGTTTTAC
TGTGTTGTCCAGGCTGGTCTTAAACGCCTGAGCTTAAGCAGTCTACATGCCTCAGCCTCC
TGAAGTGCTGGGATTCCAAACATGAGCCACTGTGCCTGGCCCGGCAACTGTTACTAGACT
[A,G]
TAGAGAGGGAGGTGGGCAAGGGCTGGTGACACTAGACAGGTGCAGTAGGTCTGGACCATG
GGTGGCCTTGCGCTACACATTACAGAGCTCAGGCTTTTTTTCTCCAGGTGAGAGGGCTGG
TGCCACTGAGGCATCAAGCAGAGGTTTGAGATCTCCTTGGTGACAGTGTAGAGCAGACAG
GTAGATTTGGGAATTTAAGCTTAGACTCACGTTGGAGACTGAGATAGCTCATCTGAGAGG
CACTCAGGGCCTAATCTCAGGCAGTAATTTTAGGGATGTAGGGGAAGAGATGGATTCTGC

37493	TGACGTTTATTGGGCCTGGCACTGTGAGGTGCTGGGGATGTGAAGATCATTGTGGCTCAG
CCGCTGCTCTCGAGGGCCTCTGGGTGCAGTATGCACACCTGTGCCTCCTGTTTGCTCAGG
AAGACAGGCTTTGAGATGAGCTGGGGCTGACATCCCCACCTTATCATTGGGATGGCTTTG
GGTAAGTTATGTTCATGTTCTCTGAGCCTCCCTTTCCTCATTGGTAAAATGGGTATAAAA
TACCTGCCAGTGGAGGGTTGTTGTAAGTAGCCATGGAAAATGTAAAGCACATAGCACTTA
[C,T]
CATTTTTTCCTGTGTCTTTAACAGATTTATCATAGAATCCCCGACTCAGACCCATCTTCT
AGCAAAACAAGGCAGATCATCTCCACCATCCGGACGCAGAATCTTCCCAACTGTCAGCTG
ATTTCCCGAAGCCACTACTCCCCATCTACCTGTCGTTTGTCATGCTTTTGGCTGCCCTG
AGCTGGCAGTACCTGACCACTCTCTCCCAGGTAACAGAAGACTATGTTCAGACTGGAGAA
CACTGATCCCAAATTTGTCCATAGCTGAAGTCCACCATAAAGTGGATTTACTTTTTTTCT

37966	CTGCCCTGAGCTGGCAGTACCTGACCACTCTCTCCCAGGTAACAGAAGACTATGTTCAGA
CTGGAGAACACTGATCCCAAATTTGTCCATAGCTGAAGTCCACCATAAAGTGGATTTACT
TTTTTTCTTTAAGGATGGATGTTGTGTTCTCTTTATTTTTTCCTACTACTTTAATCCCT
AAAAGAACGCTGTGTGGCTGGGACCTTTAGGAAAGTGAAATGCAGGTGAGAAGAACCTAA
ACATGAAAGGAAAGGGTGCCTCATCCCAGCAACCTGTCCTTGTGGGTGATGATCACTGTG
[C,A]
TGCTTGTGGCTCATGGCAGAGCATTCAGTGCCACGGTTTAGGTGAAGTCGCTGCATATGT
GACTGTCATGAGATCCTACTTAGTATGATCCTGGCTAGAATGATAATTAAAAGTATTTAA
TTTGAAGCACCATTTGAATGTTCGTACTAGTAGAAAATGATGTGAATTTTCTTTCTGTTC
GGCTCCTATTTTTCTCATCATTTTGTTTCTTTAATTGGGTTGAATGGAGTAGATAGAAA
TATTTATGGTTTAGGTAACAGTTAGATGTTTCCTAAGAATGCAAACTGCCTTTTCCACAC

37973	GAGCTGGCAGTACCTGACCACTCTCTCCCAGGTAACAGAAGACTATGTTCAGACTGGAGA
ACACTGATCCCAAATTTGTCCATAGCTGAAGTCCACCATAAAGTGGATTTACTTTTTTTC
TTTAAGGATGGATGTTGTGTTCTCTTTATTTTTTCCTACTACTTTAATCCCTAAAAGAA
CGCTGTGTGGCTGGGACCTTTAGGAAAGTGAAATGCAGGTGAGAAGAACCTAAACATGAA
AGGAAAGGGTGCCTCATCCCAGCAACCTGTCCTTGTGGGTGATGATCACTGTGCTGCTTG
[T,C]
GGCTCATGGCAGAGCATTCAGTGCCACGGTTTAGGTGAAGTCGCTGCATATGTGACTGTC
ATGAGATCCTACTTAGTATGATCCTGGCTAGAATGATAATTAAAAGTATTTAATTTGAAG
CACCATTTGAATGTTCGTACTAGTAGAAAATGATGTGAATTTTCTTTCTGTTCGGCTCCT
ATTTTTCTCATCATTTTGTTTCTTTAATTGGGTTGAATGGAGTAGATAGAAATATTTAT
GGTTTAGGTAACAGTTAGATGTTTCCTAAGAATGCAAACTGCCTTTTCCACACAAAGGCT

38113	TCTCTTTATTTTTTTCCTACTACTTTAATCCCTAAAAGAACGCTGTGTGGCTGGGACCTT
TAGGAAAGTGAAATGCAGGTGAGAAGAACCTAAACATGAAAGGAAAGGGTGCCTCATCCC
AGCAACCTGTCCTTGTGGGTGATGATCACTGTGCTGCTTGTGGCTCATGGCAGAGCATTC

```
        AGTGCCACGGTTTAGGTGAAGTCGCTGCATATGTGACTGTCATGAGATCCTACTTAGTAT
        GATCCTGGCTAGAATGATAATTAAAAGTATTTAATTTGAAGCACCATTTGAATGTTCGTA
        [C,A]
        TAGTAGAAAATGATGTGAATTTTCTTTCTGTTCGGCTCCTATTTTCTCATCATTTTGTT
        TTCTTTAATTGGGTTGAATGGAGTAGATAGAAATATTTATGGTTTAGGTAACAGTTAGAT
        GTTTCCTAAGAATGCAAACTGCCTTTTCCACACAAAGGCTGGGAATAAAATTCTGGGTAT
        TCTCGTATTCTCATTTAAAGGAGTTTAGCTTTCAGAGAGAAACAGCAGGATTGCTTTTGA
        CCTTTTAGAAGATTGGTCTCCAGTAAAGGTGGACATTTTTGAGATTTTTATAATAAAGAA

38298   CACGGTTTAGGTGAAGTCGCTGCATATGTGACTGTCATGAGATCCTACTTAGTATGATCC
        TGGCTAGAATGATAATTAAAAGTATTTAATTTGAAGCACCATTTGAATGTTCGTACTAGT
        AGAAAATGATGTGAATTTTCTTTCTGTTCGGCTCCTATTTTCTCATCATTTTGTTTTCT
        TTAATTGGGTTGAATGGAGTAGATAGAAATATTTATGGTTTAGGTAACAGTTAGATGTTT
        CCTAAGAATGCAAACTGCCTTTTCCACACAAAGGCTGGGAATAAAATTCTGGGTATTCTC
        [G,C]
        TATTCTCATTTAAAGGAGTTTAGCTTTCAGAGAGAAACAGCAGGATTGCTTTTGACCTTT
        TAGAAGATTGGTCTCCAGTAAAGGTGGACATTTTTGAGATTTTTATAATAAAGAATTTAA
        TTGCTCTGCATTTGTCAAGTACAGTTCGCTTGAAAGCCTGCCTGACTGTGGAAAAGATGG
        AGCTCAAGAATGGAGTTGATGGCCCAGCGTGGTGGCTCATGCCTGTAATCCCAGCACTTT
        GGGAGGCTGAGGCGGTCGGATCACGACATTAGGGGATCGAGACCATCCTGGCTAACACGG
```

FIGURE 3, page 25 of 25

SEQUENCE LISTING

<160> NUMBER OF SEQ ID NOS: 6

<210> SEQ ID NO 1
<211> LENGTH: 1606
<212> TYPE: DNA

-continued

<213> ORGANISM: Human

<400> SEQUENCE: 1

| gcgcctgggg | accgcagagg | tgagagtcgc | gcccgggagt | ccgccgcctg | cgccaggatg | 60 |
| gagttcgtga | aatgccttgg | ccaccccgaa | gagttctaca | acctggtgcg | cttccggatc | 120 |
| ggggggcaagc | ggaaggtgat | gcccaagatg | gaccaggact | cgctcagcag | cagcctgaaa | 180 |
| acttgctaca | agtatctcaa | tcagaccagt | cgcagtttcg | cagctgttat | ccaggcgctg | 240 |
| gatgggaaa | tgcgcaacgc | agtgtgcata | ttttatctgg | ttctccgagc | tctggacaca | 300 |
| ctggaagatg | acatgaccat | cagtgtggaa | agaaggtcc | cgctgttaca | caactttcac | 360 |
| tctttccttt | accaaccaga | ctggcggttc | atggagagca | aggagaagga | tcgccaggtg | 420 |
| ctggaggact | cccaacgta | ctgccactat | gttgctgggc | tggtcggaat | tggcctttcc | 480 |
| cgtctttct | cagcctcaga | gtttgaagac | cccttagttg | gtgaagatac | agaacgtgcc | 540 |
| aactctatgg | cctgtttct | gcagaaaaca | acatcatcc | gtgactatct | ggaagaccag | 600 |
| caaggaggaa | gagagttctg | gcctcaagag | gtttggagca | ggtatgttaa | gaagttaggg | 660 |
| gatttgcta | agccggagaa | tattgacttg | gccgtgcagt | gcctgaatga | acttataacc | 720 |
| aatgcactgc | accacatccc | agatgtcatc | acctacctt | cgagactcag | aaaccagagt | 780 |
| gtgtttaact | tctgtgctat | tccacaggtg | atggccattg | ccactttggc | tgcctgttat | 840 |
| aataaccagc | aggtgttcaa | aggggcagtg | aagattcgga | aagggcaagc | agtgaccctc | 900 |
| atgatggatg | ccaccaatat | gccagctgtc | aaagccatca | tatatcagta | tatggaagag | 960 |
| atttatcata | gaatccccga | ctcagaccca | tcttctagca | aaacaaggca | gatcatctcc | 1020 |
| accatccgga | cgcagaatct | tcccaactgt | cagctgattt | cccgaagcca | ctactccccc | 1080 |
| atctacctgt | cgtttgtcat | gcttttggct | gccctgagct | ggcagtacct | gaccactctc | 1140 |
| tcccaggtaa | cagaagacta | tgttcagact | ggagaacact | gatcccaaat | ttgtccatag | 1200 |
| ctgaagtcca | ccataaagtg | gatttacttt | ttttctttaa | ggatggatgt | tgtgttctct | 1260 |
| ttattttttt | cctactactt | taatccctaa | agaacgctg | tgtggctggg | acctttagga | 1320 |
| aagtgaaatg | caggtgagaa | gaacctaaac | atgaaaggaa | agggtgcctc | atcccagcaa | 1380 |
| cctgtccttg | tgggtgatga | tcactgtgct | gcttgcggct | catggcagag | cattcagtgc | 1440 |
| cacggtttag | gtgaagtcgc | tgcatatgtg | actgtcatga | gatcctactt | agtatgatcc | 1500 |
| tggctagaat | gataattaaa | agtatttaat | ttgaaaaaaa | aaaaaaaaaa | aaaaaaaaaa | 1560 |
| aaaaaaaaaa | aaaaaaaaaa | aaaaaaaaa | aaaaaaaaa | aaaaaa | | 1606 |

<210> SEQ ID NO 2
<211> LENGTH: 374
<212> TYPE: PRT
<213> ORGANISM: Human

<400> SEQUENCE: 2

Met Glu Phe Val Lys Cys Leu Gly His Pro Glu Glu Phe Tyr Asn Leu
 1               5                  10                  15

Val Arg Phe Arg Ile Gly Gly Lys Arg Lys Val Met Pro Lys Met Asp
            20                  25                  30

Gln Asp Ser Leu Ser Ser Ser Leu Lys Thr Cys Tyr Lys Tyr Leu Asn
        35                  40                  45

Gln Thr Ser Arg Ser Phe Ala Ala Val Ile Gln Ala Leu Asp Gly Glu
    50                  55                  60

Met Arg Asn Ala Val Cys Ile Phe Tyr Leu Val Leu Arg Ala Leu Asp

```
65                  70                  75                  80
Thr Leu Glu Asp Asp Met Thr Ile Ser Val Glu Lys Lys Val Pro Leu
                85                  90                  95
Leu His Asn Phe His Ser Phe Leu Tyr Gln Pro Asp Trp Arg Phe Met
            100                 105                 110
Glu Ser Lys Glu Lys Asp Arg Gln Val Leu Glu Asp Phe Pro Thr Tyr
        115                 120                 125
Cys His Tyr Val Ala Gly Leu Val Gly Ile Gly Leu Ser Arg Leu Phe
    130                 135                 140
Ser Ala Ser Glu Phe Glu Asp Pro Leu Val Gly Glu Asp Thr Glu Arg
145                 150                 155                 160
Ala Asn Ser Met Gly Leu Phe Leu Gln Lys Thr Asn Ile Ile Arg Asp
                165                 170                 175
Tyr Leu Glu Asp Gln Gln Gly Gly Arg Glu Phe Trp Pro Gln Glu Val
            180                 185                 190
Trp Ser Arg Tyr Val Lys Lys Leu Gly Asp Phe Ala Lys Pro Glu Asn
        195                 200                 205
Ile Asp Leu Ala Val Gln Cys Leu Asn Glu Leu Ile Thr Asn Ala Leu
    210                 215                 220
His His Ile Pro Asp Val Ile Thr Tyr Leu Ser Arg Leu Arg Asn Gln
225                 230                 235                 240
Ser Val Phe Asn Phe Cys Ala Ile Pro Gln Val Met Ala Ile Ala Thr
                245                 250                 255
Leu Ala Ala Cys Tyr Asn Asn Gln Gln Val Phe Lys Gly Ala Val Lys
            260                 265                 270
Ile Arg Lys Gly Gln Ala Val Thr Leu Met Met Asp Ala Thr Asn Met
        275                 280                 285
Pro Ala Val Lys Ala Ile Ile Tyr Gln Tyr Met Glu Glu Ile Tyr His
    290                 295                 300
Arg Ile Pro Asp Ser Asp Pro Ser Ser Ser Lys Thr Arg Gln Ile Ile
305                 310                 315                 320
Ser Thr Ile Arg Thr Gln Asn Leu Pro Asn Cys Gln Leu Ile Ser Arg
                325                 330                 335
Ser His Tyr Ser Pro Ile Tyr Leu Ser Phe Val Met Leu Leu Ala Ala
            340                 345                 350
Leu Ser Trp Gln Tyr Leu Thr Thr Leu Ser Gln Val Thr Glu Asp Tyr
        355                 360                 365
Val Gln Thr Gly Glu His
    370

<210> SEQ ID NO 3
<211> LENGTH: 40090
<212> TYPE: DNA
<213> ORGANISM: Human
<220> FEATURE:
<221> NAME/KEY: misc_feature
<222> LOCATION: (1)...(40090)
<223> OTHER INFORMATION: n = A,T,C or G

<400> SEQUENCE: 3
tatttattcc taattaaatg gggaggaaag tctttgaaga ggaacctcta ctttactttt      60
tataccgtca tggctggaaa ctaagttttt aagattttc tggggttccc ttggccgagg     120
tggggagtgg gagggctgtc cagtggtagg gacttaggat ttttagttta cagtagtagg    180
ggaaacactc tgtaatctaa tacataagta aatgatgtat tagaatatgg taaatatagg    240
```

-continued

| | |
|---|---|
| caagtagacc cccactggga ttagcagtgg tggaaatgtg agagagggca aacaggtggg | 300 |
| tctagatgag gtgtgagcag actcgagggg cacaggagtt agtcaagcca gtatctgggg | 360 |
| gatagtgcag gaatagtgaa cagctagaca aaaagtccta gggccagaga agcaaaagc | 420 |
| ataagagatg gaggccagag aggtaatctg ggtggaaggc tgcagcctct caggatccct | 480 |
| ataggtgctt tggcttttgt tggagagaca ctgaacagct ttgggcagtg aacgtacctg | 540 |
| acaggtttcc tgtttgtttt tgagatgaag tctcgctctt gtcccccagg ctggagtgca | 600 |
| atagcgcgat ctcagctcac tgcaacctct gcctcctgtg ttcaagcgat tctcctgcct | 660 |
| cagcctccca ggtagctggg attataggcg cctgccacca tgcctggcta attttgtat | 720 |
| ttttagtaga gacgcagttt cagcatgttg gccaggctgg tcttgaactc cagacctcag | 780 |
| gtgatccgcc cgccttggcc tcccaaagtg ctgggattac aggcgtgagc caccgcgctc | 840 |
| ggctagacct gacaggtttt aaaaggatta ctggttgctg tgttaaaaca gactgcagga | 900 |
| tgcttaggt agccagtagg ttttttttt ttttggagac gtagtcttgc tctgttggcc | 960 |
| tggctggagt gcagcggtgt catcttggct cactgcaaac tccgcttccc gggttcaagt | 1020 |
| gattctcctg cctcagcctc cggagtagtt gggactacag gcgcccacca ccacactcgg | 1080 |
| ctttttttgta ttttagtag agacgggttt caccatgttg gccaggatgg tctcgatctc | 1140 |
| ttgacctcgt gatccacccg ccttggcctc ccaaagtgtt gcgattacag gcgtgagcca | 1200 |
| ccacgcctgg acgggtagcc agtagtttct agggctggag agatctagga tgagagaagt | 1260 |
| ttccacattc ctgttacagg ctctctaagg cttcagctcc tttttctagg actaagctgg | 1320 |
| atctcaagta aacactagag agggggcagc tgaagctcca ggagtgtgtg gggctccctg | 1380 |
| gggctggatg gcggtggcgg gcaggcgagc tgggctgtgc tcgggtgtgt tacagtaaag | 1440 |
| acgcccagct tggcgctggc ccggcctttt cacggtttta ggctctacag agagcggctg | 1500 |
| cagagctcac ccgctggca ggagccaccg aggccggaca cgtgggcgac ttattgacca | 1560 |
| agtggggagg aagcagcccc gcactgctct cccgactgcg gaccaccgtt gggctcatgc | 1620 |
| gcatcataag ccccaccgcc tcacctccag tccccacagc gttcgcgctc ccagccgggg | 1680 |
| taagcggaag aaaacaaagg cccggctcca tcagggcacc aatcccgctc gtcggcctct | 1740 |
| ttctcggcct ccaatgagct tctagggtgt tatcacgcca gtctccttcc gcgactgatt | 1800 |
| ggccggggtc ttcctagtgt gagcggccct ggccaatcag gcgcccgtca gcccacccca | 1860 |
| cgaggccgca gctagcccg ctggcggccg aggccggttg aagtgggcgg agcggcgggc | 1920 |
| ggggcgtcgc cgtactaggc ctgcccctg tccggccagc ccctcgaagc acctactcca | 1980 |
| caggtccagc cggccggtga gcgcctgggg accgcagagg tgagagtcgc gcccgggagt | 2040 |
| ccgccgcctg cgccaggatg gagttcgtga atgccttgg ccacccgaa gagttctaca | 2100 |
| acctggtgcg cttccggatc gggggcaagc ggaaggtgat gcccaagatg gaccaggtgg | 2160 |
| gccgagcctc cctgcttgcc cggggcgggg aaggagctcg ctgggccggc ctcagggcct | 2220 |
| gagcggccgg gccggatct ggggcaaggg gcgcggcgag cagggccgac gcctgggtgt | 2280 |
| tcccgtcccc ctttcctcga gccttccccc tgtagggccc gggtggacgc ggccgtcctg | 2340 |
| gctgacctgt ccctgccccc gcaagccgcc ctgggcatga gcgacttttg cgtggttccc | 2400 |
| ggtggttgcg ctccccgttt cgtcccctcc gtgagcatcg gcgcttaccg gtattttaac | 2460 |
| ccgagggtta cacatctgag gcaatgtggg tgggttacgc gggagaggac gagtgagttt | 2520 |
| tttggtaagc ggaatgaact atgcagataa catcacatga aggccgtttc tggaatgaag | 2580 |
| tctgactcct ccagtttcac cacctcttcc ggagctctcc ccgccttgct gccttccatc | 2640 |

-continued

```
gcttcatcct cggtgcttcc tgagttttaa aatcgcctat ctacgcttcc aagttccaat    2700
gagttatcta acgtctatgg attagctagg tggttggtgg aaggtcagaa cttggtttta    2760
cttagatttt tatctgcctc atgcctgtac tatttgttta atgaatgcat aggaggtgtt    2820
tttattccaa caagaaaatt attcgtacgc gattattgaa tgaatagaca aattcagcca    2880
agttcttctg gtctggacca gcctggctga tttctgtaac ttttttgggc aacaggaca    2940 gtagcaaatg tgactcaggc cgaggcttga taggtgcctg aacatcggag tctttctttc    3000
agtgtccatg tgcttcagta aacacactag aaaataaatt tctggttttt gtccccagta    3060
gactacaccc tcatttggtg ttatttttca cgtgctatct ttaatacagg tacatccttc    3120
agtctatttg tagaacattc agttttcttc atcttttctt tgccggtgct acattatttg    3180
aattattttg ctacagaata acttctatta tttgatatgg cagatgtcac ttttttatatt   3240 tagatatagc attcatttat ttaacaaata tttgacgacc agttgtatat cagatagtgt    3300
tctaggtgct ggaggtacaa cagtgaacaa gctaggtgaa gaccttgatt ttataaaact    3360 tacttttag tggaagagag acaatttaaa aaagcgaatg tacagttttt cacgtggaga    3420
aaagcactgc agaggaagat actagcaggg caagggatct gagtgcagtc agacctcatt    3480
tgggtccaga cttcattcct ctatgtctct ttcctttcta cagaaagact gttagagaaa    3540
atggtagcat tggtttcctg ttgggaggga aagtgggtgg tcatggtaag tgggtagaga    3600
aagacttcac agtatactgt ttttgtacat tttgagtttt tttaaaagcg agacttgagc    3660
tattctagct ctgataatat ggtgcagtat ttgttatgtt agttgtagtc tttctgggca    3720
gtttttacat ccccatgagc cgttaaaaaa atacctgaac ctttaattag gggaaataaa    3780
ttggaaaaat acatttccct tcacttaaca ttatcttagt ttctctttt tttttttttt    3840 tttttgaga tggagtcttg ctctgttacc caggctggag tgcagtggtg gcgggacctc    3900
agctagatgc agcctccgcc tcctgggttc aagcaattct cctgcctcag cctgctgagt    3960
agctgggatt acaggcacct gccactacgc ccggctgatt ttttggtatt tttagtagag    4020
acggggtttc accatgttgg cgaggctggt tttgaactct tgacctcaag tgatctgctc    4080
gccttggtct cccaaagtgc taggattaca ggcgtgagcc actgcacccg gcctttttt    4140 tttttttt gagggggggg tctcactcca tcgtccaggc tagaatgctg tggcctgaac    4200
atgactcact ccagttttga cttccttggc tgaagccatc ctcccacctc ggcttcctga    4260
tcccgagtag ctgggactcc aggcacgtgt caccaatgca tggctaattt ttaaattttt    4320
ttgtagacac aatgtctcgc tgcattgccc aggctggtct tgaactcctg agctcaagcg    4380
attttcccac ctcagccttc aaagtgctgg gattacaggt gtgagccact gcacccaacc    4440 agttctctc tgcaaactag ggaaaaaatt tacgcttagc agatattgag ggctgattat    4500
ttctatcaca gaagcatttg gctatagaat ttcagggttt agtaaacttg atttacactg    4560
aatttttagg tgcatatcag taaatctacg ggcatatgcc gcctgcaagt tgtgtggcat    4620
cacccaaaag ccgagagtaa tggaaagagc aggctgttag taatcaggca gatctggctc    4680
ctgtccaatc taaatcctgt tatttagact aatatcttaa gtctgttatt aagtccgatt    4740
tctgacgcta ttaagttagg tgaacaacct tggtaactta acctctgaac cacagttact    4800
tcatctgtaa aatagggatg tatgtatggt aacgattttt taaccacaac ttcccaactc    4860
taagatggtc tgaaaagaat tttttgagtg tttggctcag aatcacttgg cagcaaaacc    4920
tgacttgaag ttgaggcttc attcatccca cttagtatat tcaaatgttt tgctaaagaa    4980
```

```
ataattatga ggtgctactt cacactgact agggttgtat atgcatttta ttgcctattt    5040
tctaaaacac taaaaatgct aaattctgcc ccaggtcttg ccacagatgt ttcagtggac    5100
tatgggcctg tgagacctta aagggttgat tgagtaagga tcacaggtga tgtccgcatt    5160
gtgcttggca tggagttaag tgcttgataa atggtggtta tcaatctgat tatgtaaatt    5220
tatgtaaatt cagttctcaa gtttgtggtt ttttcccct cctggagaaa tctattctat     5280
tttaaagtga ggaaggctcc gtggagggct ggtagctggt agctgttcac ttgtggaact    5340
ttcagcctga ggctggagcc ccttcctggg agtctggtct tgtcgtcttc ctgaccaccc    5400 ccacacccctt cctctaaatt ccctccatcc ctgtttttct cccgcttgcg agcttttggg   5460
agtgtgctga atctcagact gcaatagata acccaagag ggacaggcac cagtagcctg     5520 agcttgctttt ctcccctggc tcatgggaat caagcagtag aaatttttag tgagtgttgt   5580
tttccatagt atgcttacta gttgtgtctt cctgttttgt tcttggtgat ttgaagaaac    5640
ctgtttacaa ggtaagggac tgaaacaaat aggtgacagg aaaagagca gcagggtac      5700 gagctggagg agtaagtggc ttggcttgct ctctttcaga atggagggct gtatggaaag    5760
gaggggtagt gttcttgaag agtgttgggg tttaaatcta gggggaccgt gtcttggcat    5820
tgattgaaac tcctggctta acatcacccc gaaactgtta gttggactga acatgacatt    5880
tggcagtgca gttaaaaaca cttcctgctg tagcctggta atggtcaggc tatgtgaaga    5940
gctgctctgg agctcagtcc agagcgggta ttctgttttct ttcactctga aatcctgcct   6000
ctcgatattt tgagaaggaa ggagttggtg aattgtttta aaatcctcga tgaatgtctt    6060
catttattca tgacaccact tctgaatata tttatgtgcc agacgctgaa gtttactaat    6120
attatggtgc ccagtaaata cttgtttta ctaatatttt ttatggcaat aaaatgactt     6180
tttcaggatt atgtgattta aagattgac cctttggca aaatacgtat tcatgatagg      6240
aaatatatac aacatagttc acttaaacct cccaccagag cccagggttc actgttacca    6300
ttctgaagtg actggaattt cctagaagtg gatatgccat atttttttaa ccactcctat    6360
tggatatttg ttttttattt ttttgagatg gggtcccact ctgcagtgta caatatcata    6420
gttcactgta acgtgtatct cttgggctca agcgatcctc cccacctcag cctccctgag    6480
tagctagtct tcagtagcta gactataggt gggcgccacc acagctggct tttttaaaaaa   6540 ttttttatga acacgaggtc tcactatgtt gcccaggctg ccctcaaact cctgggctca    6600
agtgattctc ccaccttggc cttccgaagt gcagggatta taggcgtgcg ccactgcacc    6660
cggccctgtt ggataaatga ttccagtctc tcccaaaaag aactgttgta agactgtggg    6720
gtgaggggag ggaagggaca aataggaacc cgccgtattt tccactccct gtgggcctaa    6780
aactgctcta aaaaatagtc catgaaaaaa tacatagtac aaacagcaac tctttctgat    6840
atgcttgcat ttaaaatcag gctttttctc ccttttggaa aaacacagtc cttgtttgct    6900
ttagggaaga gtaaaggtca gtgcgctgca ttgcattaat ttcgaaggga aagatgagaa    6960
gacatcttga aaggaatggc tggctttcta gagaatagta gaggcttaat aggtgtcata    7020
gaaaaaccag ggttggacag tggtagtaaa acggcaaaac agattttatt cagaaaaact    7080
actgcagtaa gaggagagag acctcggtac agaactgctc cactgcgaat acaaagaaaa    7140
gtaggaattg atggcggggg agccggatgt cagtggatgg aaaattatta cgaggaaaca    7200
caggggtgtg cattcttgct gaaggcaggc cagagttatc agacatcacc tgagggatgg    7260 aggggatgt ggaacctaat cggctgtcta gggtgatcag atactgaagt tgggggattc     7320
tggtcaaatc aatttagcag gattcttggt aaaactgggc gatgcaaaga cagatgcgtt    7380
```

-continued

```
gagtacaaag tccaggcttt attgggaaga ggatttcagc ggagcccgag tagagtttgg    7440
tctagggaga ctctgtcact ggaggacga gcgagccgct cggaagtgcg ctgggttctc      7500
ttagcggcca gtgggttctg gtgagaaggg caacagcggg aggaggcgcc ggtgcggagc    7560
gggaggccgg gggcggggct gcggggctgc ggggcgggcc cgttgtgggt cggcccagcg    7620
cgtattcgag tagagggcga gcccgtcccg cctctcgtcg ggcgcttccc agatctgctt     7680
gagtctatgg aggaaaaact ccgcggggtc cgcgattccc atggccgcag ccgcctgcgg   7740
caccaaggcc atggccctct tcaagcgcac cttggtgctg agtcccgccg cggcgcccag    7800
gggcccgggc gcaggcaccg ccccgcgggg ctgctgcttg cctcctgccg cctggccctg     7860
caaggactgg cctcggggag agggcggcag gctgtggagc cgcctgcccc agtcccagtc   7920
ccactcccac tcccactccc actcccactc ctgctcctcg acgtctccca ccgccgtgtg      7980
tgttgtctgc ccgcaggact cgctcagcag cagcctgaaa acttgctaca agtatctcaa   8040
tcagaccagt cgcagtttcg cagctgttat ccaggcgctg gatggggaaa tgcggtgagt    8100
gatggaggca gcgcctctgg cttggaggaa agcttgtccg ggacttttga gtgtgttgga      8160
agctaccttt tgatatagcg ctcagcgttg cagcctcgtt gctgtggctt atccagaaca     8220
tagcccggcc ctacgtgttt actttagaaa gcccttccag gctctttgcc atctagtaga    8280
gtccctgcgg gcccagcctt tcagagaagg gggggaggg ggtgatgttt attaactttt      8340
tttagtcttg gcagctgaac ctgcctgtga gcaggtcgtg tatttctcgg cttcccttat        8400
ccaactttgc atttctattt ctagcatatt gggttgattc ttttgaagct gcctctgtgc        8460 acattcacc catgaactta gaccagttgc ctttatgtat gatcgtattt atactgagaa     8520
gttactgtgt ttttttgactt tcttttctat ttgctacata ttagttcggt ctaaacgttt       8580
ggtcttctgg tctccatagt tctacattgg ttaaatgcaa ctcacttctg ggagtagtgg   8640
tgacattcaa ctagtaggct tttttaataaa ctacagaagt tcattactct catgtaagga    8700
aggaaaacta atgtaacttt cgttaagtat gaaaagcgtt ggatatcctt atagttcttt        8760
agagttaagg gtgagatggg tttagaaagt ggccaggcac aagttatttt aaaataaaaa   8820
atctttggct gtttgttcca atatattaat agttttccct tttttacagc aacgcagtgt        8880
gcatatttta tctggttctc cgagctctgg acacactgga agatgacatg accatcagtg     8940
tggaaaagaa ggtcccgctg ttacacaact ttcactcttt cctttaccaa ccagactggc    9000
ggttcatgga gagcaaggag aaggatcgcc aggtgctgga ggacttccca acggtgagtg   9060
gggttacgca tcttgtctac ggactgttgt gttcataatt gctaacgtgg ttgtccggta      9120
gcctccatac atgtggagaa aggttaaata agcattctga gggcagcata atgtgagggt  9180
taaaaactcc ggtagccaag actctgaagc caggctgcct gggttggaat ctcaaatctc    9240
ccacttacta aactgttggt tacttacaaa gactctctgt gcctcagttt cttcatctgt         9300
aaaatagggg taataataac acctacctca tggtattctg aggattcaaa gaattaacgt    9360
aggtaatgct cttagaatgt tagctactgc tgttattatc agtattggaa gtccagtgtt      9420
tcttcctgtg ggaagacgca gtcaaatttt agtgttgtga aagattctca ggctagctca   9480
caaaagcctg ccgactgtat gatgcagcct acctgtaaca ctgctggcct cttgactacc      9540
cggagcctgg tagcatggga ctgctgctca cgatgggcag cagcctggca tggggcggt  9600 gtctgttggc agctagggcg agcctctgcc acttcacctg tgatcctggg caagttcctt    9660
atctgctttg tgtctccgtc tcctcgtttg taaagttaga gctgagagga ttaatttcgc    9720
```

-continued

```
acatataaag tacttagtgc ctggtacagg gtaagtattc tgtaagtatt agctatttgg    9780
tctattttgt tggagtaaag tgggttatag ttaaaatcct aagattttta aagtccctca    9840
agttcacgtg gacatctgcc taggtcctac tatcctagaa ttcgcatgtc ttatcacaca    9900
aataactgat tcttccatat cttataaata aaggtttgat ttagcaaagt cacatgttgt    9960
gtaatagctc gaagaagccc tttttgtcca cagttgccag agcttttgga gaacagtcct   10020
tatgttattg aaacaaacct aatctgtagc tgagttggga gggagctaag tggacagaga   10080
gtcctccacc caaacaaaag aatctttgat tcttgggcat aatgggagca atatttaaaa   10140
aaaaaaaaaa aaaaaaaaaa ggaatgtttg gggaagactc ttgcggtgca aaggctgttt   10200
cagattgctg agatcagacc ttaagtacca agcccaaat atagtacaac ataatacaaa    10260
tgagaagaaa atagctgaag aataattcga gtttatacag tacaattcaa gagaagaaag   10320
aaaatttatg acgactagct gggtgagaat tagaactgta accctgggaa ggtcctggtg   10380
atttgactct cacaggacac ctgatgacca gaggatgggt ttcctttgat gggaaatctg   10440
tggcgattca ttgatgggcc tctgaattct gctgaagcag aggaagtagt aatacccat    10500 ttataatgga agtgcattct cacttaaaaa caactaatat tattctagct ggacctagcc   10560
tctagaaaca gccaaattac atttgacttg agtggattca taataattaa aaaatttctg   10620
gggcatggga taaatgtgtt aggtattgct aagtcaaggc agccctatcc cctcagcaga   10680
agtgagggaa tatgaaagtg tgtgaatgct aacataattt tggggaatat cgccgtcaga   10740
tttccagatg atattccaac atgtttgtga aacttcagtg tcttcctgtg ttcatacagt   10800
gttccagtgg aaaaataatg cttagttctg gaaggtttca gatgtgaaca ctgaactcat   10860
cgttttcttt tttgggtagt agagttagag attccatcct cttgaaagca cagttgcccc   10920
gggaagagta aagggagca gaaggcgtaa gccaggcacg gctgttttca ctgttgttca   10980 cctttttgtat ccttacgaat atgaagatgt actaagttgt gtgttttgcg tgcatatata  11040
attttaagct acttgagttg taggtccctc cagtctgtga ttcagtttga gatgggactg   11100
tatgggaatt aacagtgcct tgtcttctta agcagtgatt tgtgtatgtg ctgatatagc   11160
tcagtatgtc tttgaaacca gttgtctggg gctaggcctg caatcagctt ttggctaaga   11220
ggtcccagga tggaacaagt agtgtgaaag aggactgata ccttggcctc acacacagta   11280
ctgctcttag actggggcaa gtgaaactcc tcacttcaga gtgccccatt ctaggccccc   11340
tcactcccaa aggggtgagg gatcactggg gccatgggaa tgtgcttgtt cagctctcgt   11400
gggctctcct tctgtaccac gttctggaca tctggagttc cttgccccaa atccctgagc   11460
ccacgtctgc gtccgcacag tctatttcct aaggtcagtc catctcctcc aggtgggaac   11520
gtgccaccat tgactgtgcc cttgggcctg agtgatggcc aagggctgtg ttggggagtg   11580
ttgtggatgg atcctggcac cgagggctgg gatatcctct caaatgaatg tgaggtgcct   11640
cccagtgctg gagagagcgg gattcaggaa gcagtggaag ggaagagcct gggatatggg   11700
gatcagctgt ctgtgccctg ctgcattctg gaataaaact ctgagggact aagaattcta   11760
aattcaaacc tgaatcaacc aggttgttac aaagataagt ttgtcagtgc aggaggatac   11820
aatatatttt acttaagtta ctagctcgat tgatcatttt taaattttta gctacatata   11880
gtatgtgggc ctccatttgt cctcttatcc caggccttgc agaatttagg aataagcctc   11940
aatacagtgt tctaacccag tgacttccgc ctcgatgtac agtagattga acctgatcct   12000
ttatacttta gtgatcatta gttgatacca gttcaagtca ggctttctag aaatctcatt   12060
gtatgttagg ggttcgatta gagtacagtc atgcatcact taatgaatgg ccacaggata  12120
```

```
cattctgaga aacgcattga tagatgattt catcattctg tgaacatcat agagtgtact   12180
tacacatacc aagatggcat agctactaca gacgtaggct ctgtggtaca ggccattgct   12240
ccaaggctgc acatctctac aggatggtac tgtactgaat actgtaggca attggagcac   12300
agtggtaagt atttgtgtat ttaaacatag aaaaggtata gtaaaaacag ggtgttacag   12360
tcttaagggc ccaccattgt atttccagtc tccgttgact gaaacatcat tatacagtac   12420
atgagcacgt atctttctca cctggtacta gtggaaagct agaaggctta gaagtctacc   12480
tgtaaacata gcttaagtaa taatacagcc ttatttttaa atgataatag caataatagt   12540
gttcacttat tgagcatttt actatgagtt acttactaaa tatatttcat cgttaattta   12600
ctctttgtgt tatttgatct ataacatcgt ttaacaggga aattacctag tacataatgt   12660
actgttatct acattttatc tagatgagga aactgaggca cagagaaatt aagtactttg   12720
cctaggatta cccgtgaagt taagtgacag aatcaatgaa tctggaaggt ctggcttcag   12780
atctcttgtg ctgagtcact cgcatacttt actacctcta aggtttctaa tcagaggaat   12840
ttgtatctgt attccctgct actcttaccc tctatgtggg atttggcctt tctccattat   12900
ccctgtgaac tcgctctggg accttccttc ttgtacttgg aaccatcaga agtgatctg    12960
agaacataga aatctactgt gttgtgaaac agaattacct ggaagcggaa aaagccctcc   13020
tggctcaatt cacatgtcac ggcttatggt cgtatccggg gaacatatga aactgggcac   13080
tgagtgcgga gtcaggaaag ccctgtccat cctctgggtt tctggggaaa acgtggaccc   13140
cttcattgtc actttctcct gtatattttt gttttttactt ttagaactgt acaattacgt   13200
aataaataat aaaagtcgt tggaaggata ggtgaagttc agaagtgaaa gtgttttgga   13260
ggagtctaag ctccttccca ccctcattga cctttcctct ctaataaata gaactggtct   13320
aaccaaggat ctgtggaatg agcagagtcc aacggagatt cagggattct aataacctct   13380
tgtagaatca ctggtttgtt tcagccacaa gaaggaatta ccttttgaca ttggcttgaa   13440
cagctgttgt gcaaagaaaa acttttggaa aagttctgga agtaccagat tgattttata   13500
ggttttttt ttttttttg gagggacatg ggggtattga cagttgatgt taatcagaaa   13560
tcctaaatta tgtgtattcc tggtatgttg caatcagccg gccacctggt tttcctctgg   13620
gctcttaatt ttaggtgtat tccgaggaag tttttctaac ttttctgtaa acacagacca   13680
ggtatattgc atactttcaa tgtttaacca aatctcttca ctgtttgcag tattatctgt   13740
aggctctcat gttttaagac ttccccatgg tgtttttgta ttgtattttg ctaacctata   13800
aacaattctt tgaacttaaa acaagatatt tgggcagtaa caataaattt taaaaacatc   13860
aattcaactt ttttacatta gggcttggac tatggaaaaa gtattgggca gcatgcctca   13920
tactgagttg tttaatgaat ttaaaagtat agccnnnnnn nnnnnnnnnn nnnnnnnnn    13980
nnnnnnnnnn nnnnnnnnnn nnnnnnnnnn nnnnnnnnnn nnnnnnnnnn nnnnnnnnnn   14040
nnnnnnnnnn nnnnnnnnnn nnnnnnnnnn nnnnnnnnnn nnnnnnnnnn nnnnnnnnnn   14100
nnnnnnnnnn nnnnnnnnnn nnnnnnnnnn nnnnnnnnnn nnnnnnnnnn nnnnnnnnnn   14160
nnnnnnnnnn nnnnnnnnnn nnnnnnnnnn nnnnnnnnnn nnnnnnnnnn nnnnnnnnnn   14220
nnnnnnnnnn nnnnnnnnnn nnnnnnnnnn nnnnnnnnnn nnnnnnnnnn nnnnnnnnnn   14280
nnnnnnnnnn nnnnnnnnnn nnnnnnnnnn nnnnnnnnnn nnnnnnnnnn nnnnnnnnnn   14340
nnnnnnnnnn nnnnnnnnnn nnnnnnnnnn nnnnnnnnnn nnnnnnnnnn nnnnnnnnnn   14400
nnnnnnnnnn nnnnnnnnnn nnnnnnnnnn nnnnnnnnnn nnnnnnnnnn nnnnnnnnnn   14460
```

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 14520 |
| nnnnnnnnnn | nnnnnnnnnn | nnnnnnnnnn | nnnnnnnnnn | nnnnnnnnnn | nnnnnnnnnn | 14580 |
| nnnnnnnnnn | nnnnnnnnnn | nnnnnnnnnn | nnnnnnnnnn | nnnnnnnnnn | nnnnnnnnnn | 14640 |
| nnnnnnnnnn | nnnnnnnnnn | nnnnnnnnnn | nnnnnnnnnn | nnnnnnnnnn | nnnnnnnnnn | 14700 |
| nnnnnnnnnn | nnnnnnnnnn | nnnnnnnnnn | nnnnnnnnnn | nnnnnnnnnn | nnnnnnnnnn | 14760 |
| nnnnnnnnnn | nnnnnnnnnn | nnnnnnnnnn | nnnnnnnnnn | nnnnnnnnnn | nnnnnnnnnn | 14820 |
| nnnnnnnnnn | nnnnnnnnnn | nnnnnnnnnn | nnnnnnnnnn | nnnnnnnnnn | nnnnnnnnnn | 14880 |
| nnnnnnnnnn | nnnnnnnnnn | nnnnnnnnnn | nnnnnnnnnn | nnnnnnnnnn | nnnnnnnnnn | 14940 |
| nnnnnnnnnn | nnnnnnnnnn | nnnnnnnnnn | nnnnnnnnnn | nnnnnnnnnn | nnnnnnnnnn | 15000 |
| nnnnnnnnnn | nnnnnnnnnn | nnnnnnnnnn | nnnnnnnnnn | nnnnnnnnnn | nnnnnnnnnn | 15060 |
| nnnnnnnnnn | nnnnnnnnnn | nnnnnnnnnn | nnnnnnnnnn | nnnnnnnnnn | nnnnnnnnnn | 15120 |
| nnnnnnnnnn | nnnnnnnnnn | nnnnnnnnnn | nnnnnnnnnn | nnnnnnnnnn | nnnnnnnnnn | 15180 |
| nnnnnnnnnn | nnnnnnnnnn | nnnnnnnnnn | nnnnnnnnnn | nnnnnnnnnn | nnnnnnnnnn | 15240 |
| nnnnnnnnnn | nnnnnnnnnn | nnnnnnnnnn | nnnnnnnnnn | nnnnnnnnnn | nnnnnnnnnn | 15300 |
| nnnnnnnnnn | nnnnnnnnnn | nnnnnnnnnn | nnnnnnnnnn | nnnnnnnnnn | nnnnnnnnnn | 15360 |
| nnnnnnnnnn | nnnnnnnnnn | nnnnnnnnnn | nnnnnnnnnn | nnnnnnnnnn | nnnnnnnnnn | 15420 |
| nnnnnnnnnn | nnnnnnnnnn | nnnnnnnnnn | nnnnnnnnnn | nnnnnnnnnn | nnnnnnnnnn | 15480 |
| nnnnnnnnnn | nnnnnnnnnn | nnnnnnnnnn | nnnnnnnnnn | nnnnnnnnnn | nnnnnnnnnn | 15540 |
| nnnnnnnnnn | nnnnnnnnnn | nnnnnnnnnn | nnnnnnnnnn | nnnnnnnnnn | nnnnnnnnnn | 15600 |
| nnnnnnnnnn | nnnnnnnnnn | nnnnnnnnnn | nnnnnnnnnn | nnnnnnnnnn | nnnnnnnnnn | 15660 |
| nnnnnnnnnn | nnnnnnnnnn | nnnnnnnnnn | nnnnnnnnnn | nnnnnnnnnn | nnnnnnnnnn | 15720 |
| nnnnnnnnnn | nnnnnnnnnn | nnnnnnnnnn | nnnnnnnnnn | nnnnnnnnnn | nnnnnnnnnn | 15780 |
| nnnnnnnnnn | nnnnnnnnnn | nnnnnnnnnn | nnnnnnnnnn | nnnnnnnnnn | nnnnnnnnnn | 15840 |
| nnnnnnnnnn | nnnnnnnnnn | nnnnnnnnnn | nnnnnnnnnn | nnnnnnnnnn | nnnnnnnnnn | 15900 |
| nnnnnnnnnn | nnnnnnnnnn | nnnnnnnnnn | nnnnnnnnnn | nnnnnnnnnn | nnnnnnnnnn | 15960 |
| nnnnnnnnnn | nnnnnnnnnn | nnnnnnnnnn | nnnnnnnnnn | nnnnnnnnnn | nnnnnnnnnn | 16020 |
| nnnnnnnnnn | nnnnnnnnnn | nnnnnnnnnn | nnnnnnnnnn | nnnnnnnnnn | nnnnnnnnnn | 16080 |
| nnnnnnnnnn | nnnnnnnnnn | nnnnnnnnnn | nnnnnnnnnn | nnnnnnnnnn | nnnnnnnnnn | 16140 |
| nnnnnnnnnn | nnnnnnnnnn | nnnnnnnnnn | nnnnnnnnnn | nnnnnnnnnn | nnnnnnnnnn | 16200 |
| nnnnnnnnnn | nnnnnnnnnn | nnnnnnnnnn | nnnnnnnnnn | nnnnnnnnnn | nnnnnnnnnn | 16260 |
| nnnnnnnnnn | nnnnnnnnnn | nnnnnnnnnn | nnnnnnnnnn | nnnnnnnnnn | nnnnnnnnnn | 16320 |
| nnnnnnnnnn | nnnnnnnnnn | nnnnnnnnnn | nnnnnnnnnn | nnnnnnnnnn | nnnnnnnnnn | 16380 |
| nnnnnnnnnn | nnnnnnnnnn | nnnnnnnnnn | nnnnnnnnnn | nnnnnnnnnn | nnnnnnnnnn | 16440 |
| nnnnnnnnnn | nnnnnnnnnn | nnnnnnnnnn | nnnnnnnnnn | nnnnnnnnnn | nnnnnnnnnn | 16500 |
| nnnnnnnnnn | nnnnnnnnnn | nnnnnnnnnn | nnnnnnnnnn | nnnnnnnnnn | nnnnnnnnnn | 16560 |
| nnnnnnnnnn | nnnnnnnnnn | nnnnnnnnnn | nnnnnnnnnn | nnnnnnnnnn | nnnnnnnnnn | 16620 |
| nnnnnnnnnn | nnnnnnnnnn | nnnnnnnnnn | nnnnnnnnnn | nnnnnnnnnn | nnnnnnnnnn | 16680 |
| nnnnnnnnnn | nnnnnnnnnn | nnnnnnnnnn | nnnnnnnnnn | nnnnnnnnnn | nnnnnnnnnn | 16740 |
| nnnnnnnnnn | nnnnnnnnnn | nnnnnnnnnn | nnnnnnnnnn | nnnnnnnnnn | nnnnnnnnnn | 16800 |
| nnnnnnnnnn | nnnnnnnnnn | nnnnnnnnnn | nnnnnnnnnn | nnnnnnnnnn | nnnnnnnnnn | 16860 |

```
nnnnnnnnnn nnnnnnnnnn nnnnnnnnnn nnnnnnnnnn nnnnnnnnnn nnnnnnnnnn    16920
nnnnnnnnnn nnnnnnnnnn nnnnnnnnnn nnnnnnnnnn nnnnnnnnnn nnnnnnnnnn    16980
nnnnnnnnnn nnnnnnnnnn nnnnnnnnnn nnnnnnnnnn nnnnnnnnnn nnnnnnnnnn    17040
nnnnnnnnnn nnnnnnnnnn nnnnnnnnnn nnnnnnnnnn nnnnnnnnnn nnnnnnnnnn    17100
nnnnnnnnnn nnnnnnnnnn nnnnnnnnnn nnnnnnnnnn nnnnnnnnnn nnnnnnnnnn    17160
nnnnnnnnnn nnnnnnnnnn nnnnnnnnnn nnnnnnnnnn nnnnnnnnnn nnnnnnnnnn    17220
nnnnnnnnnn nnnnnnnnnn nnnnnnnnnn nnnnnnnnnn nnnnnnnnnn nnnnnnnnnn    17280
nnnnnnnnnn nnnnnnnnnn nnnnnnnnnn nnnnnnnnnn nnnnnnnnnn nnnnnnnnnn    17340
nnnnnnnnnn nnnnnnnnnn nnnnnnnnnn nnnnnnnnnn nnnnnnnnnn nnnnnnnnnn    17400
nnnnnnnnnn nnnnnnnnnn nnnnnnnnnn nnnnnnnnnn nnnnnnnnnn nnnnnnnnnn    17460
nnnnnnnnnn nnnnnnnnnn nnnnnnnnnn nnnnnnnnnn nnnnnnnnnn nnnnnnnnnn    17520
nnnnnnnnnn nnnnnnnnnn nnnnnnnnnn nnnnnnnggt ggagagttct gtagatgtct    17580
gttaggtctg cttggtccag agctgagttc aagtcctgga tatccttgtt aaccttttgt    17640
cttgttgatc tatctaatat tgacagtggg atgttagact cgcacacaat aataatgaga    17700
gactttaagt cttttctag gtctctaagg acttgcttta tgaatctggg tgctcctgta     17760
ttgggtacat atatgtttaa gatagttagc tcttcttgtt gaattgatcc ctttaccatt    17820
atgtagtggc cttcttttgtc tcttttgatc ttagttggtt taaagtctgt tttattagag   17880
actaggattg cattccctgc tttttttttt cgcttggtag atcttcctcc agctgtttat    17940
tttgagccta tgtgcatctc tgcacgtgag acgggtctcc tgaatacagc acagtgacgg    18000
gccttgactg tttatccaat ttgccagtct gcgtcttta actggggcat ttagcccact     18060
tatatttaag gttaatattg ttatgtttga atttgatctg tcattatgat gtttgctggt    18120
tattttgccc attaattgat gcagtttctt cctagcctcg atggtcttta caatttggca    18180 tgttttttgca gtggctggta ccagttgttc cttttccattt ttactgcttc cttcaggagc  18240
tcttttaggg caggcctggt ggtgacaaaa tctctgagca tttgcttgtc tgtgaaggat    18300
tttatttctc cttcacttgt gaaacttagt ttggctggtt atgagattct gggttgaaaa    18360
ttctttaaga atgctgaata ttggccccca ctctcttctg gcttgtaggg tttctgctga    18420
gagatctgct gttagtctga tgggcttccc tttgtgggta acccgacctt tctctctggc    18480
agcccttaac attttttcct tcatttcaac gttggtgaat ctgacaatta cgtatcttgg    18540
gattgcgctt ctcgaggaat gtctttgtgg tgttctctgt atttcctgaa tttgaatgtt    18600
gacctgcctt gctaggttgg ggaagttctc ctggataata tactgaagag tgttttgtaa    18660
cttggttcca ttctgtctat cactttcagg tacaacaatc atagcattgg tcttttcaca    18720
tagtcgcata tttattgaag cctttgttca tttcttttca ttcttttttc tctaatcttg    18780
tcttcttgct ttatttcatt aatttgatct tcgatcactg atatcctttc ttctgcttga   18840
tcgaatcggc tattgaagct tgtttatgct ttgtgaaatt cttgtacttt ggttttcagc    18900
tccatcaggt catttaagct cttctctaca ctggttattc tagttagcca tttgtccaac    18960
cttttctcaa ggttttaagt ttccttgcga tgggtcagaa cgtgctgctt tagcttggag    19020
aagtttgtta ttaccaacct tctgaagcct acttctgtca actcgttaaa ctcattgtcc    19080
atccagtttt gttcctttgc tggtgaggag ttacgttcct ttggaggaga agaggcgttc    19140 tgttttttgga attttcagcc tttctgctgt ggtttctccc catctttgtg gtttatcta     19200
```

```
cctttggtct tgattttgg tgacgtacag atgggttttg gtgtgggtgt ccttttgtt      19260
gatattgatc ctattccttt gtttgttagt tttccttcta acagaggccc gtcagctgca   19320
ggtctgttgg agttgctgga ggtccactct agaccctgtt tacctgggta tcaccagtgg   19380
aggctgcaga acagcaaata tcgcggcctg atccttcctc tggaagcttc gtccaagaag   19440
gacacccacc tatatgaggt gtctgtcggc ccctactggg aggtgtctcc tcccagtcag   19500
gctacatggg gctcagggac ccacttgagg aggcagtctg tccgttactg gagttcaaat   19560
gccgagctgg gagaaccact gctctcttca gagctgtcag gcaggatgt ttaaatctgc    19620
agaagccgtc tgctgccttt tgtttagata tgccctgccc ccagagatgc aatctagaga   19680
ggcagtaggc cttgcggtgg gctccaccca gttcaagctt ccttgctgct ttgtttacac   19740
tgtgagcata gaagtgcgta ctgaagcctc agcaatggcg gggaggcgct tcccctcacc   19800
aagctccagc atcccagctt gatctcagac tgcttggcta gcagcaagca aggttccatg   19860
ggcatgggac ccccgagcc aggcactgga ggcaatcacc tgctctgcca gttgcgaaga    19920
ctgggaaaag cacagtattt gggcagagta tactgttcct ccaggtacag tcactcacgc   19980
cttccttgg ctaggaaagg gaaatcccct gacccttgc acttcctgga tgaggtgacg     20040
tcctgccctg ctttggctca ccctccatgg gctgcaccca ctgtccaacc agtgccaatg   20100
agatgaacca ggtacctcag ttggaaatgc agaaatcacc atcttctgc atcgatcttg    20160
ctggagctg tagaccagag ctgttcctac tggggcatct tggaagcaac tctgggtctg    20220
agtttctgtt tgttgccctg atgtatatcc ccagtgccta gaatgatact tgttacatag   20280
gaagtgcttg atccatgttt gcacaaatga atctttctca taatgaggtt tctctaaaca   20340
agctgttctc ccaaaaactt acacccagct ttatgttgaa gcatctcatt atacattgga   20400
aagatgaaat gtgtagtgag actttgaatc ttcttttgaa tctagaaaca ttagcatttt   20460
tagaccattc tattttaata tttatgaaat ttatgaaata ataagaaaca tgaggccggg   20520
ctcagtggct tatgcctgta atcccagcag tttgggaggc cagggctagt ggatcatgag   20580
gtcaggaatt tgagaccagc ttggccaaca tggtgaaacc ccacttctac taaaaatata   20640
aaaattagct gggcgtggtg gtgcatgcct gtaatgccag ctcctggaga ggctgaggca   20700
ggagaatcat ttgaacctgg gaggcggagt ttgcagtgag ctgagatcgt gccattgcac   20760
tccagcctgg gcaacattgc gagactccat ctcaaaaaca aaacaaaaa caaaaaaat    20820
gtgtgaccta aattaggctt atagatgaac cattgcagtc atgattaatt ccgccattgt   20880
ttgccttgtg atctttggtg ccatgtctgt acatatttca tgatttctgt gttttttacgg  20940
tttccatttc agatctccct tgagtttaga atctggctg agaaataccaa acagtgatt    21000
gccgacattt gccggagaat gggcattggg atggcagagt ttttggataa gcatgtgacc   21060
tctgaacagt agtgggacaa ggttagtctc ataaaacagt gtctgtgtgt gatgtattag   21120
acagagctgg cagtcctcat agtgaagctc agaacaagaa aagttgtcca gtattttcag   21180
cccctctggt tttacaattc atctgtttag gttgaatgtc tcatcataaa cagtttattc   21240
cagagttaat tccaaaccag cagctatgta ggatatcagc caggctagga gtagggtact   21300
ggagagaagt gcttatctag acaaagggat gtaattgacc atgaagatta aaactacaca   21360
tcaaaacata aggtagggtt aggagtcttg cctatttttc ataggaatgg tgtttgtgag   21420
acttactcat cacttctgtg gaagtaaaga catttatttt attatttta aagccagtca    21480
gatttagcag gcagagacat ttcagacatc taaagtgttg atgtatttca tacctttaac   21540
tgtgcttaaa ttaggatctc cgaaaagatg ctgctacatg gtcactacgt tagtgtaggt   21600
```

-continued

```
ccaaggtctt gggcctctta attttcaaa cctcaaaact tgacagcagt tatctttgga   21660
actgctgatt tgtgcttcct aagttaacag catacaatga ctgctagaaa tcaatttctg   21720
catttaaggt gaagttagcc gggtactatg gtttacctgt aatctcagca ctttgggagg   21780
ctgaggtggg aggatcattt gagcccagga gttagacaca agcctaagca acatagcgag   21840
accccgtctt tcaaaaaatt aaaaaatgag cagggaattg gtggcatgtg cctgtggtcc   21900
ccagctactc tggaggctga ggtgtgggag gattgcttga gcccaagagt tgaaggttgc   21960
agtgagccat gattgtgcca ctgcactcca acgtgggtga cagagcaaga cacctactga   22020
aagaaaataa agttgaagtt aaaacttctg gccaagaacc agcactggtt atgatagtaa   22080
ctcattttct gttgtgcaga tttattcagg aaacttaatt ttaggttgtt gaatagaagt   22140
tttgatcaga taaaattgaa ttaaaaaaaa tttttttga dacagggtct tgctgttatc   22200
caggctggtg tgtagtggtg tgatcacggc tccccgcagc ctcaacctcc tgggctcagg   22260
tgatcctccc acctcagcct accgagtagc tgtaactaca gtgcatgaca ccataccagg   22320
ctcatttttg tacattttt gtagagagag ggttttgcca tgttcccag gctagtctca   22380 aactcctggc atcaaacagt cctcccactc tggcctctca aatgttggga ttacaggcat   22440
gaccagccaa ttatttcaag gagttatttt ttttcttcta ctttggggga agatgaatta   22500
tataagtctc cattttagga gtatttctac caaaagaact attatcttca aatatatttt   22560
tggatagtac tatagatata ctaattttt tttaaatttc tagtaattct tttgaagatt   22620
ttgtatagct gtccaaagcc aatttctgtc tacctaattt cagcaagatt tcactctttt   22680
catgttactt ttgtcccaga acaaatttca agtgctttct cttcacctgt gcattcttcc   22740
ccctgattag tctctggctt tgtattactt tcagtcagag acgactttt tttttgaga   22800 cagggtctca ctctgtcacc cagactggaa tgcagtggca cagacaaggc agccttgacc   22860
ttctgggctc aagcaatctt ccttgccctc agcctcctga gtaactggga ccacaggcac   22920
gttgccacca tgcctggcta atttattta attttatta tttttgagac agggtattgc   22980
tctgtcaccc aggctggagt gtagtggcat gatcaaggct cactgcagcc ttcacctcct   23040
gtgctcaagc agtcctctca cctcagcctc cccattagct gggactatag gtccacacca   23100
ctacaccagg ctaattttg taattttgg tagagacag ggtttcatcg tgttgcctag   23160
gctggtcttg agctcctggg ctcaagcgat tcacctgcct tagcctccca ggtgtgagcc   23220
actacactca gccttttaaa atttttaca gagatgaggt cttgctttgt tggccaggct   23280
ggtctaaaac tctttgggctc aagcagtccc ctctccacag cctcccaaaa ttccgggatt   23340
acaggcgtga acttcggtca tttcctaact ttaacccttc ctaatgacac tccagagctt   23400
accttcttta cttttgcttc ttaagttaac taatagacaa ttattgtatg tggatattgc   23460
attaagttgt cttaggatac ccttttcaga ggaggacagc ttttgacaaa ttgctgtcgc   23520
ggaaaaaaaa agtatttggc aattaagagt tgcatttact gaaatctctg ttgagagagg   23580
ggaagttacg ttgtctctaa aagaaaaact aaaaagaaaa ggggaagttt tagcaaagtt   23640
gttaaagcct gacacttaag tcatactacc tagttttgaa ctcttagccc ctgccacaga   23700
cacggcagcc ccttgaacct tcctgggttc aagcgagcct cctacttcag cccccctgagt   23760 aactgggacc actggcctgt gtcactgtgc ctggctaatt tttttttttt cctcacatgg   23820
gcaatgttgg gcaagttaaa tcgacttctt tgtgcctcag tttcctcatc tgaaatggag   23880
atcatactgc tatgtacctg atacaatgtt tgtgaggatt gaatgtgcag agttcttttt   23940
```

-continued

```
ttctgttgtt gttgttttga gacggagtct cactctgnnn nnnnnnnnnn nnnnnnnnnn    24000
nnnnnnnnnn nnnnnnnnnn nnnnnnnnnn nnnnnnnnnn nnnnnnnnnn nnnnnnnnnn    24060
nnnnnnnnnn nnnnnnnnnn nnnnnnnna tctcgtgatc cgcccgtctc agcttcccaa     24120
agtgctggga ttacaggcat gagccatcgt gcccggctga atgtgcagag ttcttaaaac    24180
cgtgtcaaga acataaaata gttatttgtt ctttcatata atgatgattt tgagggcctg    24240
cggatcttga catgttatca gattggtcaa aaaagatta aaccatagtt ggtattgtcc     24300
tagttcctgt taccagaata ttccatcttt catcgttgcc ttctctcata gttttatgta    24360
tcaaaaagtt tattgtaaag ctaggccggg cacggtgtct gggctggta atcccagcac     24420 tttgggaggc caaggctggc agatcagttg aggtcaggag ttcgagacca gcgtggccaa    24480
catggtgaaa ccccgtctct actaaaaata aaaaattagc tggatgtggt ggtgggtgct    24540
ttaattccag ctactcagga agctgaggca ggagaatcac ttgaacccaa gaggcagagg    24600
ttgcagtgag ttgagattgt gccactgcac tccagcccag gggacaaagt gagacttgat    24660
ctcaaaaaaa aaaaaaaaaa aaagttattg taaagctaga cacggtggta tttgcctaca    24720
atcccagctg ttcgggaagc tgaggcagaa agattgcttg ggtccagtag tttgagtcta    24780
acgtgggcaa atatatgaga ctccatctca aaaaaaaaaa taaaaaataa aaataaaaaa    24840
atgtttacta gttttttttca gtagccttt attatagtag cagtacatgt gtattgtaga    24900
aatttgaaaa atacaagtga aaaataaaaa catcaaattc ccgtcagcca gagactgctg    24960
tgaaatgttt tgagcacatc cttcttgaat gttttttaaa tcctggtatg tatatttgta    25020
ttttaaaatc aaaatgcatt cttacccatt ctcttttgaa cctgctttt tgtagctaat     25080 gatctctagt gtgtccattt cagtaaaaat tccattatta aagtgcttta aaaatcgtct    25140
cttacagtac tgccactatg ttgctgggct ggtcggaatt ggcctttccc gtcttttctc    25200 agcctcgag tttgaagacc ccttagttgg tgaagataca gaacgtgcca actctatggg    25260
cctgtttctg cagaaaacaa acatcatccg tgactatctg gaagaccagc aaggaggaag    25320
agagttctgg cctcaagagg taacagattc agggtatttt gggggaaaat aactttagac    25380
attctctgaa aaatccttta actcttgtgg ttgcgggtga cagaaaaaca gccaggcct     25440 cccccaggca gcataagggg atgtggaaaa taggatagat tgacatgagt ttgcttcagg    25500
tagactggct gactcccagg attcacacca cgtaatcagt atattcaagc cttgctgtcc    25560
ttgatttctt tcagacggtc tttctccaag tggtggatat ggtaacaacc cacgtgcact    25620
agcttaacaa aaagttctta ggaatggctt tgttcggcct ggcgcagtgg ctcatgcctg    25680
taatcccaac agtttgagag gccaaggtgg gcggatcacc tgaggccagg agttcgagac    25740
cagcctggcc aacatagtga aacccccgtgt ttactaaaaa atacaaaaat tagccgggcg    25800
tggtggcaag gcttgtaat cccagctacc tgggaggctg aggcaggaga atcgcttgaa     25860
cccaggaagc agagattgcg gtgagctcag attgtgccac tgcactccag cctgggcgac    25920
agagtgagac tccctctcaa aagaaggaga agggcttggt tcttctgctc agccctgaat    25980
cagttactgt tgctacacag ctgagttctc tggcctcacc tggattacgt ctacacagta    26040
cacacagaat ggatttcccc caaagaaaga attctgcggc aggaagggga aagggatggc    26100
aggtagacaa aaactccagg tgtctgtaat aagggacagg gtcgatcttt aattaaaaca    26160
tggacaggga acagaaagct tttgatactg attttgttca gaaggaaagt agaaaatttt    26220
atgactgttc cctgaattta ttccagcatt taccttttgc tttccataaa agtgtttcct    26280
gcagccaagt actttaaagt tttaaaaaga cgggtgaggc taagtgtggt gtctcatact    26340
```

-continued

```
tataatccca gtgctgaggc caggagttca agaccagcct gagcaacaca gcaagatacc   26400
atctctataa aaaattgtta gaaaatgatt ctgctgaaag agcaaaaata aaaattaaag   26460
aaagtagaaa aaataaaact aaatttaaaa gattaactgg gcatgttggc atgcacctgt   26520
attcctaggt attcgggagg ctaaggcaca aggatcccct gagcgcagga gctcaaggtt   26580
ggattgagtt gtaatcacac cactgcactc cagcctcggt ggcacaatga aactgtctca   26640
agaaaaaaaa aaagtgacag agggaaacaa tatttgcaat tcatagagca gatacagggt   26700
tcatattcct aatattaaaa aaaacttcta aaagttaaga aaaaggccaa ctgccccaca   26760
gaaaaatggg caaggagata agaacaagat tgttcacagg aagagacaca cagatgatta   26820
ttaaaaatct gaaaagatgc tgagtcttac tcctaagaaa aattcacatt taaactactc   26880
tgggggctgg gcaaggtggc tcacgcctgt aatctcaaca ctgggagacc aaggcaggaa   26940
gatcactgaa gccagggtat cgagaccagc ctggacaacg tagtgagacc ttatctctta   27000
aaacaaaaca aaacaaaaca aaacaaaaaa aacagtaaaa attggccggg cacagtgact   27060
cctgcctata atcccagcac tttgggaagc ccaggtgagt ggatcacttg aggtcaggtg   27120
tttgagaaca gcctggccaa catggcaaaa ttccgtctct actaaaatta caaaaattag   27180
ccaagtgtgg tggcatacgc tgtagggcc agctacttgg gaggctgatg tgagactcca   27240
tttaaaaaaa aaaatcaaa aattagctgg gtatagtggc acacccctat agttctcgct   27300
ccttgggagg ttgaggcagg aggattgcct gagcccagga gttcaaggct gcagtgaacc   27360
atgatcacac cactgcattc tagcagcctg ggagacagag caaaaccctt gtctcaaaac   27420
aaacaaacaa caacaaaaac aaaaaacact tccctcagct cagacatggc cttttaagtt   27480
tcctaggtga ctcgtgtgca gccagggttg agaaaccact cttgtcttac ccctcttttg   27540
cagacacagg gctcagagaa gggaagggga ttgtctgggg atgtatagtg aggcagtggc   27600
tgccttggaa gtggagtctc agtctcccgg ctcctaggcc agcccctgac cactgttcca   27660
ttgtctccca gacagaacat cagccacggg catgtgatgc atgagcgtga gccacaccat   27720
cttgcacaca caggagcaga gccctgctct tctcattcac ttactttatc tgtaaaatag   27780
catcatttct accacacggt ggtggtgtga ataaaatgag atgaacttct agcatagagt   27840
gcttagtaaa ggttctggac atttcgtagt agttgaatca tgccaaatgt ggtcctaggt   27900
gattggcttc ttttgctagc atgttttcag ggctcctcca tgctggggca ttgcatcact   27960
gctttattcc tttttatcgc ctagtattat tccactgtgt ggatagacca catttatcca   28020
ttcatcagtt ggaggatatt tgggttcttc ccatttttt tggctatggt gaatagtact   28080
gtgtacattt gcatataagg ttttgtgtag atgtgtgttt tccttttct tgggtctatg   28140 ctgagaagtg gaattgctgg ttcatacagc agctcgaacc ttgtgaggag ctgccagacg   28200
cttttccaag gtcgctccac cattttacat tcccgtcagc agtgtgagag tcccagtttc   28260
accagcactt gttgttatct cttttttaact gtatgtatat atacttaaca tttatttat   28320 aataaatgta cataatagag aatttgccat tttaactatt tttaagtcta ttattcagtg   28380
gcattaagta cattaatgat gttatataac catcaacact atgtttccag aactttcgct   28440 agcttccagag aatcctctaa ataatatcat taaaaatcat caagccgaat cccactgtta   28500
gaattaaagg tttatttca ctttcaagtt atcaggatcc agggaggtgt aatacactta   28560
gaggatagac tcagctcatt tcccagctat gcctttcagc agcattctta ccagagtagg   28620
aatataatgt tagtcattat ttagaggcct ggccatcttg agaaggttta ctgtttagtc   28680
```

```
tgcagtacaa ttataactgt ttttgtatat tgggttattt ttttcagaag taggccagta  28740
gctctaacag gagcctcttt agcctgaatt cgtccaagta gtgcagtgtt gcactagttg  28800
tccctcggga catgctcccc aatacgtaac tcacttccag gttgcaactg gacacttact  28860
ggtagtcaga aatagctatt gcatggagct taaaatgaac ttgatcttcg tgaaagatga  28920
gtctgcagct aagagacttt actgtatatc atagtgtttt tttttgtttt gttttgtttt  28980
tgttttgtg acggagtctc actctttcac ccaggctgga gtgcaatggc gagatcttga  29040
ctcactgcaa cctccgcccc ctaggttcaa gcaattcttc tgtctcaccc tcctgagtag  29100
ctgggattac aggcgcctgc caccgtaccc ggctagtttt tgtatttta gtagacacag  29160
ggtttcacca ccttggccag gctggtcttg aactcctgac ctcgtgatcc accctcctcg  29220
gcctcccaaa gtgctgggat tacaggcgtg agccacggcg cccagcctgt atcatagttc  29280
ttatgcacaa agacccttta atattgtttg taaattctcc cctatgcaca cgctgacctg  29340
ttccttaatc ttcttatctg tctaggtttg gagcaggtat gttaagaagt tagggatt   29400
tgctaagccg gagaatattg acttggccgt gcagtgcctg aatgaactta taaccaatgc  29460
actgcaccac atcccagatg tcatcaccta cctttcgaga ctcagaaacc agagtgtgtt  29520
taacttctgt gctattccac aggtagggaa cggggctcct ctgggtggat acggggctaa  29580
agggagtggg gtaggagtaa gggtggattt tgctgtgcta tattcaagga tatgattcct  29640
taaaagacg atgactccag tttattacgc tgggagtttc atagcacccg cctttgcttc  29700
cagccaccaa actcagctca gccttgaggt taagcctgct ccttttcaga accttctttc  29760
cggatttact attttctaca gctatcctaa actagttagg ttcttttcct cacagttaag  29820
tcaaggtctt tggcttagat ttatggggag tgctgggtaa aacctgggtg aagctgttat  29880
cattaaaaag tcttcattaa gcacctaatt actgctgtcc ttttcctaga cccggcataa  29940
aaagaaccctg gtccggtaga cctagcctct cagtatgcta ggaacttaca cttttttagtt  30000
gcctttacca agtattgcag atactactgc aaataagtga agaaagtaac agcatttaac  30060
tgatttggga acttggtttg atcttgttct aatgacccac ttcgaatggt ggttgaaagt  30120
aaaatctgta tcgccgtctt atgtttccat ttacctagaa atactttacc tttgagcaca  30180
ggaaattaat ccccttctgg ttgttctccc cctggcattg gttttaaata tataatgatt  30240
atgtttgttg taggaaaaat agaaaaacaa ctacaataga aaattcttcc catatattat  30300
tttgaaatac atatttccga tccgataatc cattgctcta gcatggaaaa tgttggattt  30360
acttgtgttt gcttttttcca aataaaatgg aacttttgtg gctacattat agaattgttt  30420
tagactgctt aattctgtgt gttgttgaga aaggaggag tggggaaggt aaaaatcttg  30480
acatactttc ttcgtgggta ttttttcttg agcgattcca tcttagttga ttagcagtta  30540
gcaattgccc attcaacaga aggttttctt acctttttgt gataatgata gctaacgaca  30600
tcatttcttc tttttttccct ctcttcttgt tgtctctagg tgatggccat tgccactttg  30660
gctgcctgtt ataataacca gcaggtgttc aaagggggcag tgaagattcg gaaagggcaa  30720
gcagtgaccc tgatgatgga tgccaccaat atgccagctg tcaaagccat catatatcag  30780
tatatggaag aggtgggttt ttatttaact acttggataa tttgtagcta cttttatgat  30840
ttagtaatgt cactgtttaa ccaggtttgg atattagatg atcctaacaa ttcactatcc  30900
tgtggcctaa agacagga attgatatcc tttataagga aaaagtcta ttcacaggag  30960
ccgagcagat tgctcactgc tgtgtagtac cctggtgaga ggagataaat ggagcaaggc  31020
tgtaggttgg agcccctcag tagaatcata gattttgagc tgcaagatga tgcaggaggc  31080
```

-continued

```
caaccaagct tcttgttgct ggtgaggaat gtgaggttga agcttgtctg tgctgatgca    31140
gtgcgtgatt gagtggatct ctggctcccg tccatgtgtc ctgacaccca gtctggtact    31200
ttcattatgc cacaggcctc aattgaaaaa tcacagtagg gaatttaggc caaggaaagc    31260
catcaagttg caattatttc ctaaattttc tttggaaaat ttcatttcaa ataccaaaac    31320
catcctataa aagaaaaact taccttctta ggtcaaatct ctaatatttg actaggttca    31380
aaaagtttat ttctggccag gcacagtagc ttactcctga aatcccagca ctttgggaga    31440
ccaaggtggg aggatcactt gaggccagga attcaagacc agcccgggcg acatagcaag    31500
accccatttc tacaaaaaat ttaaaaattg tcatggtggt gcacgcctgt ggtcccagct    31560
actcaggagg ctgaggcagg tggatcacat gagcctgaga ggtcgaggct acagtaagct    31620
gtgtgatttc atcattgcac tctagcctgg gtgatagagt gagactttgt ctcaaaaaaa    31680
aaaaaaaaaa aaaagtctt agagaccaga agtctctgta atctctaata atctctaggc    31740
cctagagcag tggtttgtaa atggaggtga tttgctcccc tcccccagga ggacattgga    31800
caatgtctgg agacattttt gattgtccta accggcagga atcgggtgct actggcatct    31860
ggtgagtaga ggcccaggat gatgctgtga tcctcaggtg tgatcctgtt gagaatgaaa    31920
cactgtagac tttatgaaaa catacaagac cctcatcatt tttcctttgc ctgagctccc    31980
tccccagagg ttacctctgt tcatggtttt gtgcatccgt ctagtccccc tgttacgcgt    32040
ttacaggaat atggtttgca acagtgtttt catctaaata gaattataca aaatagcgat    32100
ttctgatttc tcttgcatat tgcacattct tcttatactt cctccctacc tttatctgac    32160
acagaaatgc tgtatgtcca gaacttctat cagaggcacc tatggaagtc taagggaaga    32220
ccacatcgct tttaaaaacc ctaaaatttt gtagtcacta gatgaaaata ttcagccagt    32280
gacccaaaaa attgctacca atgagactct ccattttgcc atgtagccag aacttacttt    32340
gatctatgtg cctggggtag tgaccaagta ggtgggtagg agtaatctca gggaaacttg    32400
aggccccagc ctcatggcta gggtcataat ttgaacccag gtctgtctga catcagaatc    32460
catgatgtta accccaattc taaggggttc aactaccctt tctaaatgga atcctgctat    32520
attaagcact atttattcat tttatataaa ctagaaacat tttatgtagt aagtagttga    32580
gagtgttttg gttttgcagt ttgatcacta gttttagaaa ccagttttta aacactttgt    32640
ggccaattcc attactatat taaaattcag atttatttgg tttttccttta actattggga    32700 ttaaatcctg gttgtaattc atagtttgag ggcgagggtg ggcagtctac atttggctga    32760
gccctgtttt tgtgaataaa tgttatcaga acacagccac acccatttgc ttctatgtct    32820
tctgtggctg cttttgcaat gtgacggccg agttgaggag ctgcaacagg cgatgacttg    32880
taaagctgaa aatattttt ggcccttgaa taagaggttg gctgacttct gacttagggc    32940
atcagttgtt ctgttatccc agtaaaactc aaggcattag gggagaaatg ttaatattaa    33000
tacttaagtt gatttgattt agggaaatct ttgaagattt ctaagtctta agcagtagaa    33060
cctgttaatg gttttagttt cagcagtaag gacattttac aagtaaagtt ttaaatgaaa    33120
acattttgta tgaagccaca agtcgtctgg cctcttgctg tgtccagat attaacactg    33180 atcctatttc tccttgctga ccaagtctgt cctttgtagt aagaaaggaa gaaacgttga    33240
ctctgtccga tctctggact tagtgttgta gcgagcatgc acctggaagg gacttgccag    33300
aggacctcct catgcttctc cagtgcttag tgggggcttg gagtgcagcc ccaggtcttc    33360
acgagcagtt ggccacactg cagggccctc accccactct ggagcagcct ctgcttcaaa    33420
```

```
ccagcctgga tgcttgtcag ctggggagaa gatcaacctg ctattttggg atagaaataa   33480
atgctcagcc aaacggccag aaaccccat  tcccctctct gccaaagtga attccttggc   33540
agggagaagc ttgttcgtgt ctctgcacac ttcctgtgcc ctcctgtggt taagtcagag   33600
aatcatccgg ctctttgagc cccaggtgcc tagctgctca aggatggtcc ccagccagca   33660
gctgccagga atcacctggg agcccattaa gacatccagc ccccacccaa acctatcgaa   33720
tcagaatctg cctttttttc ccaaatgatg ttttgctttt aatggaagtt tagatgttca   33780
tagacaaagt ttttaaatga tgatcaagct gattccatat tcgcagttgt aagtagaact   33840
gctgagacgt ggaagtacca catggactca cagaggagct gctgtatgta gcacagcatt   33900
gcacaagagc ttatttcagt ctagtaaaca tttataggag cctgtgtcat ttaatcatca   33960
agcctcgcac tgtggctcac acctgtaatc ccaaactttg ggaggctgag gcaggcaga   34020 tcacttgagg taaggagttc gagaccagcc tggccaatat ggcaaaaccc tgtctctact   34080
aaaaatacaa catttagcca ggtgtggtgg tgcacacttg tcatcccagc tattccggag   34140
cctgagacat gagcatcgct tgaactcggg aggtggaggt tgtagtgagc tgagatggca   34200
ccactgcact ccagcctggg caacaggtg aaggcccttt ctcaaactcc tcaagtattt   34260
ggcttcaact ttatgccggg catgtagatg aaaagtcggc tatgacctgt ccttgacaag   34320
cagatgtaac tccttgattg aggctagtag gttttttaaga cctgaataat tgagtttgca   34380
gaaacctact gtgtgccttc aggtaaatgg agagtggggt ttggtctagc aacgaagcat   34440
ctagaaggtc tctttggcct taccggctct gttttaggta agtccacgtc tgagtaccag   34500
tgactgcagc tcttccagtt gtgctgtcat gtttatatgt tagaaatgat catcaaagga   34560
ctcaaaagtt ttgccactaa ttgtattacc ggggactgtc acaaccaaga tttctcttaa   34620
tttattcacc ttacttatct cctggaaggg catattgaag tgctcttgga gttctctaaa   34680
agggtttttg ttggttgtgt atattcactt gggtgccagc gattgattcc aaataagtaa   34740 atctttttc  ccaaaaggat gtaagatggc ttatggttat aagtacaaca ggctaacaaa   34800
gtacaagtag atgagaaagt aaaatgaaga aataaagtca taggagccac agaattaacc   34860
caggaatgaa taagtgtgta gtttggtgct gatgttatca tcctttattt gtacattgct   34920
tgtacagttg ctctgagaag gtaagtctta aattttcaaa agtgaaatgt caccgagcat   34980
ggtggctgat gcctctaatc tcagcacttt gggaggctga ggcaggcgga tcacttgagg   35040
tcaggagttc gaaccagcc tgacttatgt gatgaaaccc tgtctctact aaaaaaaaa   35100 aaaaaaaaa aaaaaaaaa aaaatccaa  aagttagttg ggcatggtgg caggtgcctg   35160
taatcccagc tacttgggag gctgaggcag gagaatcgca tgaacctggg aagtggaggc   35220
tgcagtgagc caagattgca ccactgcact ctagcctggg tgacagagcg agacaccatc   35280 ttaaaaaaa  aaaaaatct acaatatacc aaaaccatta cttacctgag aaactattct   35340
cagggtcatt gtagtgaatg cctatttttat ggcttttgat ggcatcaggg cactcaggtc   35400
atttacaaga gtagtgtgtg agaccctgtg tgtcactgcc actcatcttg gccttcggcc   35460
actgctgtag caaccagttt ccaagtaggg ctggaccttg ccttctgctc cagagacctc   35520
tcgcttcctg cccttgggct tctgacgagc tgcaggaact gcctggcacg tgggtcccca   35580
caacccagag gaggtgaggg ccacctctct gctcctcagg gccacctttc ataaggctcc   35640
ttgaaggtcc ctcaagatca agccaactca acacatcctt gataggcctt cctgccttct   35700 gttcacttc  tccactcgtt tccaaataaa tggctgcatg caagcttttg cctcaggttc   35760
tgcttttagg aggaaggcta agacaagcag taaagcaaca tgggcaggca gaaggatgac   35820
```

```
ttctaataga attatctcat cactatatat tttactttat ggatgcttgt attgaaaagt    35880
cttggctggg tggagtggct cacgcctgta atcccagccc tttgggaggc cgaggtgggt    35940
ggatcacttg aggtctggag tttgagacca gcctgaccaa cactggtaaa accttgtctc    36000
tattaaaaat gcaaaaatta gccagggatg cacgcttgct gtgtgccagc acagggctag    36060
gctggagata aaaggtgagt aagtaggtgt cggtgtagtc agggtgaaaa ctacagatgg    36120
tccatttcca cgtaagtgga aaggtaaagg tatgtacaat agggtggctc ctggctgaac    36180
ctggagctgc agacaggttt tctagaaggc ataatcctga agttgagact tggggggccta   36240 ggtaggagcc agttgaaggg acgtgggagg cgcattccag agagaaggag tggtatgaga    36300
ctggaacaga ggtgtgcagc agcatcgcat gggcgaaaca acagtagaca gttgttcttt    36360 tgttttttgtt tgtttttttga dacagggtct tgttctgtca tccaggctgg agtgcagtgg   36420
catgatctcg gatcactgca acctccacct cccaggctca agtgatcttc ccaccccagt    36480
ccccaagtag ctgggggacc acaggtgcat gccacgatgc ccggctaatt tttgtacatt    36540
ttgtagaaac agggttttac tgtgttgtcc aggctggtct taaacgcctg agcttaagca    36600
gtctacatgc ctcagcctcc tgaagtgctg ggattccaaa catgagccac tgtgcctggc    36660
ccggcaactg ttactagact atagagaggg aggtgggcaa gggctggtga cactagacag    36720
gtgcagtagg tctggaccat gggtggcctt gcgctacaca ttacagagct caggcttttt    36780
ttctccaggt gagagggctg gtgccactga ggcatcaagc agaggtttga gatctccttg    36840
gtgacagtgt agagcagaca ggtagatttg ggaatttaag cttagactca cgttggagac    36900
tgagatagct catctgagag gcactcaggg cctaatctca ggcagtaatt ttagggatgt    36960
aggggaagag atggattctg cacatacttg ggaggcttgt ggaggagtgg ggagggaggc    37020
acagggagga ctccagggtg gttcatacgg ctccctgctt ctgttcctgt cccccttttgt   37080 caagctgtgg tctgtactgc gtgttccatc ttgtttctaa gctgcttttg cccagtctttt   37140 ccagcatttc cctttcgtca tgttagtctg tgcctgtcta cgtgaactat ggtgacgttt    37200
attgggcctg gcactgtgag gtgctgggga tgtgaagatc attgtggctc agccgctgct    37260
ctcgagggcc tctgggtgca gtatgcacac ctgtgcctcc tgtttgctca ggaagacagg    37320 cttttgagatg agctggggct gacatcccca ccttatcatt gggatggctt tgggtaagtt    37380
atgttcatgt tctctgagcc tccctttcct cattggtaaa atgggtataa aatacctgcc    37440
agtggagggt tgttgtaagt agccatggaa aatgtaaagc acatagcact taccattttt    37500
tcctgtgtct ttaacagatt tatcatagaa tccccgactc agaccccatct tctagcaaaa   37560 caaggcagat catctccacc atccggacgc agaatcttcc caactgtcag ctgatttccc    37620
gaagccacta ctcccccatc tacctgtcgt tgtcatgct tttggctgcc ctgagctggc    37680
agtacctgac cactctctcc caggtaacag aagactatgt tcagactgga gaacactgat    37740
cccaaatttg tccatagctg aagtccacca taaagtggat ttactttttt tctttaagga    37800
tggatgttgt gttctcttta ttttttttcct actactttaa tccctaaaag aacgctgtgt   37860
ggctgggacc tttaggaaag tgaaatgcag gtgagaagaa cctaaacatg aaaggaaagg    37920
gtgcctcatc ccagcaacct gtccttgtgg gtgatgatca ctgtgctgct gtggctcat    37980 ggcagagcat tcagtgccac ggtttaggtg aagtcgctgc atatgtgact gtcatgagat    38040 cctactagt atgatcctgg ctagaatgat aattaaaagt atttaattg aagcaccatt     38100 tgaatgttcg tactagtaga aaatgatgtg aattttcttt ctgttcggct cctatttttc    38160
```

-continued

```
tcatcatttt gttttcttta attgggttga atggagtaga tagaaatatt tatggtttag    38220
gtaacagtta gatgtttcct aagaatgcaa actgccttt ccacacaaag gctgggaata    38280
aaattctggg tattctcgta ttctcattta aaggagttta gctttcagag agaaacagca    38340
ggattgcttt tgaccttta gaagattggt ctccagtaaa ggtggacatt tttgagattt    38400
ttataataaa gaatttaatt gctctgcatt tgtcaagtac agttcgcttg aaagcctgcc    38460
tgactgtgga aagatggag ctcaagaatg gagttgatgg cccagcgtgg tggctcatgc    38520
ctgtaatccc agcactttgg gaggctgagg cggtcggatc acgacattag gggatcgaga    38580
ccatcctggc taacacggtg aaaccccgt ctctactaaa aaaaaaaaa attagccagg    38640 cgtggtggcg ggtgcctgta gttccagcta ctcgggaggc tgaggcagga gaatggctta    38700
aacccgggag gcggagcttg cagtgagctc agatcgcgcc actgcactac cagtctgggc    38760
aacagagcga gactccatct caaaaaaagg aaaaattgt aaaaaaaaa aaaaaaaan    38820 nnnnnnnnnn nnnnnnnnnn nnnnnnnnnn nnnnnnnnnn nnnnnnnnnn nnnnnnnnnn    38880
nnnnnnnnnn nnnnnnnnnn nnnnnnnnnn nnnnnnnnnn nnnnnnnnnn nnnnnnnnnn    38940
nnnnnnnnnn nnnnnnnnnn nnnnnnnnnn nnnnnnnnnn nnnnnnnnnn nnnnnnnnnn    39000
nnnnnnnnnn nnnnnnnnnn nnnnnnnnnn nnnnnnnnnn nnnnnnnnnn nnnnnnnnnn    39060
nnnnnnnnnn nnnnnnnnnn nnnnnnnnnn nnnnnnnnnn nnnnnnnnnn nnnnnnnnnn    39120
nnnnnnnnnn nnnnnnnnnn nnnnnnnnnn nnnnnnnnnn nnnnnnnnnn nnnnnnnnnn    39180
nnnnnnnnnn nnnnnnnnnn nnnnnnnnnn nnnnnnnnnn nnnnnnnnnn nnnnnnnnnn    39240
nnnnnnnnnn nnnnnnnnnn nnnnnnnnnn nnnnnnnnnn nnnnnnnnnn nnnnnnnnnn    39300
nnnnnnnnnn nnnnnnnnnn nnnnnnnnnn nnnnnnnnnn nnnnnnnnnn nnnnnnnnnn    39360
nnnnnnnnnn nnnnnnnnnn nnnnnnnnnn nnnnnnnnnn nnnnnnnnnn nnnnnnnnnn    39420
nnnnnnnnnn nnnnnnnnnn nnnnnnnnnn nnnnnnnnnn nnnnnnnnnn nnnnnnnnnn    39480
nnnnnnnnnn nnnnnnnnnn nnnnnnnnnn nnnnnnnnnn nnnnnnnnnn nnnnnnnnnn    39540
nnnnnnnnnn nnnnnnnnnn nnnnnnnnnn nnnnnnnnnn nnnnnnnnnn nnnnnnnnnn    39600
nnnnnnnnnn nnnnnnnnnn nnnnnnnnnn nnnnnnnnnn nnnnnnnnnn nnnnnnnnnn    39660
nnnnnnnnnn nnnnnnnnnn nnnnnnnnnn nnnnnnnnnn nnnnnnnnnn nnnnnnnnnn    39720
nnnnnnnnnn nnnnnnnnnn nnnnnnnnnn nnnnnnnnnn nnnnnnnnnn nnnnnnnnnn    39780
nnnnnnnnnn nnnnnnnnnn nnnnnnnnnn nnnnnnnnnn nnnnnnnnnn nnnnnnnnnn    39840
nnnnnnnnnn nnnnnnnnnn nnnnnnnnnn nnnnnnnnnn nnnnnnnnnn nnnnnnnnnn    39900
nnnnnnnnnn nnnnnnnnnn nnnnnnnnnn nnnnnnnnnn nnnnnnnnnn nnnnnnnnnn    39960
nnnnnnnnnn nnnnnnnnnn nnnnnnnnnn nnnnnnnnnn nnnnnnnnnn nnnnnnnnnn    40020
nnnnnnnnnn nnnnnnnnnn nnnnnnnnnn nnnnnnnnnn nnnnnnnnnn nnnnnnnnnn    40080 nnnnnnnnn                                                            40090
```

<210> SEQ ID NO 4
<211> LENGTH: 417
<212> TYPE: PRT
<213> ORGANISM: Human

<400> SEQUENCE: 4

```
Met Glu Phe Val Lys Cys Leu Gly His Pro Glu Glu Phe Tyr Asn Leu
 1               5                  10                  15

Val Arg Phe Arg Ile Gly Gly Lys Arg Lys Val Met Pro Lys Met Asp
                20                  25                  30
```

-continued

```
Gln Asp Ser Leu Ser Ser Leu Lys Thr Cys Tyr Lys Tyr Leu Asn
         35                  40                  45
Gln Thr Ser Arg Ser Phe Ala Ala Val Ile Gln Ala Leu Asp Gly Glu
 50                      55                  60
Met Arg Asn Ala Val Cys Ile Phe Tyr Leu Val Leu Arg Ala Leu Asp
 65                  70                  75                  80
Thr Leu Glu Asp Asp Met Thr Ile Ser Val Glu Lys Lys Val Pro Leu
                 85                  90                  95
Leu His Asn Phe His Ser Phe Leu Tyr Gln Pro Asp Trp Arg Phe Met
             100                 105                 110
Glu Ser Lys Glu Lys Asp Arg Gln Val Leu Glu Asp Phe Pro Thr Ile
         115                 120                 125
Ser Leu Glu Phe Arg Asn Leu Ala Glu Lys Tyr Gln Thr Val Ile Ala
 130                     135                 140
Asp Ile Cys Arg Arg Met Gly Ile Gly Met Ala Glu Phe Leu Asp Lys
145                 150                 155                 160
His Val Thr Ser Glu Gln Glu Trp Asp Lys Tyr Cys His Tyr Val Ala
                165                 170                 175
Gly Leu Val Gly Ile Gly Leu Ser Arg Leu Phe Ser Ala Ser Glu Phe
            180                 185                 190
Glu Asp Pro Leu Val Gly Glu Asp Thr Glu Arg Ala Asn Ser Met Gly
        195                 200                 205
Leu Phe Leu Gln Lys Thr Asn Ile Ile Arg Asp Tyr Leu Glu Asp Gln
    210                 215                 220
Gln Gly Gly Arg Glu Phe Trp Pro Gln Glu Val Trp Ser Arg Tyr Val
225                 230                 235                 240
Lys Lys Leu Gly Asp Phe Ala Lys Pro Glu Asn Ile Asp Leu Ala Val
                245                 250                 255
Gln Cys Leu Asn Glu Leu Ile Thr Asn Ala Leu His His Ile Pro Asp
            260                 265                 270
Val Ile Thr Tyr Leu Ser Arg Leu Arg Asn Gln Ser Val Phe Asn Phe
        275                 280                 285
Cys Ala Ile Pro Gln Val Met Ala Ile Ala Thr Leu Ala Ala Cys Tyr
    290                 295                 300
Asn Asn Gln Gln Val Phe Lys Gly Ala Val Lys Ile Arg Lys Gly Gln
305                 310                 315                 320
Ala Val Thr Leu Met Met Asp Ala Thr Asn Met Pro Ala Val Lys Ala
                325                 330                 335
Ile Ile Tyr Gln Tyr Met Glu Glu Ile Tyr His Arg Ile Pro Asp Ser
            340                 345                 350
Asp Pro Ser Ser Ser Lys Thr Arg Gln Ile Ile Ser Thr Ile Arg Thr
        355                 360                 365
Gln Asn Leu Pro Asn Cys Gln Leu Ile Ser Arg Ser His Tyr Ser Pro
    370                 375                 380
Ile Tyr Leu Ser Phe Val Met Leu Leu Ala Ala Leu Ser Trp Gln Tyr
385                 390                 395                 400
Leu Thr Thr Leu Ser Gln Val Thr Glu Asp Tyr Val Gln Thr Gly Glu
                405                 410                 415
His
```

<210> SEQ ID NO 5
<211> LENGTH: 417
<212> TYPE: PRT

-continued

```
<213> ORGANISM: Human

<400> SEQUENCE: 5

Met Glu Phe Val Lys Cys Leu Gly His Pro Glu Phe Tyr Asn Leu
 1               5                  10                  15

Val Arg Phe Arg Ile Gly Gly Lys Arg Lys Val Met Pro Lys Met Asp
                20                  25                  30

Gln Asp Ser Leu Ser Ser Ser Leu Lys Thr Cys Tyr Lys Tyr Leu Asn
                35                  40                  45

Gln Thr Ser Arg Ser Phe Ala Ala Val Ile Gln Ala Leu Asp Gly Glu
        50                  55                  60

Met Arg Asn Ala Val Cys Ile Phe Tyr Leu Val Leu Arg Ala Leu Asp
65                  70                  75                  80

Thr Leu Glu Asp Asp Met Thr Ile Ser Val Glu Lys Lys Val Pro Leu
                    85                  90                  95

Leu His Asn Phe His Ser Phe Leu Tyr Gln Pro Asp Trp Arg Phe Met
                100                 105                 110

Glu Ser Lys Glu Lys Asp Arg Gln Val Leu Glu Asp Phe Pro Thr Ile
            115                 120                 125

Ser Leu Glu Phe Arg Asn Leu Ala Glu Lys Tyr Gln Thr Val Ile Ala
        130                 135                 140

Asp Ile Cys Arg Arg Met Gly Ile Gly Met Ala Glu Phe Leu Asp Lys
145                 150                 155                 160

His Val Thr Ser Glu Gln Glu Trp Asp Lys Tyr Cys His Tyr Val Ala
                165                 170                 175

Gly Leu Val Gly Ile Gly Leu Ser Arg Leu Phe Ser Ala Ser Glu Phe
                180                 185                 190

Glu Asp Pro Leu Val Gly Glu Asp Thr Glu Arg Ala Asn Ser Met Gly
            195                 200                 205

Leu Phe Leu Gln Lys Thr Asn Ile Ile Arg Asp Tyr Leu Glu Asp Gln
        210                 215                 220

Gln Gly Gly Arg Glu Phe Trp Pro Gln Glu Val Trp Ser Arg Tyr Val
225                 230                 235                 240

Lys Lys Leu Gly Asp Phe Ala Lys Pro Glu Asn Ile Asp Leu Ala Val
                245                 250                 255

Gln Cys Leu Asn Glu Leu Ile Thr Asn Ala Leu His His Ile Pro Asp
                260                 265                 270

Val Ile Thr Tyr Leu Ser Arg Leu Arg Asn Gln Ser Val Phe Asn Phe
            275                 280                 285

Cys Ala Ile Pro Gln Val Met Ala Ile Ala Thr Leu Ala Ala Cys Tyr
        290                 295                 300

Asn Asn Gln Gln Val Phe Lys Gly Ala Val Lys Ile Arg Lys Gly Gln
305                 310                 315                 320

Ala Val Thr Leu Met Met Asp Ala Thr Asn Met Pro Ala Val Lys Ala
                325                 330                 335

Ile Ile Tyr Gln Tyr Met Glu Glu Ile Tyr His Arg Ile Pro Asp Ser
            340                 345                 350

Asp Pro Ser Ser Ser Lys Thr Arg Gln Ile Ile Ser Thr Ile Arg Thr
        355                 360                 365

Gln Asn Leu Pro Asn Cys Gln Leu Ile Ser Arg Ser His Tyr Ser Pro
        370                 375                 380

Ile Tyr Leu Ser Phe Val Met Leu Leu Ala Ala Leu Ser Trp Gln Tyr
385                 390                 395                 400
```

```
Leu Thr Thr Leu Ser Gln Val Thr Glu Asp Tyr Val Gln Thr Gly Glu
            405                 410                 415

His

<210> SEQ ID NO 6
<211> LENGTH: 417
<212> TYPE: PRT
<213> ORGANISM: Human

<400> SEQUENCE: 6

Met Glu Phe Val Lys Cys Leu Gly His Pro Glu Glu Phe Tyr Asn Leu
  1               5                  10                  15

Val Arg Phe Arg Ile Gly Gly Lys Arg Lys Val Met Pro Lys Met Asp
             20                  25                  30

Gln Asp Ser Leu Ser Ser Ser Leu Lys Thr Cys Tyr Lys Tyr Leu Asn
         35                  40                  45

Gln Thr Ser Arg Ser Phe Ala Ala Val Ile Gln Ala Leu Asp Gly Glu
     50                  55                  60

Met Arg Asn Ala Val Cys Ile Phe Tyr Leu Val Leu Arg Ala Leu Asp
 65                  70                  75                  80

Thr Leu Glu Asp Asp Met Thr Ile Ser Val Glu Lys Lys Val Pro Leu
                 85                  90                  95

Leu His Asn Phe His Ser Phe Leu Tyr Gln Pro Asp Trp Arg Phe Met
            100                 105                 110

Glu Ser Lys Glu Lys Asp Arg Gln Val Leu Glu Asp Phe Pro Thr Ile
        115                 120                 125

Ser Leu Glu Phe Arg Asn Leu Ala Glu Lys Tyr Gln Thr Val Ile Ala
    130                 135                 140

Asp Ile Cys Arg Arg Met Gly Ile Gly Met Ala Glu Phe Leu Asp Lys
145                 150                 155                 160

His Val Thr Ser Glu Gln Glu Trp Asp Lys Tyr Cys His Tyr Val Ala
                165                 170                 175

Gly Leu Val Gly Ile Gly Leu Ser Arg Leu Phe Ser Ala Ser Glu Phe
            180                 185                 190

Glu Asp Pro Leu Val Gly Glu Asp Thr Glu Arg Ala Asn Ser Met Gly
        195                 200                 205

Leu Phe Leu Gln Lys Thr Asn Ile Ile Arg Asp Tyr Leu Glu Asp Gln
    210                 215                 220

Gln Gly Gly Arg Glu Phe Trp Pro Gln Glu Val Trp Ser Arg Tyr Val
225                 230                 235                 240

Lys Lys Leu Gly Asp Phe Ala Lys Pro Glu Asn Ile Asp Leu Ala Val
                245                 250                 255

Gln Cys Leu Asn Glu Leu Ile Thr Asn Ala Leu His His Ile Pro Asp
            260                 265                 270

Val Ile Thr Tyr Leu Ser Arg Leu Arg Asn Gln Ser Val Phe Asn Phe
        275                 280                 285

Cys Ala Ile Pro Gln Val Met Ala Ile Ala Thr Leu Ala Ala Cys Tyr
    290                 295                 300

Asn Asn Gln Gln Val Phe Lys Gly Ala Val Lys Ile Arg Lys Gly Gln
305                 310                 315                 320

Ala Val Thr Leu Met Met Asp Ala Thr Asn Met Pro Ala Val Lys Ala
                325                 330                 335

Ile Ile Tyr Gln Tyr Met Glu Glu Ile Tyr His Arg Ile Pro Asp Ser
            340                 345                 350
```

-continued

```
Asp Pro Ser Ser Ser Lys Thr Arg Gln Ile Ile Ser Thr Ile Arg Thr
        355                 360                 365

Gln Asn Leu Pro Asn Cys Gln Leu Ile Ser Arg Ser His Tyr Ser Pro
        370                 375                 380

Ile Tyr Leu Ser Phe Val Met Leu Leu Ala Ala Leu Ser Trp Gln Tyr
385                 390                 395                 400

Leu Ala Thr Leu Ser Gln Val Thr Glu Asp Tyr Val Gln Thr Gly Glu
                405                 410                 415

His
```

ISOLATED NUCLEIC ACID MOLECULES ENCODING HUMAN SQUALENE SYNTHASE PROTEINS, AND RELATED PRODUCTS AND PROCESSES

FIELD OF THE INVENTION

The present invention is in the field of enzyme proteins that are related to the synthase enzyme subfamily, recombinant DNA molecules, and protein production. The present invention specifically provides a novel alternative splice form of a squalene synthase enzyme and nucleic acid molecules encoding the novel splice form, all of which are useful in the development of human therapeutics and diagnostic compositions and methods.

BACKGROUND OF THE INVENTION

Many human enzymes serve as targets for the action of pharmaceutically active compounds. Several classes of human enzymes that serve as such targets include helicase, steroid esterase and sulfatase, convertase, synthase, dehydrogenase, monoxygenase, transferase, kinase, glutanase, decarboxylase, isomerase and reductase. It is therefore important in developing new pharmaceutical compounds to identify target enzyme proteins that can be put into high-throughput screening formats. The present invention advances the state of the art by providing novel human drug target enzymes related to the synthase subfamily.

Synthases

The novel human protein, and encoding gene, provided by the present invention is related to the family of synthases in general and squalene synthases (also known by such names as squalene synthetases and farnesyl-diphosphate farnesyltransferases) in particular. Furthermore, the protein of the present invention may be a novel isoform of the protein/gene provided in Genbank gi4758350. Specifically, the protein/cDNA of the present invention differs from the art-known protein of gi4758350 in that the fourth exon is spliced out of the protein/cDNA of the present invention (see the amino acid sequence alignments in FIG. 2).

Squalene synthase is important for catalyzing the first specific step in the biosynthesis of cholesterol, which is the conversion of trans-farnesyldiphosphate to squalene. Squalene synthase regulates this major control point in sterol, as well as isoprene, biosynthesis in eukaryotes (Robinson et al., *Mol Cell Biol* 1993 May;13(5):2706–17). Squalene synthase thus occupies a critical regulatory position in cholesterol synthesis (Schechter et al., *Genomics* 1994 Mar. 1;20(1):116–8). Furthermore, the squalene synthase gene has been associated with Rec syndrome (Patterson et al., *Am. J. Hum. Genet.* 57: A91 only, 1995).

Loss of promoter activity and response to sterols has been localized to a 69-bp region that is positioned 131 bp upstream from the transcription start site; this region contains a sterol regulatory element-1, which is found in other sterol regulated genes, and two possible NF1 binding sites (Guan et al., *Biol. Chem.* 270: 21958–21965, 1995).

For a further review of squalene synthases, see McKenzie et al., *J Biol Chem* 1992 Oct. 25;267(30):21368–74; Summers et al., *Gene* 1993 Dec. 22;136(1–2Che):185–92; Jiang et al., *J Biol Chem* 1993 Jun. 15;268(17):12818–24; and Soltis et al., *Arch Biochem Biophys* 1995 Feb. 1;316(2):713–23.

Due to their importance in cholesterol biosynthesis, novel human squalene synthase proteins/genes, such as provided by the present invention, are valuable as potential targets for the development of therapeutics to treat cholesterol-related diseases/disorders such as cardiovascular diseases. Furthermore, SNPs in squalene synthase genes, such as provided by the present invention, may serve as valuable markers for the diagnosis, prognosis, prevention, and/or treatment of cholesterol-related diseases/disorders such as cardiovascular diseases.

Using the information provided by the present invention, reagents such as probes/primers for detecting the SNPs or the expression of the protein/gene provided herein may be readily developed and, if desired, incorporated into kit formats such as nucleic acid arrays, primer extension reactions coupled with mass spec detection (for SNP detection), or TaqMan PCR assays (Applied Biosystems, Foster City, Calif.).

Enzyme proteins, particularly members of the synthase enzyme subfamily, are a major target for drug action and development. Accordingly, it is valuable to the field of pharmaceutical development to identify and characterize previously unknown members of this subfamily of enzyme proteins. The present invention advances the state of the art by providing previously unidentified human enzyme proteins, and the polynucleotides encoding them, that have homology to members of the synthase enzyme subfamily. These novel compositions are useful in the diagnosis, prevention and treatment of biological processes associated with human diseases.

SUMMARY OF THE INVENTION

The present invention is based in part on the identification of amino acid sequences of human enzyme peptides and proteins that are related to the synthase enzyme subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate enzyme activity in cells and tissues that express the enzyme. Experimental data as provided in FIG. 1 indicates expression in humans in placenta, T-cells from T-cell leukemia, fetal brain, pancreas, Burkitt lymphoma, bladder, and liver.

DESCRIPTION OF THE FIGURE SHEETS

FIG. 1 provides the nucleotide sequence of a cDNA sequence that encodes the enzyme protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in placenta, T-cells from T-cell leukemia, fetal brain, pancreas, Burkitt lymphoma, bladder, and liver.

FIG. 2 provides the predicted amino acid sequence of the enzyme of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the enzyme protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 55 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a enzyme protein or part of a enzyme protein and are related to the synthase enzyme subfamily. Utilizing these sequences, additional genomic sequences were assembled and transcript and/or cDNA sequences were isolated and characterized. Based on this analysis, the present invention provides amino acid sequences of a novel human synthase enzyme alternative splice form, nucleic acid sequences in the form of transcript sequences, cDNA sequences and/or genomic sequences that encode this novel enzyme splice form, nucleic acid variation (allelic information), tissue distribution of expression, and information about the closest art known protein/peptide/ domain that has structural or sequence homology to the enzyme of the present invention.

In addition to being previously unknown, the peptides that are provided in the present invention are selected based on their ability to be used for the development of commercially important products and services. Specifically, the present peptides are selected based on homology and/or structural relatedness to known enzyme proteins of the synthase enzyme subfamily and the expression pattern observed. Experimental data as provided in FIG. 1 indicates expression in humans in placenta, T-cells from T-cell leukemia, fetal brain, pancreas, Burkitt lymphoma, bladder, and liver. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known synthase family or subfamily of enzyme proteins.

SPECIFIC EMBODIMENTS

Peptide Molecules

The present invention provides nucleic acid sequences that encode protein molecules that have been identified as being members of the enzyme family of proteins and are related to the synthase enzyme subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the enzyme peptides of the present invention, enzyme peptides, or peptides/proteins of the present invention.

The present invention provides isolated peptide and protein molecules that consist of, consist essentially of, or comprise the amino acid sequences of the enzyme peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the enzyme peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated enzyme peptide can be purified from cells that naturally express it, purified from cells that have been altered to express it (recombinant), or synthesized using known protein synthesis methods. Experimental data as provided in FIG. 1 indicates expression in humans in placenta, T-cells from T-cell leukemia, fetal brain, pancreas, Burkitt lymphoma, bladder, and liver. For example, a nucleic acid molecule encoding the enzyme peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/ cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the enzyme peptides of the present invention are the naturally occurring mature proteins. A brief description of how various types of these proteins can be made/isolated is provided below.

The enzyme peptides of the present invention can be attached to heterologous sequences to form chimeric or fusion proteins. Such chimeric and fusion proteins comprise a enzyme peptide operatively linked to a heterologous protein having an amino acid sequence not substantially homologous to the enzyme peptide. "Operatively linked" indicates that the enzyme peptide and the heterologous protein are fused in-frame. The heterologous protein can be fused to the N-terminus or C-terminus of the enzyme peptide.

In some uses, the fusion protein does not affect the activity of the enzyme peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant enzyme peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A enzyme peptide-encoding nucleic acid can be cloned into such an expression vector such that the fusion moiety is linked in-frame to the enzyme peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the enzyme peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*. Lesk, A.M., ed., Oxford University Press, New York, 1988; *Biocomputing: Informatics and Genome Projects*, Smith, D.W., ed., Academic Press, New York, 1993; *Computer Analysis of Sequence Data, Part 1*, Griffin, A.M., and Griffin, H.G., eds. Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)), using a NWS gapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol.*

*Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the enzyme peptides of the present invention as well as being encoded by the same genetic locus as the enzyme peptide provided herein. The gene encoding the novel enzyme of the present invention is located on a genome component that has been mapped to human chromosome 8 (as indicated in FIG. 3), which is supported by multiple lines of evidence, such as STS and BAC map data.

Allelic variants of a enzyme peptide can readily be identified as being a human protein having a high degree (significant) of sequence homology/identity to at least a portion of the enzyme peptide as well as being encoded by the same genetic locus as the enzyme peptide provided herein. Genetic locus can readily be determined based on the genomic information provided in FIG. 3, such as the genomic sequence mapped to the reference human. The gene encoding the novel enzyme of the present invention is located on a genome component that has been mapped to human chromosome 8 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a enzyme peptide encoding nucleic acid molecule under stringent conditions as more fully described below.

FIG. 3 provides information on SNPs that have been found in the gene encoding the enzyme of the present invention. SNPs were identified at 55 different nucleotide positions, including a non-synonymous coding SNP at nucleotide position 8031 (protein position 45). The change in the amino acid sequence caused by this SNP is indicated in FIG. 3 and can readily be determined using the universal genetic code and the protein sequence provided in FIG. 2 as a reference. Some of these SNPs that are located outside the ORF and in introns may affect gene transcription.

Paralogs of a enzyme peptide can readily be identified as having some degree of significant sequence homology/identity to at least a portion of the enzyme peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a enzyme peptide encoding nucleic acid molecule under moderate to stringent conditions as more fully described below.

Orthologs of a enzyme peptide can readily be identified as having some degree of significant sequence homology/identity to at least a portion of the enzyme peptide as well as being encoded by a gene from another organism. Preferred orthologs will be isolated from mammals, preferably primates, for the development of human therapeutic targets and agents. Such orthologs will be encoded by a nucleic acid sequence that will hybridize to a enzyme peptide encoding nucleic acid molecule under moderate to stringent conditions, as more fully described below, depending on the degree of relatedness of the two organisms yielding the proteins.

Non-naturally occurring variants of the enzyme peptides of the present invention can readily be generated using recombinant techniques. Such variants include, but are not limited to deletions, additions and substitutions in the amino acid sequence of the enzyme peptide. For example, one class of substitutions are conserved amino acid substitution. Such substitutions are those that substitute a given amino acid in a enzyme peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant enzyme peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as enzyme activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the enzyme peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a enzyme peptide. Such fragments can be chosen based on the ability to retain one or more of the biological activities of the enzyme peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the enzyme peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in enzyme peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the enzyme peptides of the present invention also encompass derivatives or analogs in which a substituted amino acid residue is not one encoded by the genetic code, in which a substituent group is included, in which the mature enzyme peptide is fused with another compound, such as a compound to increase the half-life of the enzyme peptide (for example, polyethylene glycol), or in which the additional amino acids are fused to the mature enzyme peptide, such as a leader or secretory sequence or a sequence for purification of the mature enzyme peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a enzyme-effector protein interaction or enzyme-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, enzymes isolated from humans and their human/mammalian orthologs serve as targets for identifying agents for use in mammalian therapeutic applications, e.g. a human drug, particularly in modulating a biological or pathological response in a cell or tissue that expresses the enzyme. Experimental data as provided in FIG. 1 indicates that the enzymes of the present invention are expressed in humans in the placenta, T-cells from T-cell leukemia, fetal brain, pancreas, Burkitt lymphoma, and bladder, as indicated by virtual northern blot analysis. In addition, PCR-based tissue screening panels indicate expression in the liver. A large percentage of pharmaceutical agents are being developed that modulate the activity of enzyme proteins, particularly members of the synthase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in placenta, T-cells from T-cell leukemia, fetal brain, pancreas, Burkitt lymphoma, bladder, and liver. Such uses can readily be determined using the information provided herein, that which is known in the art, and routine experimentation.

The proteins of the present invention (including variants and fragments that may have been disclosed prior to the present invention) are useful for biological assays related to enzymes that are related to members of the synthase subfamily. Such assays involve any of the known enzyme functions or activities or properties useful for diagnosis and treatment of enzyme-related conditions that are specific for the subfamily of enzymes that the one of the present invention belongs to, particularly in cells and tissues that express the enzyme. Experimental data as provided in FIG. 1 indicates that the enzymes of the present invention are expressed in humans in the placenta, T-cells from T-cell leukemia, fetal brain, pancreas, Burkitt lymphoma, and bladder, as indicated by virtual northern blot analysis. In addition, PCR-based tissue screening panels indicate expression in the liver.

The proteins of the present invention are also useful in drug screening assays, in cell-based or cell-free systems. Cell-based systems can be native, i.e., cells that normally express the enzyme, as a biopsy or expanded in cell culture. Experimental data as provided in FIG. 1 indicates expression in humans in placenta, T-cells from T-cell leukemia, fetal brain, pancreas, Burkitt lymphoma, bladder, and liver. In an alternate embodiment, cell-based assays involve recombinant host cells expressing the enzyme protein.

The polypeptides can be used to identify compounds that modulate enzyme activity of the protein in its natural state or an altered form that causes a specific disease or pathology associated with the enzyme. Both the enzymes of the present invention and appropriate variants and fragments can be used in high-throughput screens to assay candidate compounds for the ability to bind to the enzyme. These compounds can be further screened against a functional enzyme to determine the effect of the compound on the enzyme activity. Further, these compounds can be tested in animal or invertebrate systems to determine activity/effectiveness. Compounds can be identified that activate (agonist) or inactivate (antagonist) the enzyme to a desired degree.

Further, the proteins of the present invention can be used to screen a compound for the ability to stimulate or inhibit interaction between the enzyme protein and a molecule that normally interacts with the enzyme protein, e.g. a substrate or a component of the signal pathway that the enzyme protein normally interacts (for example, another enzyme). Such assays typically include the steps of combining the enzyme protein with a candidate compound under conditions that allow the enzyme protein, or fragment, to interact with the target molecule, and to detect the formation of a complex between the protein and the target or to detect the biochemical consequence of the interaction with the enzyme protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant enzymes or appropriate fragments containing mutations that affect enzyme function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) enzyme activity. The assays typically involve an assay of events in the signal transduction pathway that indicate enzyme activity. Thus, the phosphorylation of a substrate, activation of a protein, a change in the expression of genes that are up- or down-regulated in response to the enzyme protein dependent signal cascade can be assayed.

Any of the biological or biochemical functions mediated by the enzyme can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the enzyme can be assayed. Experimental data as provided in FIG. 1 indicates that the enzymes of the present invention are expressed in humans in the placenta, T-cells from T-cell leukemia, fetal brain, pancreas, Burkitt lymphoma, and bladder, as indicated by virtual northern blot analysis. In addition, PCR-based tissue screening panels indicate expression in the liver.

Binding and/or activating compounds can also be screened by using chimeric enzyme proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native enzyme. Accordingly, a different set of signal transduction components is available as an end-point assay for activation. This allows for assays to be performed in other than the specific host cell from which the enzyme is derived.

The proteins of the present invention are also useful in competition binding assays in methods designed to discover compounds that interact with the enzyme (e.g. binding partners and/or ligands). Thus, a compound is exposed to a enzyme polypeptide under conditions that allow the compound to bind or to otherwise interact with the polypeptide. Soluble enzyme polypeptide is also added to the mixture. If the test compound interacts with the soluble enzyme polypeptide, it decreases the amount of complex formed or activity from the enzyme target. This type of assay is particularly useful in cases in which compounds are sought that interact with specific regions of the enzyme. Thus, the soluble polypeptide that competes with the target enzyme region is designed to contain peptide sequences corresponding to the region of interest.

To perform cell free drug screening assays, it is sometimes desirable to immobilize either the enzyme protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of enzyme-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a enzyme-binding protein and a candidate compound are incubated in the enzyme protein-presenting wells and the amount of complex trapped in the well can be quantitated. Methods for detecting such complexes, in addition to those described above for the GST-immobilized complexes, include immunodetection of complexes using antibodies reactive with the enzyme protein target molecule, or which are reactive with enzyme protein and compete with the target molecule, as well as enzyme-linked assays which rely on detecting an enzymatic activity associated with the target molecule.

Agents that modulate one of the enzymes of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of enzyme protein activity identified according to these drug screening assays can be used to treat a subject with a disorder mediated by the enzyme pathway, by treating cells or tissues that express the enzyme. Experimental data as provided in FIG. 1 indicates expression in humans in placenta, T-cells from T-cell leukemia, fetal brain, pancreas, Burkitt lymphoma, bladder, and liver. These methods of treatment include the steps of administering a modulator of enzyme activity in a pharmaceutical composition to a subject in need of such treatment, the modulator being identified as described herein.

In yet another aspect of the invention, the enzyme proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the enzyme and are involved in enzyme activity. Such enzyme-binding proteins are also likely to be involved in the propagation of signals by the enzyme proteins or enzyme targets as, for example, downstream elements of a enzyme-mediated signaling pathway. Alternatively, such enzyme-binding proteins are likely to be enzyme inhibitors.

The two-hybrid system is based on the modular nature of most transcription factors, which consist of separable DNA-binding and activation domains. Briefly, the assay utilizes two different DNA constructs. In one construct, the gene that codes for a enzyme protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a enzyme-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the enzyme protein.

This invention further pertains to novel agents identified by the above-described screening assays. Accordingly, it is within the scope of this invention to further use an agent identified as described herein in an appropriate animal model. For example, an agent identified as described herein (e.g., a enzyme-modulating agent, an antisense enzyme nucleic acid molecule, a enzyme-specific antibody, or a enzyme-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The enzyme proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in placenta, T-cells from T-cell leukemia, fetal brain, pancreas, Burkitt lymphoma, bladder, and liver. The method involves contacting a biological sample with a compound capable of interacting with the enzyme protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered enzyme activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the enzyme protein in which one or more of the enzyme functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and enzyme activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in placenta, T-cells from T-cell leukemia, fetal brain, pancreas, Burkitt lymphoma, bladder, and liver. Accordingly, methods for treatment include the use of the enzyme protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the enzyme proteins. Antibodies can be prepared from any region of the peptide as described herein. However, preferred regions will include those involved in function/activity and/or enzyme/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the enzymes of the present invention are expressed in humans in the placenta, T-cells from T-cell leukemia, fetal brain, pancreas, Burkitt lymphoma, and bladder, as indicated by virtual northern blot analysis. In addition, PCR-based tissue screening panels indicate expression in the liver. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in placenta, T-cells from T-cell leukemia, fetal brain, pancreas, Burkitt lymphoma, bladder, and liver. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in placenta, T-cells from T-cell leukemia, fetal brain, pancreas, Burkitt lymphoma, bladder, and liver. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in placenta, T-cells from T-cell leukemia, fetal brain, pancreas, Burkitt lymphoma, bladder, and liver. Thus, where a specific protein has been correlated with expression in a specific tissue, antibodies that are specific for this protein can be used to identify a tissue type.

The antibodies are also useful for inhibiting protein function, for example, blocking the binding of the enzyme peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a enzyme peptide or protein of the present invention (cDNA, transcript and genomic sequence). Such nucleic acid molecules will consist of, consist essentially of, or comprise a nucleotide sequence that encodes one of the enzyme peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the enzyme peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the enzyme proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel enzyme of the present invention is located on a genome component that has been mapped to human chromosome 8 (as indicated in FIG. 3), which is supported by multiple lines of evidence, such as STS and BAC map data.

FIG. 3 provides information on SNPs that have been found in the gene encoding the enzyme of the present invention. SNPs were identified at 55 different nucleotide positions, including a non-synonymous coding SNP at nucleotide position 8031 (protein position 45). The change in the amino acid sequence caused by this SNP is indicated in FIG. 3 and can readily be determined using the universal genetic code and the protein sequence provided in FIG. 2 as a reference. Some of these SNPs that are located outside the ORF and in introns may affect gene transcription.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6X sodium chloride/sodium citrate (SSC) at about 45C., followed by one or more washes in 0.2 X SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 55 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel enzyme of the present invention is located on a genome component that has been mapped to human chromosome 8 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the enzymes of the present invention are expressed in humans in the placenta, T-cells from T-cell leukemia, fetal brain, pancreas, Burkitt lymphoma, and bladder, as indicated by virtual northern blot analysis. In addition, PCR-based tissue screening panels indicate expression in the liver. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in enzyme protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a enzyme protein, such as by measuring a level of a enzyme-encoding nucleic acid in a sample of cells from a subject e.g., mRNA or genomic DNA, or determining if a enzyme gene has been mutated. Experimental data as provided in FIG. 1 indicates that the enzymes of the present invention are expressed in humans in the placenta, T-cells from T-cell leukemia, fetal brain, pancreas, Burkitt lymphoma, and bladder, as indicated by virtual northern blot analysis. In addition, PCR-based tissue screening panels indicate expression in the liver.

Nucleic acid expression assays are useful for drug screening to identify compounds that modulate enzyme nucleic acid expression.

The invention thus provides a method for identifying a compound that can be used to treat a disorder associated with nucleic acid expression of the enzyme gene, particularly biological and pathological processes that are mediated by the enzyme in cells and tissues that express it. Experimental data as provided in FIG. 1 indicates expression in humans in placenta, T-cells from T-cell leukemia, fetal brain, pancreas, Burkitt lymphoma, bladder, and liver. The method typically includes assaying the ability of the compound to modulate the expression of the enzyme nucleic acid and thus identifying a compound that can be used to treat a disorder characterized by undesired enzyme nucleic acid expression. The assays can be performed in cell-based and cell-free systems. Cell-based assays include cells naturally expressing the enzyme nucleic acid or recombinant cells genetically engineered to express specific nucleic acid sequences.

The assay for enzyme nucleic acid expression can involve direct assay of nucleic acid levels, such as mRNA levels, or on collateral compounds involved in the signal pathway. Further, the expression of genes that are up- or down-regulated in response to the enzyme protein signal pathway can also be assayed. In this embodiment the regulatory regions of these genes can be operably linked to a reporter gene such as luciferase.

Thus, modulators of enzyme gene expression can be identified in a method wherein a cell is contacted with a candidate compound and the expression of mRNA determined. The level of expression of enzyme mRNA in the presence of the candidate compound is compared to the level of expression of enzyme mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate enzyme nucleic acid expression in cells and tissues that express the enzyme. Experimental data as provided in FIG. 1 indicates that the enzymes of the present invention are expressed in humans in the placenta, T-cells from T-cell leukemia, fetal brain, pancreas, Burkitt lymphoma, and bladder, as indicated by virtual northern blot analysis. In addition, PCR-based tissue screening panels indicate expression in the liver. Modulation includes both up-regulation (i.e. activation or agonization) or down-regulation (suppression or antagonization) or nucleic acid expression.

Alternatively, a modulator for enzyme nucleic acid expression can be a small molecule or drug identified using the screening assays described herein as long as the drug or small molecule inhibits the enzyme nucleic acid expression in the cells and tissues that express the protein. Experimental data as provided in FIG. 1 indicates expression in humans in placenta, T-cells from T-cell leukemia, fetal brain, pancreas, Burkitt lymphoma, bladder, and liver.

The nucleic acid molecules are also useful for monitoring the effectiveness of modulating compounds on the expression or activity of the enzyme gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in enzyme nucleic acid expression, and particularly in qualitative changes that lead to pathology. The nucleic acid molecules can be used to detect mutations in enzyme genes and gene expression products such as mRNA. The nucleic acid molecules can be used as hybridization probes to detect naturally occurring genetic mutations in the enzyme gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the enzyme gene associated with a dysfunction provides a diagnostic tool for an active disease or susceptibility to disease when the disease results from overexpression, underexpression, or altered expression of a enzyme protein.

Individuals carrying mutations in the enzyme gene can be detected at the nucleic acid level by a variety of techniques. FIG. 3 provides information on SNPs that have been found in the gene encoding the enzyme of the present invention. SNPs were identified at 55 different nucleotide positions, including a non-synonymous coding SNP at nucleotide position 8031 (protein position 45). The change in the amino acid sequence caused by this SNP is indicated in FIG. 3 and can readily be determined using the universal genetic code and the protein sequence provided in FIG. 2 as a reference. Some of these SNPs that are located outside the ORF and in introns may affect gene transcription. The gene encoding the novel enzyme of the present invention is located on a genome component that has been mapped to human chromosome 8 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a enzyme gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant enzyme gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the enzyme gene in an individual in order to select an appropriate compound or dosage regimen for treatment. FIG. 3 provides information on SNPs that have been found in the gene encoding the enzyme of the present invention. SNPs were identified at 55 different nucleotide positions, including a non-synonymous coding SNP at nucleotide position 8031 (protein position 45). The change in the amino acid sequence caused by this SNP is indicated in FIG. 3 and can readily be determined using the universal genetic code and the protein sequence provided in FIG. 2 as a reference. Some of these SNPs that are located outside the ORF and in introns may affect gene transcription.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control enzyme gene expression in cells, tissues, and organisms. A DNA antisense nucleic acid molecule is designed to be complementary to a region of the gene involved in transcription, preventing transcription and hence production of enzyme protein. An antisense RNA or DNA nucleic acid molecule would hybridize to the mRNA and thus block translation of mRNA into enzyme protein.

Alternatively, a class of antisense molecules can be used to inactivate mRNA in order to decrease expression of enzyme nucleic acid. Accordingly, these molecules can treat a disorder characterized by abnormal or undesired enzyme nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the enzyme protein, such as substrate binding.

The nucleic acid molecules also provide vectors for gene therapy in patients containing cells that are aberrant in enzyme gene expression. Thus, recombinant cells, which include the patient's cells that have been engineered ex vivo and returned to the patient, are introduced into an individual where the cells produce the desired enzyme protein to treat the individual.

The invention also encompasses kits for detecting the presence of a enzyme nucleic acid in a biological sample. Experimental data as provided in FIG. 1 indicates that the enzymes of the present invention are expressed in humans in the placenta, T-cells from T-cell leukemia, fetal brain, pancreas, Burkitt lymphoma, and bladder, as indicated by virtual northern blot analysis. In addition, PCR-based tissue screening panels indicate expression in the liver. For example, the kit can comprise reagents such as a labeled or labelable nucleic acid or agent capable of detecting enzyme nucleic acid in a biological sample; means for determining the amount of enzyme nucleic acid in the sample; and means for comparing the amount of enzyme nucleic acid in the sample with a standard. The compound or agent can be packaged in a suitable container. The kit can further comprise instructions for using the kit to detect enzyme protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the enzyme proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the enzyme gene of the present invention. FIG. 3 provides information on SNPs that have been found in the gene encoding the enzyme of the present invention. SNPs were identified at 55 different nucleotide positions, including a non-synonymous coding SNP at nucleotide position 8031 (protein position 45). The change in the amino acid sequence caused by this SNP is indicated in FIG. 3 and can readily be determined using the universal genetic code and the protein sequence provided in FIG. 2 as a reference. Some of these SNPs that are located outside the ORF and in introns may affect gene transcription.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified enzyme gene of the present invention can be routinely identified using the sequence information disclosed herein can be readily incorporated into one of the established kit formats which are well known in the art, particularly expression arrays.

Vectors/host cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.,* Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.,* Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces,* and *Salmonella typhimurium.* Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroenzyme. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual 2nd, ed., Cold Spring Harbor Laboratory,* Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory,* Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as enzymes, appropriate secretion signals are incorporated into the vector. The signal sequence can be endogenous to the peptides or heterologous to these peptides.

Where the peptide is not secreted into the medium, which is typically the case with enzymes, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of vectors and host cells

The recombinant host cells expressing the peptides described herein have a variety of uses. First, the cells are useful for producing a enzyme protein or peptide that can be further purified to produce desired amounts of enzyme protein or fragments. Thus, host cells containing expression vectors are useful for peptide production.

Host cells are also useful for conducting cell-based assays involving the enzyme protein or enzyme protein fragments, such as those described above as well as other formats known in the art. Thus, a recombinant host cell expressing a native enzyme protein is useful for assaying compounds that stimulate or inhibit enzyme protein function.

Host cells are also useful for identifying enzyme protein mutants in which these functions are affected. If the mutants naturally occur and give rise to a pathology, host cells containing the mutations are useful to assay compounds that have a desired effect on the mutant enzyme protein (for example, stimulating or inhibiting function) which may not be indicated by their effect on the native enzyme protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a enzyme protein and identifying and evaluating modulators of enzyme protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the enzyme protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the enzyme protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, enzyme protein activation, and signal transduction, may not be evident from in vitro cell-free or cell-based assays. Accordingly, it is useful to provide non-human transgenic animals to assay in vivo enzyme protein function, including substrate interaction, the effect of specific mutant enzyme proteins on enzyme protein function and substrate interaction, and the effect of chimeric enzyme proteins. It is also possible to assess the effect of null mutations, that is, mutations that substantially or completely eliminate one or more enzyme protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule encoding a squalene synthase, wherein the nucleic acid molecule consists of a nucleotide sequence selected from the group consisting of
    (a) a nucleotide sequence that encodes SEQ ID NO:2, except that residue 45 of SEQ ID NO:2 is arginine;
    (b) a nucleotide sequence that encodes an amino acid sequence having at least 95% sequence identity to SEQ ID NO:2;
    (c) a nucleotide sequence having at least 95% sequence identity to SEQ ID NO:1; and
    (d) a nucleotide sequence having at least 95% sequence identity to SEQ ID NO:3.

2. An isolated nucleic acid molecule consisting of a nucleotide sequence that is completely complementary to a nucleotide sequence of claim 1.

3. A nucleic acid vector comprising the nucleic acid molecule of claim 1.

4. The vector of claim 3, wherein said vector is selected from the group consisting of a plasmid, a virus, and a bacteriophage.

5. The vector of claim 3, wherein said isolated nucleic acid molecule is inserted into said vector in proper orientation and correct reading frame such that a polypeptide having at least 95% sequence identity to SEQ ID NO:2 may be expressed by a cell transformed wit said vector.

6. The vector of claim 5, wherein said isolated nucleic acid molecule is operatively linked to a promoter sequence.

7. A host cell containing the vector of claim 3.

8. A process for producing a polypeptide comprising culturing the host cell of claim 7 under conditions sufficient for the production of the polypeptide encoded by the vector, and recovering said polypeptide.

9. An isolated nucleic acid molecule comprising a nucleotide sequence selected from the group consisting of:
    (a) a cDNA sequence that encodes SEQ ID NO:2;
    (b) SEQ ID NO:1;
    (c) nucleotides 58–1179 of SEQ ID NO:1; and
    (d) a nucleotide sequence that is completely complementary to a nucleotide sequence of any of (a)–(c).

10. A nucleic acid vector comprising the nucleic acid molecule of claim 9.

11. The vector of claim 10, wherein said vector is selected from the group consisting of a plasmid, a virus, and a bacteriophage.

12. The vector of claim 10, wherein said isolated nucleic acid molecule is inserted into said vector in proper orientation and correct reading frame such that a polypeptide comprising SEQ ID NO:2 may be expressed by a cell transformed with said vector.

13. The vector of claim 12, wherein said isolated nucleic acid molecule is operatively linked to a promoter sequence.

14. A host cell containing the vector of claim 10.

15. A process for producing a polypeptide comprising culturing the host cell of claim 14 under conditions sufficient for the production of the polypeptide encoded by the vector, and recovering said polypeptide.

16. An isolated nucleic acid molecule consisting of a nucleotide sequence selected from the group consisting of:
    (a) a nucleotide sequence tat encodes a polypeptide comprising the amino acid sequence of SEQ ID NO:2;
    (b) a nucleotide sequence consisting of SEQ ID NO:1;
    (c) a nucleotide sequence consisting of SEQ ID NO:3; and
    (d) a nucleotide sequence that is completely complementary to a nucleotide sequence of any of (a)–(c).

17. An isolated polynucleotide consisting of the nucleotide sequence of SEQ ID NO:1.

18. An isolated polynucleotide consisting of the nucleotide sequence of SEQ ID NO:3.

19. A nucleic acid vector comprising the nucleic acid molecule of claim 16.

20. The vector of claim 19, wherein said vector is selected from the group consisting of a plasmid, a virus, and a bacteriophage.

21. The vector of claim 19, wherein said isolated nucleic acid molecule is inserted into said vector in proper orientation and correct reading frame such that a polypeptide comprising SEQ ID NO:2 may be expressed by a cell transformed with said vector.

22. The vector of claim 21, wherein said isolated nucleic acid molecule is operatively linked to a promoter sequence.

23. A host cell containing the vector of claim 19.

24. A process for producing a polypeptide comprising culturing the host cell of claim 23 under conditions sufficient for the production of the polypeptide encoded by the vector, and recovering said polypeptide.

* * * * *